(12) United States Patent
Nam et al.

(10) Patent No.: US 10,752,604 B2
(45) Date of Patent: Aug. 25, 2020

(54) C-GLUCOSIDE DERIVATIVE CONTAINING FUSED PHENYL RING OR PHARMACEUTICALLY ACCEPTABLE SALT THEREOF, PROCESS FOR PREPARING SAME, AND PHARMACEUTICAL COMPOSITION COMPRISING SAME

(71) Applicant: Je Il Pharmaceutical Co., Ltd., Seoul (KR)

(72) Inventors: Joon Woo Nam, Seongnam-si (KR); Jong Yup Kim, Yongin-si (KR); Kyung Hoon Kim, Yongin-si (KR); Jung Mee Lee, Yongin-si (KR); Ji Yoon Kim, Yongin-si (KR); Ji Seon Park, Yongin-si (KR); Joseph Kim, Yongin-si (KR); Yoon Sun Park, Yongin-si (KR); Jeong Min Kim, Seongnam-si (KR)

(73) Assignee: Je Il Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 16/067,707

(22) PCT Filed: Jan. 3, 2017

(86) PCT No.: PCT/KR2017/000065
§ 371 (c)(1),
(2) Date: Jul. 2, 2018

(87) PCT Pub. No.: WO2017/119700
PCT Pub. Date: Jul. 13, 2017

(65) Prior Publication Data
US 2019/0002425 A1   Jan. 3, 2019

(30) Foreign Application Priority Data

Jan. 4, 2016  (KR) .................. 10-2016-0000610

(51) Int. Cl.
| C07H 15/203 | (2006.01) |
| C07H 7/04 | (2006.01) |
| C07D 309/10 | (2006.01) |
| A61K 31/7034 | (2006.01) |
| A61P 3/10 | (2006.01) |

(52) U.S. Cl.
CPC ........ C07D 309/10 (2013.01); A61K 31/7034 (2013.01); A61P 3/10 (2018.01); C07H 7/04 (2013.01); C07H 15/203 (2013.01); *Y02P 20/55* (2015.11)

(58) Field of Classification Search
CPC .............................. C07H 15/203; C07H 7/04
See application file for complete search history.

(56) References Cited

U.S. PATENT DOCUMENTS

| 6,414,126 B1 * | 7/2002 | Ellsworth | ............ A61K 31/70 536/17.2 |
| 2003/0114390 A1 | 6/2003 | Washburn | |

FOREIGN PATENT DOCUMENTS

| CA | 2923522 | 3/2015 |
| EA | 201100266 A1 | 10/2011 |
| JP | 2003511458 A | 3/2003 |
| JP | 2010536882 A | 12/2010 |
| JP | 2013518065 A | 5/2013 |
| JP | 2013533291 A | 8/2013 |
| JP | 2015129106 A | 7/2015 |
| KR | 10-2013-0067301 | 6/2013 |
| KR | 10-2013-0095741 | 8/2013 |
| KR | 10-2015-0081220 | 7/2015 |
| KR | 10-2015-0130177 | 11/2015 |
| RU | 2262507 C2 | 1/2004 |
| RU | 2497526 C2 | 9/2011 |
| RU | 2013107748 A | 9/2014 |
| WO | WO 2001/027128 | 4/2001 |
| WO | WO 2005/012318 | 2/2005 |
| WO | WO 2008/116195 | 9/2008 |
| WO | WO 2012/033390 | 3/2012 |
| WO | WO 2012/041898 | 4/2012 |
| WO | WO 2012/165356 | 12/2012 |
| WO | WO 2012/165914 | 12/2012 |
| WO | WO 2015/174695 | 11/2015 |
| WO | WO 2017/119700 | 7/2017 |
| WO | WO 2018/116195 | 6/2018 |

OTHER PUBLICATIONS

Chemical Abstracts Registry No. 333360-81-9, indexed in the Registry file on STN CAS Online on Apr. 27, 2001. (Year: 2001).*
International Search Report, ISA/KR, for PCT/KR2017/000065 (14/19/2017).
Levin, "Digestion and absorption of carbohydrates—from molecules and membranes to humans," Am J Clin Nutr 1994; 59(suppl):690S-8S.
Saydah, et al., "Poor Control of Risk Factors for Vascular Disease Among Adults with Previously Diagnosed *Diabetes*," J Am Med Assoc 2004; 291, 335-342.
JP Office Action for App No. JP 2018-554299 dated May 7, 2019 (with English translation (10 pages).
RU Office Action for App No. RU 2018127488/04 dated Jul. 2, 2019 (with English Translation) (22 pages).
NZ Examination Report for NZ App No. 743987, dated Oct. 18, 2018 (9 pages).
EP Extended European Search Report for App No. EP 17736073.2, dated Aug. 6, 2019 (7 pages).

* cited by examiner

*Primary Examiner* — Laura L Stockton
(74) *Attorney, Agent, or Firm* — Fish & Richardson P.C.

(57) ABSTRACT

The present disclosure relates to C-glycoside derivatives having a fused phenyl ring or pharmaceutical acceptable salts thereof, a method for preparing the same, a pharmaceutical composition comprising the same, a use thereof and a method for dual inhibition of SGLT1 and SGLT2 using the same. A novel compound of the present disclosure has a dual inhibitory activity against SGLT1 and SGLT2, thus being valuably used as a diabetes therapeutic agent.

9 Claims, No Drawings

C-GLUCOSIDE DERIVATIVE CONTAINING FUSED PHENYL RING OR PHARMACEUTICALLY ACCEPTABLE SALT THEREOF, PROCESS FOR PREPARING SAME, AND PHARMACEUTICAL COMPOSITION COMPRISING SAME

TECHNICAL FIELD

The present disclosure relates to C-glycoside derivatives having a fused phenyl ring or pharmaceutically acceptable salts thereof, a method for preparing the same, a pharmaceutical composition comprising the same, a use thereof and a method for dual inhibition of sodium-glucose cotransporter 1 (SGLT1) and sodium-glucose cotransporter 2 (SGLT2) using the same.

BACKGROUND

Diabetes is a disease, which develops complications such as abnormalities of peripheral nerves and autonomic nerves, disease symptoms of eyes, feet and kidneys, vascular diseases or the like due to an increase in blood sugar caused by a decline in insulin secretion and functions.

It is known that diabetes is generally divided into two types: Type I and Type II. Type I often occurs to children mainly due to congenital factors and requires such patients to get an insulin injection throughout the whole lifetime due to a failure of pancreas in secreting insulin, and also maintain a blood sugar in an appropriate level through a diet therapy and periodical examination. Type II mainly occurs to adults in a state that an insulin secretion declines or an insulin resistance grows enough to prevent cells from reacting to insulin due to life styles such as dietary habits, lack of exercise, obesity, etc., as well as environmental factors, wherein this type of disease accounts for 90 to 95% of 285 million patients with diabetes worldwide. Patients with type II diabetes may adjust a blood sugar through a weight loss, healthy diet and exercise, but their symptoms deteriorate due to characteristics of this progressive disease. Thus, patients have no choice but to get an insulin shot and main symptoms are polyuria, thirst, lethargy, hyperorexia, weight loss, etc., caused by a high blood sugar.

As a drug used for treating diabetes, there are roughly insulin and an oral hypoglycemic agent. Type I diabetes uses an insulin injection, while type II diabetes uses the oral hypoglycemic agent alone or in combination with insulin. As the oral hypoglycemic agent in current use, there are sulfonylurea and meglitinide drugs for stimulating insulin secretion, biguanide (metformin) and thiazolidine dione (PPAR-γ) drugs for improving insulin sensitivity, an α-glucosidase inhibitor drug for inhibiting a digestion of carbohydrates, a DPP-4 inhibitor, which is an incretin-based preparation, an SGLT2 inhibitor for preventing glucose reabsorption, etc. Despite a prescription of such oral hypoglycemic agent, many patients find it difficult to reduce glycated hemoglobin down to a target level or less. Meanwhile, in a study on diabetes patients for adjusting vascular risk factors, only 37% of those participants were able to achieve a level of glycated hemoglobin at less than 7.0% (Saydah, S. H. et. al., J. Am. Med. Assoc. 2004, 291, 335-342). Also, existing oral hypoglycemic agents exhibit side effects such as gastroenteric trouble, hypoglycemia, weight gain, lactic acidosis, edema, cardiotoxicity and hepatotoxicity along with limited durability of medicinal effects. Thus, there still remains a medical demand in the oral hypoglycemic agent field, wherein it is urgent to develop a fast-acting therapeutic agent of a new mechanism, which has excellent efficacy and durability of medicinal effects, safety and good drug tolerance, in particular without causing hypoglycemia. Therefore, much attention has been paid to a development of SGLT2 inhibitors as an oral preparation of a new mechanism, wherein it is not related to insulin, but has appropriate efficacy while being capable of reducing a weight.

A sodium-glucose cotransporter (SGLT), which is a transporter serving to absorb glucose in our body, is divided into 6 subtypes and expressed in several regions of our body, wherein the SGLT1 is mainly expressed in intestines and kidneys, while the SGLT2 is mainly expressed in kidneys. Also, the SGLT1 has a high affinity with glucose, but has a low transportation ability, while the SGLT2 has a low affinity with glucose, but has a high transportation ability. Healthy people reabsorb 99% of glucose filtered from the glomerulus of kidney, while excreting only 1% or less thereof in urine, wherein such glucose is reabsorbed at a ratio of 90% and 10% by means of SGLT2 and SGLT1, respectively. However, patients with type II diabetes have a high degree of expression of SGLT1 and SGLT2, thus have an increase in glucose absorption by means of SGLT1 in intestines and in glucose reabsorption by means of SGLT1/2 in kidneys, which results in a factor for increasing a blood sugar. Thus, there has been a development in hypoglycemic agents of a new mechanism, wherein a blood sugar is normalized through an SGLT1/2 inhibition, so as to recover an insulin secretion of pancreas and improve an insulin resistance in muscle and liver.

Phloridzin is extracted from the bark of apple tree and is a substance first evaluated as an SGLT inhibitor, wherein it has an antidiabetic efficacy, but has a low oral absorptivity and is metabolized in intestinal tracts to cause gastroenteric troubles or diarrhea, such that it has not been developed yet as a drug. Also, T-1095 was developed in 1990's as an orally absorbed SGLT2 drug by Tanabe Seiyaku, but its development was stopped in a clinical phase II, and sergliflozin or remogliflozin, which were O-glocoside having a similar structure thereto, were stopped in a clinical phase II of development. A C-glucoside drug was started to be developed in order to avoid a metabolism by means of β-glucosidase, which was a weak point of the O-glucoside drug.

As Bristol-Myers Squibb launched a clinical test on dapagliflozin in 2004, many pharmaceutical companies started to develop a drug in this series. Then, such dapagliflozin got a first permission for marketing in Europe in 2012, after which canagliflozin (Johnson & Johnson, Mitsubishi Tanabe) received a first permission for marketing in the United States in 2013, and then dapagliflozin and empagliflozin (Boehringer-Ingelheim) did so in the U.S. while ipragliflozin (Astellas), luseogliflozin (Taisho) and tofogliflozin (Chugai) did so in Japan, respectively. Meanwhile, the SGLT1 is known to play an important role in absorption of glucose and galactose in small intestines as well as in reabsorption of glucose in kidney (Levin, R. J., Am. J. Clin. Nutr. 1994, 59(3), 690S-698S). Accordingly, it is thought that the absorption of glucose may be inhibited in small intestines and the reabsorption of glucose may be inhibited in kidney by means of SGLT1 inhibition, thus exhibiting an efficacy on blood sugar control. Thus, an SGLT1/2 dual inhibitor may become a novel mechanism for treating diabetes, wherein sotagliflozin, an SGLT1/2 dual inhibitor, is now in a clinical phase III for type I diabetes and in preparation for a clinical phase III for type II diabetes, while LIK-066, an SGLT1/2 dual inhibitor of Novartis, is now in a clinical phase II, too.

DISCLOSURE

Technical Problem

An objective of the present disclosure is to provide a novel compound or pharmaceutically acceptable salts thereof, exhibiting a dual inhibitory activity against SGLT1/2.

Other objective of the present disclosure is to provide a method for preparing the same.

Another objective of the present disclosure is to provide a pharmaceutical composition for preventing or treating an SGLT1/2-related disease, comprising an inventive compound or pharmaceutically acceptable salts thereof as an effective component.

Yet another objective of the present disclosure is to provide a use thereof for preparing a drug for preventing or treating the SGLT1/2-related disease.

Still yet another objective of the present disclosure is to provide a method for preventing or treating the SGLT1/2-related disease, comprising an administration of a therapeutically effective dose of the pharmaceutical composition of the present disclosure.

Technical Solution

To achieve the objectives above, the present inventors have made efforts and identified that C-glycoside derivatives having a newly synthesized fused phenyl ring exhibit a dual inhibitory activity against SGLT1/2, thus completing the present disclosure.

C-Glycoside Derivative Compound Having a Fused Phenyl Ring

The present disclosure provides a compound represented by a following Formula 1 or pharmaceutically acceptable salts thereof:

[Formula 1]

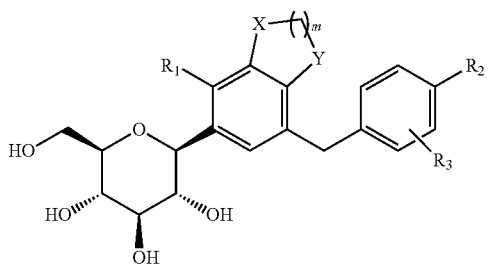

wherein,

X and Y are each independently —CH$_2$—, —CH(CH$_3$)—, —C(CH$_3$)$_2$—, —C(=O)—, —O—, —S— or —NH—;

m is an integer of 1 to 3;

R$_1$ to R$_3$ are each independently hydrogen, halogen, C1-C4 alkyl, C2-C4 alkenyl, C2-C4 alkynyl, C3-C7 cycloalkyl, —C(=O)R$_4$, cyano, hydroxy, C1-C4 alkoxy, —OCF$_3$, —SR$_5$, —S(=O)R$_6$, —S(=O)$_2$R$_7$, nitro, —N$_8$R$_9$, aryl, heteroaryl or heterocyclyl (wherein at least one hydrogen of the C1-C4 alkyl, C2-C4 alkenyl, C2-C4 alkynyl and C3-C7 cycloalkyl may be each independently unsubstituted or substituted with at least one substituent selected from the group consisting of halogen, hydroxy, cyano, nitro and amino, and at least one hydrogen of the aryl, heteroaryl and heterocyclyl may be each independently unsubstituted or substituted with at least one substituent selected from the group consisting of halogen, C1-C4 alkyl, hydroxy, C1-C4 alkoxy, cyano, nitro and amino);

R$_4$ is hydroxy, C1-C4 alkoxy, amino, mono- or di-(C1-C4 alkyl)amino;

R$_5$ is hydrogen or C1-C4 alkyl;

R$_6$ and R$_7$ are each independently C1-C4 alkyl or aryl (wherein the aryl may be unsubstituted or substituted with C1-C4 alkyl);

R$_8$ and R$_9$ are each independently hydrogen, C1-C4 alkyl, —C(=O)R$_{10}$ or —S(=O)$_2$R$_{11}$;

R$_{10}$ is C1-C4 alkyl; and

R$_{11}$ is C1-C4 alkyl or aryl; (wherein the aryl may be unsubstituted or substituted with C1-C4 alkyl);

wherein, if m is 1, R$_1$ is halogen, C1-C4 alkyl, C2-C4 alkenyl, C2-C4 alkynyl, C3-C7 cycloalkyl, —C(=O)R$_4$, cyano, hydroxy, C1-C4 alkoxy, —OCF$_3$, —SR$_8$, —S(=O)R$_6$, —S(=O)$_2$R$_7$, nitro, —N$_8$R$_9$, aryl, heteroaryl or heterocyclyl.

According to one embodiment of the present disclosure,
X and Y are each independently —CH$_2$— or —O—;
m is 1 or 2;
R$_1$ to R$_3$ are each independently hydrogen, halogen, C1-C4 alkyl, C2-C4 alkenyl, C3-C7 cycloalkyl, hydroxy, C1-C4 alkoxy, —OCF$_3$, —SR$_5$ or aryl (wherein at least one hydrogen of the C1-C4 alkyl, C2-C4 alkenyl and C3-C7 cycloalkyl may be each independently unsubstituted or substituted with halogen or hydroxy, and hydrogen of the aryl may be each independently unsubstituted or substituted with at least one substituent selected from the group consisting of halogen, C1-C4 alkyl, hydroxy and C1-C4 alkoxy); and
R$_5$ is C1-C4 alkyl.

According to other embodiment of the present disclosure,
X and Y are each independently —CH$_2$— or —O—;
m is 1 or 2;
R$_1$ is hydrogen, halogen, C1-C4 alkyl, C3-C7 cycloalkyl or C1-C4 alkoxy (wherein at least one hydrogen of the C1-C4 alkyl may be each independently unsubstituted or substituted with halogen);
R$_2$ and R$_3$ are each independently hydrogen, halogen, C1-C4 alkyl, C2-C4 alkenyl, C3-C7 cycloalkyl, C1-C4 alkoxy, —OCF$_3$, —SR$_5$ or aryl (wherein at least one hydrogen of the C1-C4 alkyl, C2-C4 alkenyl and C3-C7 cycloalkyl may be each independently unsubstituted or substituted with halogen, and at least one hydrogen of the aryl may be each independently unsubstituted or substituted with at least one substituent selected from the group consisting of halogen, C1-C4 alkyl and C1-C4 alkoxy); and
R$_5$ is C1-C4 alkyl;

In the present disclosure, as an example of halogen, there are fluorine, chlorine, bromine or iodine.

In the present disclosure, the alkyl may refer to a monovalent hydrocarbon of linear or branched chains, wherein an example of alkyl may comprise methyl, ethyl, n-propyl, i-propyl and butyl.

In the present disclosure, the cycloalkyl may comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl and cycloheptyl.

In the present disclosure, the alkoxy may refer to a linear chain, a branched chain or a ring-shaped chain, and may comprise methoxy, ethoxy, n-propoxy, isopropoxy, i-propyloxy, n-butoxy, isobutoxy, tert-butoxy and sec-butoxy.

In the present disclosure, the alkenyl may refer to a monovalent hydrocarbon of linear or branched chains, wherein an example of an alkenyl group may comprise vinyl, 1-propenyl, i-propenyl, 1-butenyl, 2-butenyl and 3-butenyl.

In the present disclosure, the aryl may refer to a monocyclic or polycyclic aryl, wherein the monocyclic aryl may comprise phenyl, biphenyl and terphenyl, and the polycyclic aryl may comprise naphthyl, anthracene, fluorene, pyrenyl and so on.

In the present disclosure, the heteroaryl may refer to the one comprising at least one hetero atom rather than carbon in the aryl.

In the present disclosure, the heterocyclyl may refer to the one comprising at least one hetero atom rather than carbon in the cycloalkyl.

In the present disclosure, the hetero atom may comprise O, S and N rather than the carbon.

According to an embodiment of the present disclosure, the X is —$CH_2$—.

According to another embodiment, the X is —O—.

According to an embodiment of the present disclosure, the Y is —$CH_2$—.

According to another embodiment, the Y is —O—.

According to an embodiment of the present disclosure, the X and Y are —$CH_2$—.

According to another embodiment, the X and Y are —O—.

According to an embodiment of the present disclosure, one of the X and Y is —$CH_2$—, and the other is —O—.

According to an embodiment of the present disclosure, the $R_1$ is hydrogen.

According to other embodiment of the present disclosure, the $R_1$ is halogen.

Particularly, the $R_1$ may be chlorine.

According to other embodiment of the present disclosure, the $R_1$ is C1-C4 alkoxy. Particularly, the said $R_1$ is a methoxy group.

According to another embodiment of the present disclosure, the $R_1$ is C1-C4 alkyl. The C1-C4 alkyl may be methyl, ethyl, propyl, butyl, isobutyl or isopropyl.

According to another embodiment of the present disclosure, the $R_1$ is C3-C7 cycloalkyl. The C3-C7 cycloalkyl may be cyclopentyl.

According to an embodiment of the present disclosure, the $R_4$ is hydrogen.

According to an embodiment of the present disclosure, the $R_2$ is C1-C4 alkyl. The C1-C4 alkyl may be methyl, ethyl, propyl, butyl, isobutyl or isopropyl.

At least one hydrogen of the C1-C4 alkyl may be each independently unsubstituted or substituted with halogen, particularly with fluorine.

According to another embodiment of the present disclosure, the $R_2$ is C1-C4 alkenyl. The C2-C4 alkenyl may be particularly vinyl.

According to another embodiment of the present disclosure, the $R_2$ is C1-C4 alkoxy. The C1-C4 alkoxy may be methoxy, ethoxy or isopropoxy.

According to another embodiment of the present disclosure, the $R_2$ is —$OCF_3$.

According to another embodiment of the present disclosure, the $R_2$ may be halogen.

Particularly, the $R_2$ may be fluorine or chlorine.

According to another embodiment of the present disclosure, the $R_2$ is —$SR_5$ and the $R_5$ is C1-C4 alkyl.

According to another embodiment of the present disclosure, the $R_2$ is aryl.

Particularly, the aryl may be phenyl.

According to an embodiment of the present disclosure, the $R_3$ is hydrogen.

According to another embodiment of the present disclosure, the $R_3$ is C1-C4 alkoxy. Particularly, the C1-C4 alkoxy may be methoxy, ethoxy or isopropoxy.

According to another embodiment of the present disclosure, the $R_3$ is C1-C4 alkyl. Particularly, the C1-C4 alkyl may be methyl, ethyl, propyl, butyl, isobutyl or isopropyl.

According to an embodiment of the present disclosure, the $R_3$ may be substituted in a 3rd position of a benzene ring of Formula i).

According to another embodiment aspect of the present disclosure, the $R_3$ may be substituted in a 2nd position of a benzene ring of Formula i).

According to a preferred embodiment aspect of the present disclosure, a compound represented by the Formula 1 above may be selected from the group consisting of following compounds:

(2R,3S,4R,5R,6S)-2-(hydroxymethyl)-6-(7-(4-methoxybenzyl)-4-methyl-2,3-dihydro-1H-inden-5-yl)tetrahydro-2H-pyran-3,4,5-triol;

(2S,3R,4R,5S,6R)-2-(7-(4-ethoxybenzyl)-4-methyl-2,3-dihydro-1H-inden-5-yl)-6-(hydroxymethyl)tetrahydro-2H-pyran-3,4,5-triol;

(2R,3S,4R,5R,6S)-2-(hydroxymethyl)-6-(7-(4-isopropoxybenzyl)-4-methyl-2,3-dihydro-1H-inden-5-yl)tetrahydro-2H-pyran-3,4,5-triol;

(2R,3S,4R,5R,6S)-2-(hydroxymethyl)-6-(4-methyl-7-(4-methylbenzyl)-2,3-dihydro-1H-inden-5-yl)tetrahydro-2H-pyran-3,4,5-triol;

(2S,3R,4R,5S,6R)-2-(7-(4-ethylbenzyl)-4-methyl-2,3-dihydro-1H-inden-5-yl)-6-(hydroxymethyl)tetrahydro-2H-pyran-3,4,5-triol;

(2R,3S,4R,5R,6S)-2-(hydroxymethyl)-6-(4-methyl-7-(4-propylbenzyl)-2,3-dihydro-1H-inden-5-yl)tetrahydro-2H-pyran-3,4,5-triol;

(2R,3S,4R,5R,6S)-2-(hydroxymethyl)-6-(7-(4-isopropylbenzyl)-4-methyl-2,3-dihydro-1H-inden-5-yl)tetrahydro-2H-pyran-3,4,5-triol;

(2R,3S,4R,5R,6S)-2-(hydroxymethyl)-6-(4-methyl-7-(4-vinylbenzyl)-2,3-dihydro-1H-inden-5-yl)tetrahydro-2H-pyran-3,4,5-triol;

(2R,3S,4R,5R,6S)-2-(hydroxymethyl)-6-(4-methyl-7-(4-trifluoromethyl)benzyl)-2,3-dihydro-1H-inden-5-yl)tetrahydro-2H-pyran-3,4,5-triol;

(2R,3S,4R,5R,6S)-2-(hydroxymethyl)-6-(4-methyl-7-(4-trifluoromethoxy)benzyl)-2,3-dihydro-1H-inden-5-yl)tetrahydro-2H-pyran-3,4,5-triol;

(2S,3R,4R,5S,6R)-2-(7-(3,4-dimethoxybenzyl)-4-methyl-2,3-dihydro-1H-inden-5-yl)-6-(hydroxymethyl)tetrahydro-2H-pyran-3,4,5-triol;

(2S,3R,4R,5S,6R)-2-(7-(2,4-dimethoxybenzyl)-4-methyl-2,3-dihydro-1H-inden-5-yl)-6-(hydroxymethyl)tetrahydro-2H-pyran-3,4,5-triol;

(2R,3S,4R,5R,6S)-2-(hydroxymethyl)-6-(4-methyl-7-(4-methylthio)benzyl)-2,3-dihydro-1H-inden-5-yl)tetrahydro-2H-pyran-3,4,5-triol;

(2S,3R,4R,5S,6R)-2-(7-(4-fluorobenzyl)-4-methyl-2,3-dihydro-1H-inden-5-yl)-6-(hydroxymethyl)tetrahydro-2H-pyran-3,4,5-triol;

(2S,3R,4R,5S,6R)-2-(7-(4-fluoro-3-methylbenzyl)-4-methyl-2,3-dihydro-1H-inden-5-yl)-6-(hydroxymethyl)tetrahydro-2H-pyran-3,4,5-triol;

(2S,3R,4R,5S,6R)-2-(7-(4-chlorobenzyl)-4-methyl-2,3-dihydro-1H-inden-5-yl)-6-(hydroxymethyl)tetrahydro-2H-pyran-3,4,5-triol;

(2S,3R,4R,5S,6R)-2-(8-(4-ethoxybenzyl)-2,3-dihydrobenzo[b][1,4]dioxin-6-yl)-6-(hydroxymethyl)tetrahydro-2H-pyran-3,4,5-triol;

(2S,3R,4R,5S,6R)-2-(8-(4-ethylbenzyl)-2,3-dihydrobenzo[b][1,4]dioxin-6-yl)-6-(hydroxymethyl)tetrahydro-2H-pyran-3,4,5-triol;

(2R,3S,4R,5R,6S)-2-(hydroxymethyl)-6-(7-(4-methoxybenzyl)benzo[d][1,3]dioxol-5-yl)tetrahydro-2H-pyran-3,4,5-triol;

(2R,3S,4R,5R,6S)-2-(hydroxymethyl)-6-(7-(4-(methyhthio)benzyl)benzo[d][1,3]dioxol-5-yl)tetrahydro-2H-pyran-3,4,5-triol;

(2S,3R,4R,5S,6R)-2-(7-(4-ethylbenzyl)benzo[d][1,3]dioxol-5-yl)-6-(hydroxymethyl)tetrahydro-2H-pyran-3,4,5-triol;

(2S,3R,4R,5S,6R)-2-(4-(4-ethoxybenzyl)-5,6,7,8-tetrahydronaphthalene-2-yl)-6-(hydroxymethyl)tetrahydro-2H-pyran-3,4,5-triol;

(2S,3R,4R,5S,6R)-2-(4-(4-ethylbenzyl)-5,6,7,8-tetrahydronaphthalene-2-yl)-6-(hydroxymethyl)tetrahydro-2H-pyran-3,4,5-triol;

(2R,3S,4R,5R,6S)-2-(hydroxymethyl)-6-(4-(4-methoxybenzy)-1-methyl-5,6,7,8-tetrahydronaphthalene-2-yl)tetrahydro-2H-pyran-3,4,5-triol;

(2R,3S,4R,5R,6S)-2-(hydroxymethyl)-6-(1-methyl-4-(4-methylbenzyl)-5,6,7,8-tetrahydronaphthalene-2-yl)tetrahydro-2H-pyran-3,4,5-triol;

(2R,3S,4R,5R,6S)-2-(hydroxymethyl)-6-(1-methyl-4-(4-trifluoromethyl)benzyl)-5,6,7,8-tetrahydronaphthalene-2-yl)tetrahydro-2H-pyran-3,4,5-triol;

(2R,3S,4R,5R,6S)-2-(hydroxymethyl)-6-(1-methyl-4-(4-trifluoromethoxy)benzyl)-5,6,7,8-tetrahydronaphthalene-2-yl)tetrahydro-2H-pyran-3,4,5-triol;

(2R,3S,4R,5R,6S)-2-(hydroxymethyl)-6-(1-methyl-4-(4-(methylthio)benzyl)-5,6,7,8-tetrahydronaphthalene-2-yl)tetrahydro-2H-pyran-3,4,5-triol;

(2S,3R,4R,5S,6R)-2-(4-(4-chlorobenzyl)-1-methyl-5,6,7,8-tetrahydronaphthalene-2-yl)-6-(hydroxymethyl)tetrahydro-2H-pyran-3,4,5-triol;

(2R,3S,4R,5R,6S)-2-(hydroxymethyl)-6-(7-(4-methoxybenzyl)-4-methyl-2,3-dihydrobenzofuran-5-yl)tetrahydro-2H-pyran-3,4,5-triol;

(2S,3R,4R,5S,6R)-2-(7-(4-ethoxybenzyl)-4-methyl-2,3-dihydrobenzofuran-5-yl)-6-(hydroxymethyl)tetrahydro-2H-pyran-3,4,5-triol;

(2R,3S,4R,5R,6S)-2-(hydroxymethyl)-6-(4-methyl-7-(4-(methyhthio)benzyl)-2,3-dihydrobenzofuran-5-yl)tetrahydro-2H-pyran-3,4,5-triol;

(2S,3R,4R,5S,6R)-2-(7-(4-ethylbenzyl)-4-methyl-2,3-dihydrobenzofuran-5-yl)-6-(hydroxymethyl)tetrahydro-2H-pyran-3,4,5-triol;

(2R,3S,4R,5R,6S)-2-(hydroxymethyl)-6-(4-methyl-7-(4-vinylbenzyl)-2,3-dihydrobenzofuran-5-yl)tetrahydro-2H-pyran-3,4,5-triol;

(2S,3R,4R,5S,6R)-2-(4-chloro-7-(4-ethoxybenzyl)-2,3-dihydrobenzofuran-5-yl)-6-(hydroxymethyl)tetrahydro-2H-pyran-3,4,5-triol;

(2R,3S,4R,5R,6S)-2-(hydroxymethyl)-6-(4-(4-methoxybenzyl)-7-methy-2,3-dihydrobenzofuran-6-yl)tetrahydro-2H-pyran-3,4,5-triol;

(2R,3S,4R,5R,6S)-2-(hydroxymethyl)-6-(7-methyl-4-(4-vinylbenzyl)-2,3-dihydrobenzofuran-6-yl)tetrahydro-2H-pyran-3,4,5-triol;

(2R,3S,4R,5R,6S)-2-(hydroxymethyl)-6-(8-methoxy-5-(4-methoxybenzyl)chroman-7-yl)tetrahydro-2H-pyran-3,4,5-triol;

(2R,3 S,4R,5R,6S)-2-(hydroxymethyl)-6-(8-methoxy-5-(4-methylbenzyl)chroman-7-yl)tetrahydro-2H-pyran-3,4,5-triol;

(2S,3R,4R,5S,6R)-2-(5-(4-ethoxybenzyl)-8-methylchroman-7-yl)-6-(hydroxymethyl)tetrahydro-2H-pyran-3,4,5-triol;

(2S,3R,4R,5S,6R)-2-(4-ethyl-7-(4-methylbenzyl)-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-methoxybenzyl)-2,3-dihydro-1H-indene-5-yl)-6-(hydroxymethyl)tetrahydro-2H-pyran-3,4,5-triol;

(2S,3R,4R,5S,6R)-2-(7-(4-ethoxybenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-ethylbenzyl)-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-fluorobenzyl)-2,3-dihydro-1H-indene-5-yl)-6-(hydroxymethyl)tetrahydro-2H-pyran-3,4,5-triol;

(2S,3R,4R,5S,6R)-2-(7-(4-chlorobenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-trifluoromethoxy)benzyl)-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-trifluoromethyl)benzyl)-2,3-dihydro-1H-indene-5-yl)-6-(hydroxymethyl)tetrahydro-2H-pyran-3,4,5-triol;

(2S,3R,4R,5S,6R)-2-(7-(4-isopropoxybenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(7-(4-isopropylbenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(7-(biphenyl-3-ylmethyl)-4-ethyl-2,3-dihydro-1H-indene-5-yl)-6-(hydroxymethyl)tetrahydro-2H-pyran-3,4,5-triol;

(2R,3S,4R,5R,6S)-2-(hydroxymethyl)-6-(7-(4-methoxybenzyl)-4-propyl-2,3-dihydro-1H-indene-5-yl)tetrahydro-2H-pyran-3,4,5-triol;

(2R,3S,4R,5R,6S)-2-(hydroxymethyl)-6-(7-(4-methylbenzyl)-4-propyl-2,3-dihydro-1H-indene-5-yl)tetrahydro-2H-pyran-3,4,5-triol;

(2S,3R,4R,5S,6R)-2-(7-(4-ethoxybenzyl)-4-propyl-2,3-dihydro-1H-indene-5-yl)-6-(hydroxymethyl)tetrahydro-2H-pyran-3,4,5-triol;

(2S,3R,4R,5S,6R)-2-(7-(4-ethylbenzyl)-4-propyl-2,3-dihydro-1H-indene-5-yl)-6-(hydroxymethyl)tetrahydro-2H-pyran-3,4,5-triol;

(2S,3R,4R,5S,6R)-2-(7-(4-fluorobenzyl)-4-propyl-2,3-dihydro-1H-indene-5-yl)-6-(hydroxymethyl)tetrahydro-2H-pyran-3,4,5-triol;

(2S,3R,4R,5S,6R)-2-(4-butyl-7-(4-methoxybenzyl)-2,3-dihydro-1H-indene-5-yl)-6-(hydroxymethyl)tetrahydro-2H-pyran-3,4,5-triol;

(2S,3R,4R,5S,6R)-2-(4-butyl-7-(4-methylbenzyl)-2,3-dihydro-1H-indene-5-yl)-6-(hydroxymethyl)tetrahydro-2H-pyran-3,4,5-triol;

(2S,3R,4R,5S,6R)-2-(4-butyl-7-(4-ethoxybenzyl)-2,3-dihydro-1H-indene-5-yl)-6-(hydroxymethyl)tetrahydro-2H-pyran-3,4,5-triol;

(2S,3R,4R,5S,6R)-2-(4-butyl-7-(4-ethylbenzyl)-2,3-dihydro-1H-indene-5-yl)-6-(hydroxymethyl)tetrahydro-2H-pyran-3,4,5-triol;

(2R,3S,4R,5R,6S)-2-(hydroxymethyl)-6-(4-isopropyl-7-(4-methoxybenzyl)-2,3-dihydro-1H-inden-5-yl)tetrahydro-2H-pyran-3,4,5-triol;
(2R,3S,4R,5R,6S)-2-(hydroxymethyl)-6-(4-isopropyl-7-(4-methoxybenzyl)-2,3-dihydro-1H-inden-5-yl)tetrahydro-2H-pyran-3,4,5-triol;
(2S,3R,4R,5S,6R)-2-(4-cyclopentyl-7-(4-methylbenzyl)-2,3-dihydro-1H-inden-5-yl)-6-(hydroxymethyl)tetrahydro-2H-pyran-3,4,5-triol;
(2R,3S,4R,5R,6S)-2-(hydroxymethyl)-6-(4-isobutyl-7-(4-methylbenzyl)-2,3-dihydro-1H-inden-5-yl)tetrahydro-2H-pyran-3,4,5-triol;
(2S,3R,4R,5S,6R)-2-(7-(4-ethylbenzyl)-4-isobutyl-2,3-dihydro-1H-inden-5-yl)-6-(hydroxymethyl)tetrahydro-2H-pyran-3,4,5-triol;

A compound of Formula 1 of the present disclosure may be present in a form of pharmaceutically acceptable salt. Acid-addition salt formed by means of pharmaceutically acceptable free acid is useful as the salt. In the present disclosure, the term "pharmaceutically acceptable salt" means any and all organic acid or inorganic acid-addition salts of the said compound, wherein a side effect caused by these salts does not lower an advantageous efficacy of the compound represented by Formula 1 at a concentration thereof having a relatively nontoxic and harmless effective action to patients.

The acid-addition salts are prepared by means of a conventional method, for example, in such a way that a compound is dissolved in an excessive amount of acid aqueous solution, and then resulting salts are deposited by means of a water miscible organic solvent, for example, methanol, ethanol, acetone or acetonitrile. The same molar amounts of the compound and acid in water or alcohol (ex. glycol monomethyl ether) may be heated, and then the said mixture may be evaporated and dried, or precipitated salts may be suction-filtered.

At this time, organic acid and inorganic acid may be used as free acid, wherein hydrochloric acid, phosphoric acid, sulfuric acid, nitric acid, tartaric acid or the like may be used as the inorganic acid, while the following may be used as the organic acid: methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid or the like, but not limited thereto.

Also, the pharmaceutically acceptable metal salts may be made by means of a base. Alkali metallic salt or alkali earth metal salt is obtained, for example, in such a way that a compound is dissolved in an excessive amount of alkali metal hydroxide or alkali earth metal hydroxide solution, and then undissolved compound salt is filtered, after which a remaining solution liquid was evaporated and dried. At this time, as the metallic salt, it is pharmaceutically appropriate to prepare, in particular, sodium, potassium or calcium salts, but not limited thereto. Also, silver salt corresponding thereto may be obtained in such a way that alkali metal or alkali earth metal salts are reacted with an appropriate silver salt (ex. silver nitrate).

The pharmaceutically acceptable salts of the present disclosure comprise a salt of acid or basic group, which may be present in a compound of the Formula 1 above, unless specified otherwise. For example, the pharmaceutically acceptable salts may comprise sodium, calcium, potassium salts and the like of a hydroxy group, while as other pharmaceutically acceptable salts of an amino group, there are hydrobromide, sulfate, hydrogen sulphate, phosphate, hydrogen phosphate, dihydrogen phosphate, acetate, succinate, citrate, tartrate, lactate, mandelate, methanesulfonate (mesylate), p-toluenesulfonate (tosylate) salts and the like, wherein they may be prepared by means of a method for preparing salts known in the art.

A Method for Preparing a C-Glycoside Derivative Compound Having a Fused Phenyl Ring The present disclosure provides a method for preparing a C-glycoside derivative compound having a fused phenyl ring represented by a Formula 1 or pharmaceutically acceptable salts thereof.

A compound of the Formula I of the present disclosure may be prepared by means of following steps:

(S1) reacting a compound of a following Formula II with a compound of a following Formula III to obtain a compound of a following Formula IV; and (S2) performing deprotection-reduction or reduction-deprotection for the compound of the Formula IV above to obtain a compound of a following Formula I:

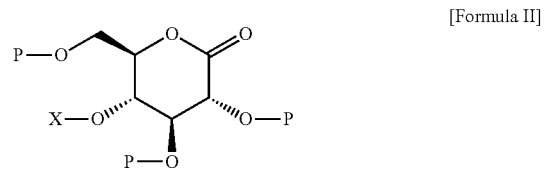

[Formula II]

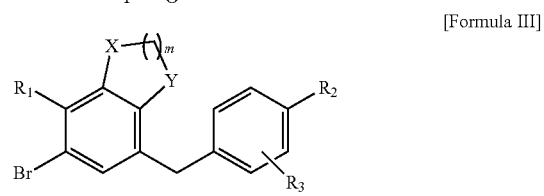

[Formula III]

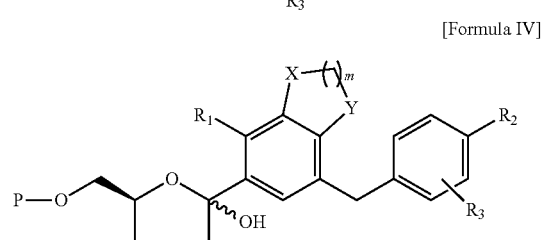

[Formula IV]

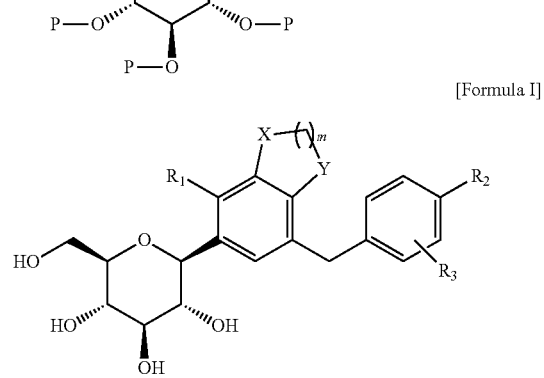

[Formula I]

wherein,
X, Y, m, $R_1$, $R_2$ and $R_3$ are as defined herein, and P is trimethylsilyl or benzyl.

In one embodiment of the present disclosure, if P is trimethylsilyl, a compound of a following Formula V may be obtained by deprotecting the compound of the Formula IV, and the compound of the Formula I may be obtained by reducing the compound of the Formula V:

[Formula V]

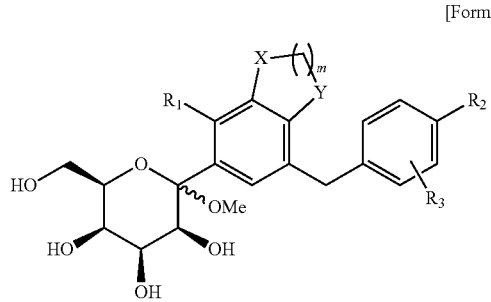

wherein,

X, Y, m, $R_1$, $R_2$ and $R_3$ are as defined herein.

In other embodiment of the present disclosure, if P is benzyl, a compound of a following Formula VI may be obtained by reducing the compound of the Formula IV, and the compound of the Formula I may be obtained by deprotecting the compound of the Formula VI:

[Formula VI]

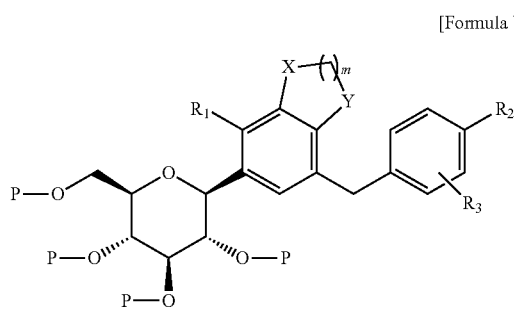

wherein,

X, Y, m, $R_1$, $R_2$, $R_3$ and P are as defined herein.

A detailed method for preparing the compound represented by the Formula 1 of the present disclosure or the pharmaceutically acceptable salts thereof is as shown in Reaction Formula 1 and Reaction Formula 2, wherein a preparation method that is modified to meet the level of those skilled in the art is also comprised herein.

[Reaction Formula 1]

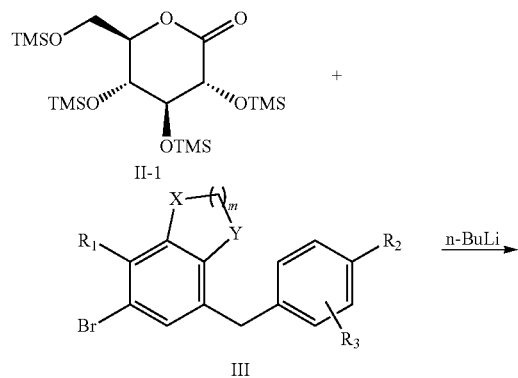

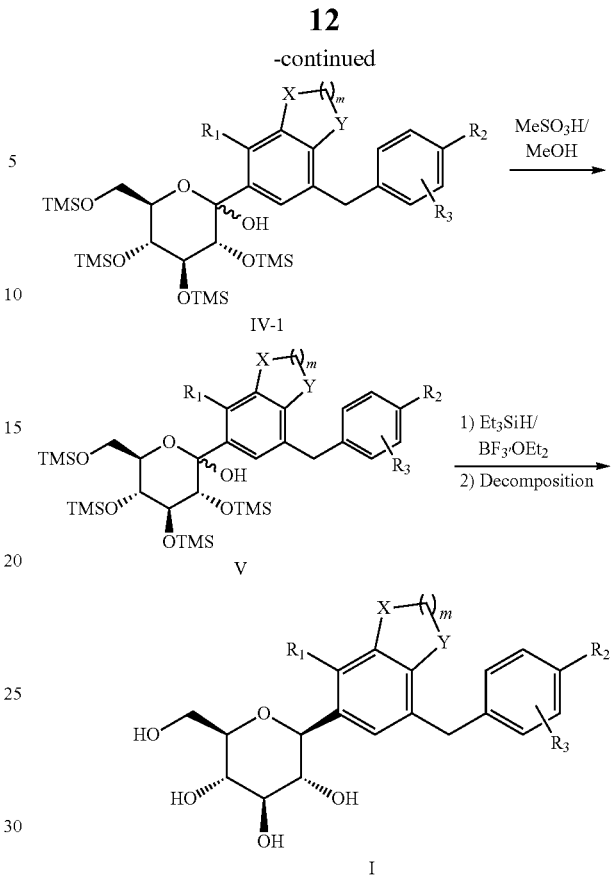

A lithium-halogen exchange reaction of a brominated compound III was performed, after which a resulting product was reacted with a persilylated gluconolacton compound II-1, so as to prepare a lactol mixture IV-1. The resulting mixture was treated with methanesulfonic acid out of methanol within the same reaction system, thus being converted into a desilylated O-methyl lactol compound V A reduction of an anomer methoxy group of the lactol compound V was performed by means of triethylsilane and boron trifluoride diethyletherate, so as to produce a mixture corresponding to α,β-isomer. A necessary β-isomer I is decomposed into a peracetylated mixture of a final compound or by means of a selective crystalization of HPLC for aliquoting.

[Reaction Formula 2]

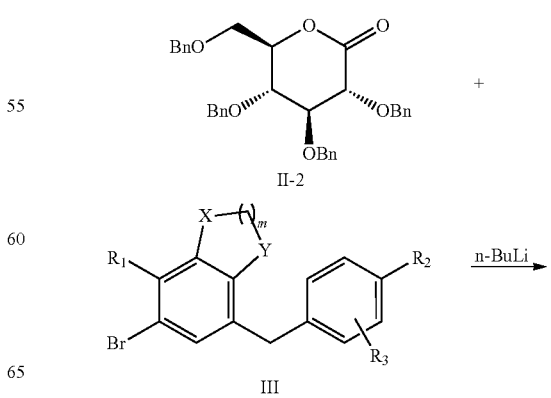

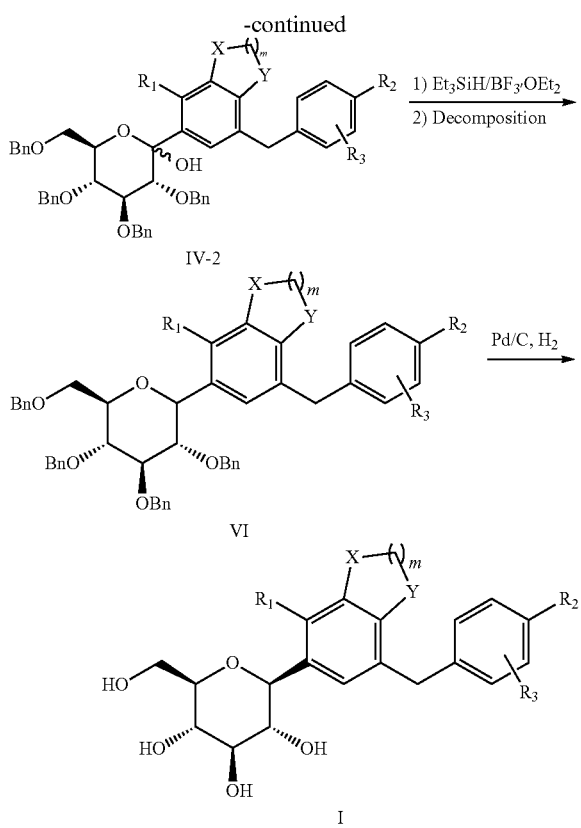

Also, a lactol compound IV-2 was prepared by means of a perbenzylated gluconic lactone compound II-2, after which a reduction of an anomer hydroxy group of the lactol compound IV-2 was performed by means of triethylsilane and boron trifluoride diethyletherate, so as to produce a mixture corresponding to α,β-isomer. A necessary β-isomer VI was decomposed by means of selective crystallization. A benzyl group of a compound VI was deprotected by means of Pd/C in a hydrogen atmosphere, so as to obtain a target compound I.

A Composition Comprising a C-Glycoside Derivative Compound Having a Fused Phenyl Ring, a Use Thereof, and a Treatment Method Using the Same The present disclosure provides a pharmaceutical composition for preventing or treating an SGLT activity-related disease, comprising a compound represented by a following Formula 1 or pharmaceutically acceptable salts thereof as an effective component.

[Formula I]

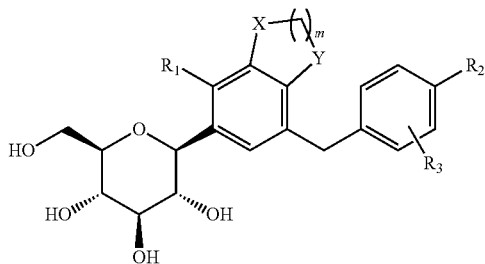

The Formula 1 above is as defined above.

A compound of the Formula 1 of the present disclosure or pharmaceutically acceptable salts thereof may exhibit an inhibitory activity against SGLT1, SGLT2 or both thereof. Thus, the compound of the Formula 1 of the present disclosure or the pharmaceutically acceptable salts thereof may be valuably used for treating or preventing diabetes.

For administration, the pharmaceutical composition of the present disclosure may further comprise at least one of pharmaceutically acceptable carriers in addition to the compound represented by the Formula 1 above or the pharmaceutically acceptable salts thereof. The pharmaceutically acceptable carriers used may be saline solution, sterilized water, Ringer solution, buffered saline, dextrose solution, maltodextrin solution, glycerol, ethanol and a mixture of at least one component thereof, wherein other conventional additives such as antioxidant, buffer solution, bacteristat, etc., may be also added thereto, if necessary. Also, diluent, a dispersing agent, surfactant, a binding agent and lubricant may be additionally added into the pharmaceutical composition of the present disclosure, such that it may be formulated into a dosage form for injection such as aqueous solution, suspension, emulsion, etc., pill, capsule, granule, tablet or the like. Thus, the composition of the present disclosure may be a patch, liquid, pill, capsule, granule, tablet, suppository, etc. Such preparations may be prepared by means of a conventional method used for formulation in the art or a method disclosed in Remington's Pharmaceutical Science (latest edition), Mack Publishing Company, Easton Pa., wherein the composition may be formulated into various preparations according to each disease or component.

The composition of the present disclosure may be orally or parenterally administered (for example, applied intravenously, subcutaneously, intraperitoneally or locally) according to a targeted method, wherein a scope of its dose varies according to a patient's weight, age, gender, health condition, diet, administration time, administration method, excretion rate, severity of disease and the like. A aily dose of the compound represented by the Formula 1 of the present disclosure may amount to about 1 to 1000 mg/kg, preferably 5 to 100 mg/kg, wherein it may be administered once a day or divided into several times a day.

The pharmaceutical composition of the present disclosure may further comprise at least one effective component, which exhibits the same or similar medicinal effect, in addition to the compound represented by the Formula 1 above or the pharmaceutically acceptable salts thereof.

The present disclosure provides a method for preventing or treating the SGLT activity-related disease, comprising an administration of a therapeutically effective amount of the compound represented by the Formula 1 above or the pharmaceutically acceptable salts thereof.

As used herein, the term "therapeutically effective amount" refers to an amount of the compound represented by the Formula 1 above, which is effective in prevention or treatment of the SGLT activity-related disease.

Also, the present disclosure may inhibit SGLT1, SGLT2 or both thereof, in such a way that the compound represented by the Formula 1 above or the pharmaceutically acceptable salts thereof is administered into mammals including humans.

The inventive method for preventing or treating the SGLT activity-related disease also comprises handling the disease itself before expression of its symptoms as well as inhibiting or avoiding the symptoms thereof, by means of an administration of the compound represented by the Formula 1 above. In management of diseases, a preventive or therapeutic dosage of a certain active component may vary depending on nature and severity of disease or condition, and a path in which the active component is administered. A dosage and a frequency thereof may vary depending on an individual patient's age, weight and response.

A suitable dosage & usage may be easily selected by those skilled in the art, naturally considering such factors. Also, the inventive method for preventing or treating the SGLT activity-related disease may further comprise an administration of a therapeutically effective amount of an additional active preparation, which is helpful in treatment of the diseases along with the compound represented by the Formula 1 above, wherein such additional active preparation may exhibit a synergy effect or auxiliary effect along with the compound of the Formula 1 above.

The present disclosure also provides a use of the compound represented by the Formula 1 above or the pharmaceutically acceptable salts thereof, in order to prepare a drug for treating the SGLT activity-related disease. The compound represented by the Formula 1 above for preparing a drug may be combined with an acceptable adjuvant, diluent, carrier, etc., and may be prepared into a complex preparation along with other active preparations, thus having a synergy action of active components.

Matters mentioned in the use, composition, treatment method of the present disclosure are equally applied unless they contradict to each other.

Advantageous Effects

Novel C-glycoside derivatives of the present disclosure may dually inhibit SGLT1 and SGLT2, thus may be valuably used in treatment or prevention of diabetes.

MODE FOR INVENTION

Hereinafter, the configurations and effects of the present disclosure will be described in more detail through Examples. However, the following Examples are provided only for the purpose of illustrating the present disclosure, and thus the scope of the present disclosure is not limited thereto.

Example 1. Preparation of (2R,3S,4R,5R,6S)-2-(hydroxymethyl)-6-(7-(4-methoxybenzyl)-4-methyl-2,3-dihydro-1H-indene-5-yl)tetrahydro-2H-pyran-3,4,5-triol Step 1. Synthesis of ethyl 7-methyl-2,3-dihydro-1H-indene-4-carboxylate (1-1)

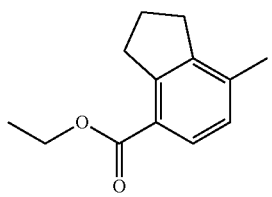

(1-1)

A mixture of ethyl sorbate (25.0 mL, 170 mmol, TCI reagent) in xylene (100 mL) and 1-pyrrolidino-1-cyclopentene (24.8 mL, 170 mmol, TCI agent) was stirred at reflux overnight. After a reaction was completed, a volatile solvent was evaporated under reduced pressure. EtOAc was added into a resulting mixture. An organic layer was washed with brine, after which a resulting product was dried over anhydrous MgSO$_4$, filtered and concentrated under vacuum. A crude compound was used in a following step without an additional purification. S$_8$ (5.45 g, 170 mmol) was added into the crude compound. A reaction mixture was stirred at 250° C. for 2 hours. After a reaction was completed, the resulting mixture was distilled under reduced pressure, so as to obtain the title compound (1-1) (20.0 g, 97.9 mmol, 58%).

$^1$H NMR (400 MHz, CDCl$_3$); δ 7.76 (d, J=7.6 Hz, 1H), 7.03 (d, J=8.0 Hz, 1H), 4.34 (q, J=7.2 Hz, 2H), 3.30 (t, J=7.6 Hz, 2H), 2.84 (t, J=7.6 Hz, 2H), 2.30 (s, 3H), 2.12-2.05 (m, 2H), 1.38 (t, J=7.2 Hz, 3H)

Step 2. Synthesis of ethyl 6-bromo-7-methyl-2,3-dihydro-1H-indene-4-carboxylate (1-2)

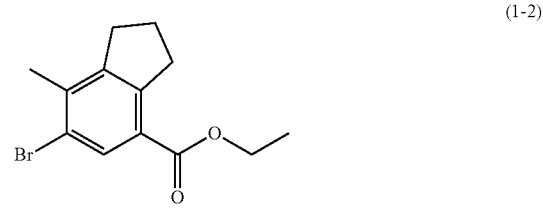 [SMILES: CCOC(=O)c1cc(Br)c(C)c2c1CCC2]

(1-2)

Br$_2$ (6.0 mL, 117 mmol) and AgNO$_3$ (16.6 g, 97.9 mmol) in water (20 mL) were added dropwise into a mixture of the compound (1-1) (20.0 g, 97.9 mmol) in AcOH (100 mL) and a concentrated HNO$_3$ (4.4 mL) at room temperature. A resulting mixture was stirred overnight at room temperature. A reaction was completed with saturated Na$_2$S$_2$O$_3$ solution, so as to perform an extraction with EtOAc. An organic layer was dried over anhydrous MgSO$_4$, filtered and concentrated under vacuum. A resulting residue was purified by means of a silica gel column chromatography, so as to obtain the title compound (1-2) (22.1 g, 78.0 mmol, 80%).

$^1$H NMR (400 MHz, CDCl$_3$); δ 8.02 (s, 1H), 4.34 (q, J=7.2 Hz, 2H), 3.25 (t, J=7.6 Hz, 2H), 2.90 (t, J=7.6 Hz, 2H), 2.37 (s, 3H), 2.11-2.07 (m, 2H), 1.39 (t, J=7.2 Hz, 3H).

Step 3. Synthesis of 6-bromo-7-methyl-2,3-dihydro-1H-indene-4-carboxylic acid (1-3)

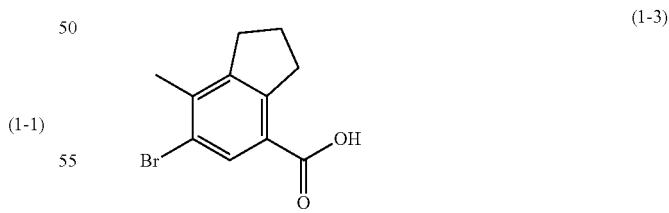

(1-3)

LiOH.H$_2$O (9.82 g, 234 mmol) was added into a solution of the compound (1-2) (22.1 g, 78.0 mmol) in THF/MeOH/water (120 mL/40 mL/40 mL) at room temperature. A reaction mixture was stirred overnight at room temperature. After a reaction was completed, a volatile substance was removed under reduced pressure. A 1N—HCl aqueous solution was added into a residue to carry out acidification, during which a resulting mixture was stirred to precipitate a crude product. The crude product was filtered, washed with water and dried under high vacuum, so as to obtain the title compound (1-3) (15.4 g, 60.4 mmol, 77%).

$^1$H NMR (400 MHz, CDCl$_3$); δ 8.08 (s, 1H), 3.28 (t, J=7.6 Hz, 2H), 2.91 (t, J=7.6 Hz, 2H), 2.38 (s, 3H), 2.13-2.09 (m, 2H).

Step 4. Synthesis of (6-bromo-7-methyl-2,3-dihydro-1H-indene-4-yl)(4-methoxyphenyl)methanone (1-4)

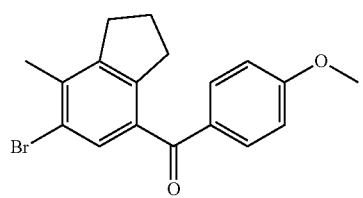

(1-4)

DMF (0.12 mL) and (COCl)$_2$ (2.46 mL, 29.0 mmol) were added dropwise into a solution of 6-bromo-7-methyl-2,3-dihydro-1H-indene-4-carboxylic acid (1-3) (4.94 g, 19.3 mmol) in DCM (45 mL) at 0° C. in a nitrogen atmosphere. A resulting solution was stirred overnight at room temperature, after which a resulting mixture was concentrated under vacuum, so as to obtain a crude oxychloride. 4-methoxybenzene (2.52 mL, 23.2 mmol) and AlCl$_3$ (3.09 g, 23.2 mmol) were fractionally added into a crude oxychloride solution in DCM (45 mL) at 0° C. A resulting mixture was heated up to room temperature and stirred for 2 hours at room temperature. A resulting mixture was poured onto ice water, so as to perform an extraction with EtOAc. An organic layer was washed with brine, after which a resulting product was dried over anhydrous MgSO$_4$, filtered and concentrated under vacuum. A resulting residue was purified by means of a silica gel column chromatography, so as to obtain the title compound (1-4) (4.84 g, 14.02 mmol, 73%).

$^1$H NMR (400 MHz, CDCl$_3$); δ 7.78 (d, J=8.8 Hz, 2H), 7.49 (s, 1H), 6.95 (d, J=8.8 Hz, 2H), 3.89 (s, 3H), 2.97-2.91 (m, 4H), 2.39 (s, 3H), 2.11-2.03 (m, 2H)

Step 5. Synthesis of 5-bromo-7-(4-methoxybenzyl)-4-methyl-2,3-dihydro-1H-indene (1-5)

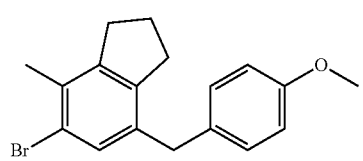

(1-5)

Triethylsilane (4.61 mL, 28.0 mmol) and BF$_3$.OEt$_2$ (3.55 mL, 28.0 mmol) were added dropwise into a solution of the compound (1-4) (4.84 g, 14.0 mmol) in DCM/acetonitrile (20 mL/20 mL) at 0° C. in a nitrogen atmosphere. A resulting mixture was slowly heated up to room temperature and stirred overnight at room temperature. A saturated NaHCO$_3$ aqueous solution was slowly added into the resulting mixture, so as to perform an extraction with EtOAc. An organic layer was washed with brine, after which a resulting product was dried over anhydrous MgSO$_4$, filtered and concentrated under vacuum. A resulting residue was purified by means of a silica gel column chromatography, so as to obtain the title compound (1-5) (4.21 g, 12.7 mmol, 91%).

$^1$H NMR (400 MHz, CDCl$_3$); δ 7.12 (s, 1H), 7.05 (d, J=8.4 Hz, 2H), 6.81 (d, J=8.4 Hz, 2H), 3.80 (s, 2H), 3.78 (s, 3H), 2.87 (t, J=7.4 Hz, 2H), 2.75 (t, J=7.6 Hz, 2H), 2.29 (s, 3H), 2.08-2.00 (m, 2H)

Step 6. Synthesis of (2R,3R,4R,5S,6S)-3,4,5-tris(benzyloxy)-2-(benzyloxymethyl)-6-(7-(4-methoxybenzyl)-4-methyl-2,3-dihydro-1H-indene-5-yl)tetrahydro-2H-pyran (1-6)

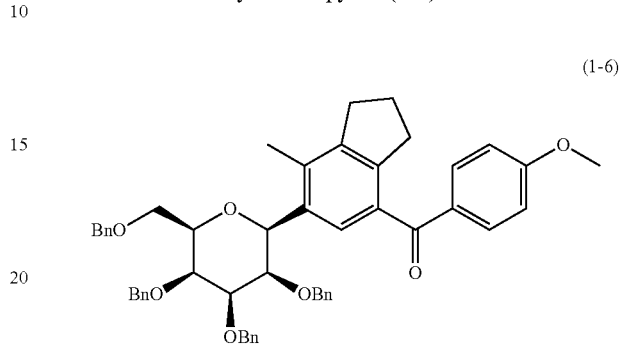

(1-6)

n-BuLi (12.4 mL, 30.9 mmol, 2.5 M in n-hexane) was added into a solution of the compound (1-5) (6.82 g, 20.6 mmol) in toluene/THF (70 mL/70 mL) at −78° C. in a nitrogen atmosphere. In 30 minutes later, perbenzylated gluconolactone (14.4 g, 26.8 mmol) in toluene (70 mL) was added into a resulting mixture at −78° C. The resulting mixture was stirred at the same temperature for 2 hours. A reaction was completed with water, so as to perform an extraction with EtOAc. An organic layer was dried over anhydrous MgSO$_4$, filtered and concentrated under vacuum, such that a crude intermediate was obtained and used without an additional purification. Triethylsilane (10.1 mL, 61.8 mmol) and BF$_3$.OEt$_2$ (7.83 mL, 61.8 mmol) were added into an intermediate solution in DCM/acetonitrile (100 mL/100 mL) at −78° C. in a nitrogen atmosphere. A resulting mixture was heated up to −60° C. for 1 hour. A saturated NaHCO$_3$ solution was slowly added into the resulting mixture, so as to perform an extraction with EtOAc. An organic layer was dried over anhydrous MgSO$_4$, filtered and concentrated under vacuum. A resulting residue was purified by means of a silica gel column chromatography, so as to obtain the title compound (1-6) (8.78 g, 11.32 mmol, 55%).

$^1$H NMR (400 MHz, CDCl$_3$); δ 7.32-7.11 (m, 19H), 7.02 (d, J=8.8 Hz, 2H), 6.87 (d, J=6.4 Hz, 2H), 6.71 (d, J=8.0 Hz, 2H), 4.96-4.87 (m, 3H), 4.68-4.63 (m, 2H), 4.54-4.49 (m, 2H), 4.35 (d, J=10.4 Hz, 1H), 3.86-3.75 (m, 7H), 3.72 (s, 3H), 3.67-3.57 (m, 2H), 2.85-2.77 (m, 4H), 2.24 (s, 3H), 2.08-2.01 (m, 2H)

Step 7. Synthesis of a Target Compound

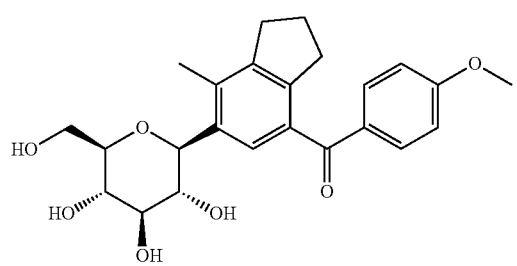 [SMILES: COc1ccc(C(=O)c2cc([C@@H]3O[C@H](CO)[C@@H](O)[C@H](O)[C@H]3O)c(C)c3c2CCC3)cc1]

A suspension of the compound (1-6) (152 mg, 0.20 mmol) in THF (3 mL) and MeOH (3 mL) as well as Pd/C (20% wt %, 30 mg) was stirred at room temperature in a hydrogen atmosphere for 16 hours. A reaction mixture was filtered with a celite pad, and concentrated under vacuum. A resulting residue was purified by means of a silica gel column chromatography, so as to obtain the target compound (79 mg, 0.19 mmol, 95%).

$^1$H NMR (400 MHz, CD$_3$OD); δ 7.11 (s, 1H), 7.04 (d, J=8.4 Hz, 2H), 6.78 (d, J=8.4 Hz, 2H), 4.45 (d, J=9.2 Hz, 1H), 3.88-3.84 (m, 3H), 3.74 (s, 3H), 3.68-3.64 (m, 1H), 3.56 (t, J=8.8 Hz, 1H), 3.52-3.47 (m, 1H), 3.40-3.38 (m, 2H), 2.84 (t, J=7.6 Hz, 2H), 2.73 (t, J=7.6 Hz, 2H), 2.28 (s, 3H), 2.01-1.98 (m, 2H)

Examples 2 and 3

Target compounds of Examples 2 and 3 were obtained by means of a method as shown in Example 1.

Example 2. Preparation of (2S,3R,4R,5S,6R)-2-(7-(4-ethoxybenzyl)-4-methyl-2,3-dihydro-1H-indene-5-yl)-6-(hydroxymethyl)tetrahydro-2H-pyran-3,4,5-triol

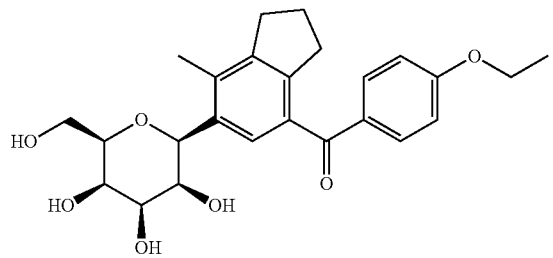 [SMILES: CCOc1ccc(C(=O)c2cc([C@@H]3O[C@H](CO)[C@H](O)[C@H](O)[C@@H]3O)c(C)c3c2CCC3)cc1]

$^1$H NMR (400 MHz, CD$_3$OD); δ 7.10 (s, 1H), 7.03 (d, J=8.4 Hz, 2H), 6.76 (d, J=8.8 Hz, 2H), 4.45 (d, J=8.8 Hz, 1H), 3.97 (q, J=6.8 Hz, 2H), 3.88-3.84 (m, 3H), 3.67-3.48 (m, 4H), 3.40-3.38 (m, 2H), 2.84 (t, J=7.6 Hz, 2H), 2.73 (t, J=7.6 Hz, 2H), 2.28 (s, 3H), 2.02-1.97 (m, 2H), 1.35 (t, J=6.8 Hz, 3H)

Example 3. Preparation of (2R,3S,4R,5R,6S)-2-(hydroxymethyl)-6-(7-(4-isopropoxybenzyl)-4-methyl-2,3-dihydro-1H-indene-5-yl)tetrahydro-2H-pyran-3,4,5-triol

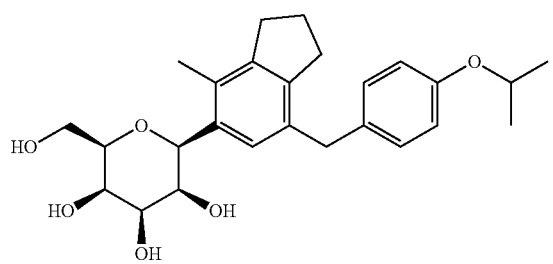 [SMILES: Cc1c([C@@H]2O[C@H](CO)[C@H](O)[C@H](O)[C@@H]2O)cc(Cc2ccc(OC(C)C)cc2)c2c1CCC2]

$^1$H NMR (400 MHz, CD$_3$OD); δ 7.11 (s, 1H), 7.02 (d, J=8.4 Hz, 2H), 6.76 (d, J=8.8 Hz, 2H), 4.54-4.48 (m, 1H), 4.45 (d, J=9.2 Hz, 1H), 3.84-3.88 (m, 3H), 3.66 (dd, J=11.6, 5.2 Hz, 1H), 3.59-3.48 (m, 2H), 3.41-3.38 (m, 2H), 2.85 (t, J=7.6 Hz, 2H), 2.74 (t, J=7.4 Hz, 2H), 2.28 (s, 3H), 2.04-1.96 (m, 2H), 1.27 (d, J=6.0 Hz, 6H)

Example 4. Preparation of (2R,3S,4R,5R,6S)-2-(hydroxymethyl)-6-(4-methyl-7-(4-methylbenzyl)-2,3-dihydro-1H-indene-5-yl)tetrahydro-2H-pyran-3,4,5-triol Step 1. Synthesis of (6-bromo-7-methyl-2,3-dihydro-1H-indene-4-yl)methanol (4-1)

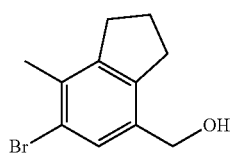

(4-1)

A BH$_3$·SMe$_2$ complex (13.7 mL, 137.2 mmol, 10.0 M in methylsulfide) was slowly added into a solution of 6-bromo-7-methyl-2,3-dihydro-1H-indene-4-carboxylic acid (1-3) (3.50 g, 13.7 mmol) in THF (50 mL) at 0° C. in a nitrogen atmosphere, after which a reaction mixture was stirred overnight at room temperature. The resulting reaction mixture was cooled at 0° C., after which a saturated NaHCO$_3$ aqueous solution was slowly added into the resulting mixture, so as to perform an extraction with EtOAc. An organic layer was dried over anhydrous MgSO$_{04}$, filtered and concentrated under vacuum. A resulting residue was purified by means of a silica gel column chromatography, so as to obtain the title compound (4-1) (2.33 g, 9.66 mmol, 70%).

$^1$H NMR (400 MHz, CDCl$_3$); δ 7.39 (s, 1H), 4.60 (d, J=6.0 Hz, 2H), 2.91-2.86 (m, 4H), 2.32 (s, 3H), 2.14-2.07 (m, 2H), 1.48 (t, J=5.8 Hz, 1H)

Step 2. Synthesis of 5-bromo-7-(bromomethyl)-4-methyl-2,3-dihydro-1H-indene (4-2)

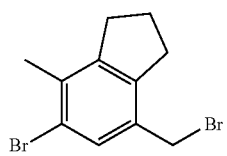

(4-2)

PBr$_3$ (1.38 mL, 14.5 mmol) was added dropwise into a solution of the compound (4-1) (2.33 g, 9.66 mmol) in toluene (45 mL) at 0° C. in a nitrogen atmosphere. A resulting mixture was slowly heated up to room temperature and stirred for 2 hours at room temperature. A saturated NaHCO$_3$ aqueous solution was slowly added into the resulting mixture, so as to perform an extraction with EtOAc. An organic layer was dried over anhydrous MgSO$_4$, filtered and concentrated under vacuum. A resulting residue was purified by means of a silica gel column chromatography, so as to obtain the title compound (4-2) (2.14 g, 7.04 mmol, 73%).

$^1$H NMR (400 MHz, CDCl$_3$); δ 7.35 (s, 1H), 4.40 (s, 2H), 2.95-2.88 (m, 4H), 2.31 (s, 3H), 2.18-2.10 (m, 2H)

Step 3. Synthesis of 5-bromo-4-methyl-7-(4-methylbenzyl)-2,3-dihydro-1H-indene (4-3)

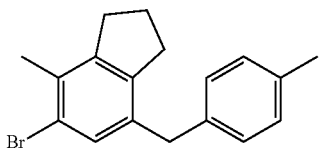

(4-3)

The compound (4-2) (150 mg, 0.49 mmol), 4-methylphenylboronic acid (81 mg, 0.59 mmol) and $K_2CO_3$ (136 mg, 0.99 mmol) were dissolved in acetone/water (3 mL/1 mL), after which $Pd_2(dba)_3$ (90 mg, 0.10 mmol) was added into a resulting mixture. The resulting mixture was stirred at room temperature for 4 hours. A resulting reaction mixture was filtered with celite, and distributed between EtOAc and water. A water layer was extracted with EtOAc, after which a combined organic layer was dried over anhydrous $MgSO_4$, filtered and concentrated under vacuum. A resulting residue was purified by means of a silica gel column chromatography, so as to obtain the title compound (4-3) (130 mg, 0.41 mmol, 84%).

$^1$H NMR (400 MHz, $CDCl_3$); δ 7.14 (s, 1H), 7.08 (d, J=7.6 Hz, 2H), 7.02 (d, J=8.0 Hz, 2H), 3.82 (s, 2H), 2.87 (t, J=7.4 Hz, 2H), 2.75 (d, J=7.6 Hz, 2H), 2.31 (s, 3H), 2.29 (s, 3H), 2.08-2.02 (m, 2H)

Step 4. Synthesis of a Target Compound

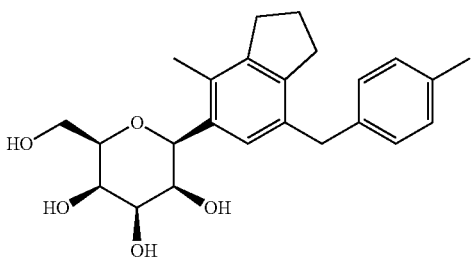 [SMILES: Cc1ccc(Cc2cc([C@@H]3O[C@H](CO)[C@H](O)[C@H](O)[C@@H]3O)c(C)c3c2CCC3)cc1]

n-BuLi (0.25 mL, 0.62 mmol, 2.5 M in n-hexane) was added into a solution of the compound (4-3) (130 mg, 0.41 mmol) in toluene/THF (3 mL/1.5 mL) at −78° C. in a nitrogen atmosphere. In 30 minutes later, TMS-protected gluconolactone (231 mg, 0.49 mmol) in toluene (3 mL) was added into a resulting mixture at −78° C. The resulting mixture was stirred at the same temperature for 2 hours. Methane sulfonic acid (0.2 mL) and MeOH (1.6 mL) were added into the reaction mixture at the same temperature. The reaction mixture was stirred at −78° C. for 2 hours. A reaction was completed with a saturated $NaHCO_3$ solution, so as to perform an extraction with EtOAc. An organic layer was dried over anhydrous $MgSO_4$, filtered and concentrated under vacuum, so as to obtain a crude intermediate, which was used without an additional purification. Triethylsilane (0.14 mL, 0.82 mmol) and $BF_3.OEt_2$ (0.11 mL, 0.82 mmol) were added into an intermediate solution in DCM/acetonitrile (2 mL/2 mL) at −78° C. in a nitrogen atmosphere. A resulting mixture was heated up to −50° C. for 1 hour. A saturated $NaHCO_3$ solution was slowly added into the resulting mixture, so as to perform an extraction with EtOAc. An organic layer was dried over anhydrous $MgSO_4$, filtered and concentrated under vacuum. A resulting residue was purified with Prep. HPLC, so as to obtain a target compound (5.6 mg, 0.014 mmol, 3.4%).

$^1$H NMR (400 MHz, $CD_3OD$); δ 7.11 (s, 1H), 7.04-6.99 (m, 4H), 4.45 (d, J=9.2 Hz, 1H), 3.88-3.86 (m, 3H), 3.66 (dd, J=11.6, 5.6 Hz, 1H), 3.59-3.48 (m, 2H), 3.40-3.35 (m, 2H), 2.84 (t, J=7.6 Hz, 2H), 2.72 (t, J=7.6 Hz, 2H), 2.29 (s, 3H), 2.27 (s, 3H), 2.04-1.96 (m, 2H)

Examples 5 to 16

Target compounds of Examples 5 to 16 were obtained by means of a method as shown in Example 4.

Example 5. Preparation of (2S,3R,4R,5S,6R)-2-(7-(4-ethylbenzyl)-4-methyl-2,3-dihydro-1H-indene-5-yl)-6-(hydroxymethyl)tetrahydro-2H-pyran-3,4,5-triol

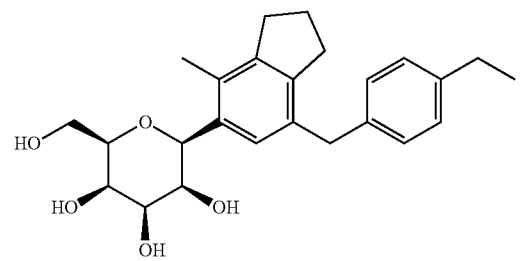 [SMILES: CCc1ccc(Cc2cc([C@@H]3O[C@H](CO)[C@H](O)[C@H](O)[C@@H]3O)c(C)c3c2CCC3)cc1]

$^1$H NMR (400 MHz, $CD_3OD$); δ 7.12 (s, 1H), 7.06-7.02 (m, 4H), 4.45 (d, J=9.2 Hz, 1H), 3.88-3.86 (m, 3H), 3.68-3.48 (m, 3H), 3.40-3.39 (m, 2H), 2.85 (t, J=7.6 Hz, 2H), 2.73 (t, J=7.6 Hz, 2H), 2.58 (q, J=7.6 Hz, 2H), 2.29 (s, 3H), 2.01-1.98 (m, 2H), 1.19 (t, J=8.0 Hz, 3H)

Example 6. Preparation of (2R,3S,4R,5R,6S)-2-(hydroxymethyl)-6-(4-methyl-7-(4-propylbenzyl)-2,3-dihydro-1H-indene-5-yl)tetrahydro-2H-pyran-3,4,5-triol

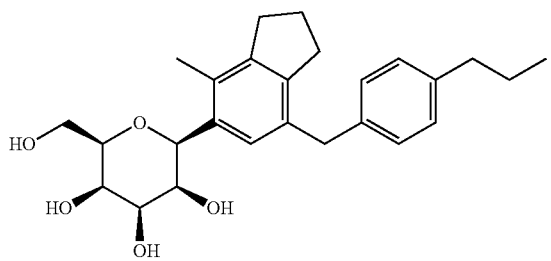 [SMILES: CCCc1ccc(Cc2cc([C@@H]3O[C@H](CO)[C@H](O)[C@H](O)[C@@H]3O)c(C)c3c2CCC3)cc1]

$^1$H NMR (400 MHz, $CD_3OD$); δ 7.11 (s, 1H), 7.03 (s, 4H), 4.45 (d, J=9.2 Hz, 1H), 3.88-3.86 (m, 3H), 3.66 (dd, J=11.6, 5.6 Hz, 1H), 3.59-3.48 (m, 2H), 3.41-3.39 (m, 2H), 2.85 (t, J=7.6 Hz, 2H), 2.74 (d, J=7.6 Hz, 2H), 2.52 (t, J=7.6 Hz, 2H), 2.29 (s, 3H), 2.04-1.96 (m, 2H), 1.65-1.55 (m, 2H), 0.91 (t, J=7.2 Hz, 3H)

Example 7. Preparation of (2R,3S,4R,5R,6S)-2-(hydroxymethyl)-6-(7-(4-isopropylbenzyl)-4-methyl-2,3-dihydro-1H-inden-5-yl)tetrahydro-2H-pyran-3,4,5-triol

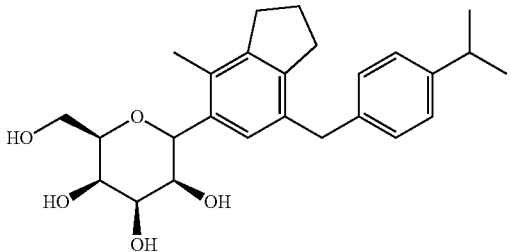 [SMILES: Cc1c(C2O[C@H](CO)[C@H](O)[C@H](O)[C@@H]2O)cc(Cc2ccc(C(C)C)cc2)c2c1CCC2]

¹H NMR (400 MHz, CD₃OD); δ 7.12-7.03 (m, 5H), 4.45 (d, J=9.2 Hz, 1H), 3.88-3.86 (m, 3H), 3.66 (dd, J=12.0, 5.6 Hz, 1H), 3.57 (t, J=9.2 Hz, 1H), 3.52-3.48 (m, 1H), 3.41-3.39 (m, 2H), 2.87-2.81 (m, 3H), 2.74 (t, J=7.2 Hz, 2H), 2.29 (s, 3H), 2.04-1.98 (m, 2H), 1.21 (d, J=7.2 Hz, 6H)

Example 8. Preparation of (2R,3S,4R,5R,6S)-2-(hydroxymethyl)-6-(4-methyl-7-(4-vinylbenzyl)-2,3-dihydro-1H-inden-5-yl)tetrahydro-2H-pyran-3,4,5-triol

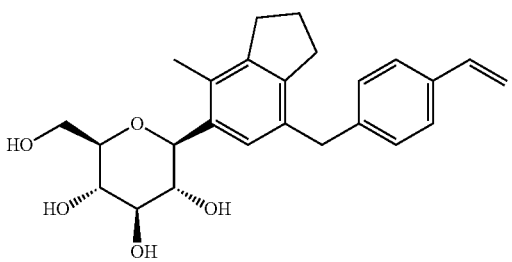

¹H NMR (400 MHz, CD₃OD); δ 7.33 (d, J=8.4 Hz, 2H), 7.10 (d, J=8.0 Hz, 2H), 7.03 (s, 1H), 6.66 (dd, J=17.6, 11.2 Hz, 1H), 5.73 (d, J=18.0 Hz, 1H), 5.17 (d, J=10.0 Hz, 1H), 4.95-4.92 (m, 2H), 4.69 (d, J=4.0 Hz, 1H), 4.38-4.37 (m, 1H), 4.22 (d, J=8.4 Hz, 1H), 3.83 (s, 2H), 3.70-3.65 (m, 1H), 3.30-3.16 (m, 1H), 2.76 (t, J=7.2 Hz, 2H), 2.71-2.66 (m, 2H), 2.17 (s, 3H), 1.94-1.90 (m, 2H)

Example 9. Preparation of (2R,3S,4R,5R,6S)-2-(hydroxymethyl)-6-(4-methyl-7-(4-trifluoromethyl)benzyl)-2,3-dihydro-1H-inden-5-yl)tetrahydro-2H-pyran-3,4,5-triol

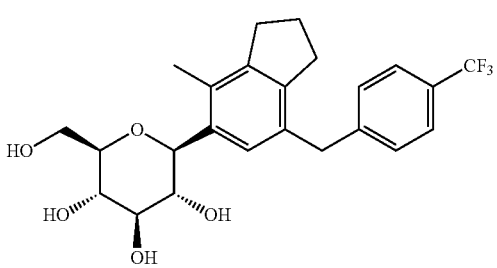 [SMILES: Cc1c([C@@H]2O[C@H](CO)[C@@H](O)[C@H](O)[C@H]2O)cc(Cc2ccc(C(F)(F)F)cc2)c2c1CCC2]

¹H NMR (400 MHz, CD₃OD); δ 7.45 (d, J=8.0 Hz, 2H), 7.26 (d, J=8.4 Hz, 2H), 7.08 (s, 1H), 4.39 (d, J=8.8 Hz, 1H), 3.94 (s, 2H), 3.80 (d, J=11.2 Hz, 1H), 3.59 (dd, J=12.0, 5.2 Hz, 1H), 3.51-3.41 (m, 2H), 3.34-3.32 (m, 2H), 2.78 (t, J=7.6 Hz, 2H), 2.65 (t, J=7.6 Hz, 2H), 2.22 (s, 3H), 1.95-1.92 (m, 2H)

Example 10. Preparation of (2R,3S,4R,5R,6S)-2-(hydroxymethyl)-6-(4-methyl-7-(4-trifluoromethoxy)benzyl)-2,3-dihydro-1H-inden-5-yl)tetrahydro-2H-pyran-3,4,5-tiol

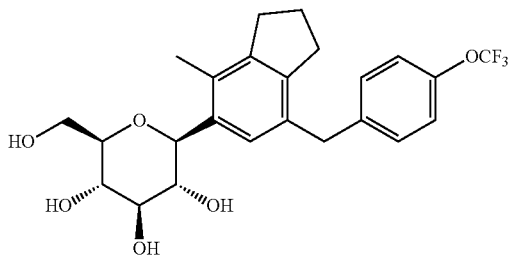 [SMILES: Cc1c([C@@H]2O[C@H](CO)[C@@H](O)[C@H](O)[C@H]2O)cc(Cc2ccc(OC(F)(F)F)cc2)c2c1CCC2]

¹H NMR (400 MHz, CD₃OD); δ 7.22 (d, J=8.4 Hz, 2H), 7.14 (s, 1H), 7.12 (d, J=8.4 Hz, 2H), 4.46 (d, J=9.2 Hz, 1H), 3.94 (s, 2H), 3.87 (d, J=12.4 Hz, 1H), 3.68-3.62 (m, 1H), 3.55-3.46 (m, 2H), 3.40-3.39 (m, 2H), 2.85 (t, J=7.6 Hz, 2H), 2.72 (d, J=7.6 Hz, 2H), 2.29 (s, 3H), 2.02-1.99 (in. 2H)

Example 11. Preparation of (2S,3R,4R,5S,6R)-2-(7-(3,4-dimethoxybenzyl)-4-methyl-2,3-dihydro-1H-inden-5-yl)-6-(hydroxymethyl)tetrahydro-2H-pyran-3,4,5-triol

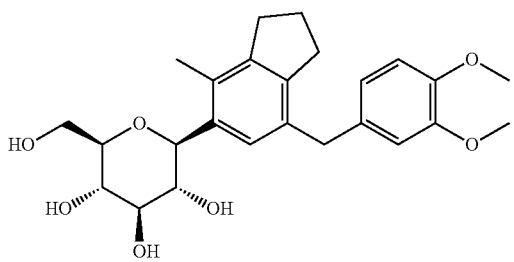 [SMILES: COc1ccc(Cc2cc([C@@H]3O[C@H](CO)[C@@H](O)[C@H](O)[C@H]3O)c(C)c3c2CCC3)cc1OC]

¹H NMR (400 MHz, CD₃OD); δ 7.12 (s, 1H), 6.81 (d, J=8.0 Hz, 1H), 6.76 (s, 1H), 6.68 (d, J=8.4 Hz, 1H), 4.45 (d, J=8.8 Hz, 1H), 3.88-3.85 (m, 3H), 3.78 (s, 3H), 3.75 (s, 3H), 3.66 (dd, J=12.0, 5.2 Hz, 1H), 3.59-3.48 (m, 2H), 3.41-3.39 (m, 2H), 2.85 (t, J=7.4 Hz, 2H), 2.76 (t, J=7.4 Hz, 2H), 2.29 (s, 3H), 2.05-1.97 (m, 2H)

Example 12. Preparation of (2S,3R,4R,5S,6R)-2-(7-(2,4-dimethoxybenzyl)-4-methyl-2,3-dihydro-1H-inden-5-yl)-6-(hydroxymethyl)tetrahydro-2H-pyran-3,4,5-triol

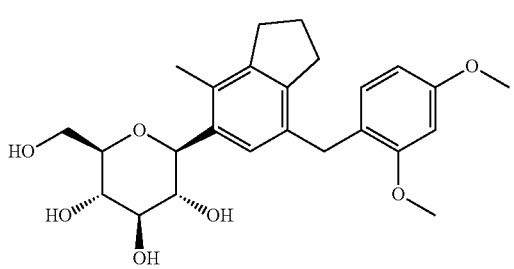 [SMILES: COc1ccc(Cc2cc([C@@H]3O[C@H](CO)[C@@H](O)[C@H](O)[C@H]3O)c(C)c3c2CCC3)c(OC)c1]

¹H NMR (400 MHz, CD₃OD); δ 7.17 (s, 1H), 6.91 (d, J=8.0 Hz, 1H), 6.60 (d, J=2.4 Hz, 1H), 6.47 (dd, J=8.4, 2.4 Hz, 1H), 4.54 (d, J=8.8 Hz, 1H), 3.97 (d, J=12.0 Hz, 1H), 3.91 (s, 3H), 3.89 (s, 2H), 3.86 (s, 3H), 3.75 (dd, J=12.0, 5.6 Hz, 1H), 3.67-3.57 (m, 2H), 3.50-3.45 (m, 2H), 2.96 (t, J=7.6 Hz, 2H), 2.87 (t, J=7.6 Hz, 2H), 2.39 (s, 3H), 2.16-2.10 (m, 2H)

Example 13. Preparation of (2R,3S,4R,5R,6S)-2-(hydroxymethyl)-6-(4-methyl-7-(4-methylthio)benzyl)-2,3-dihydro-1H-indene-5-yl)tetrahydro-2H-pyran-3,4,5-triol

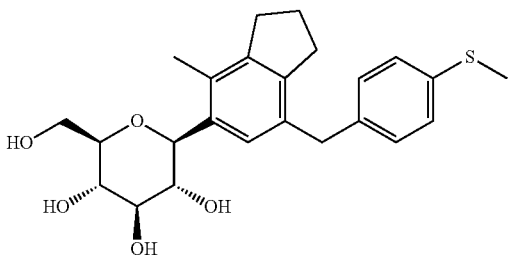

¹H NMR (400 MHz, CD₃OD); δ 7.14 (d, J=8.0 Hz, 1H), 7.11 (s, 1H), 7.07 (d, J=8.0 Hz, 2H), 4.46 (d, J=9.2 Hz, 1H), 3.87-3.86 (m, 3H), 3.67 (dd, J=11.6, 5.2 Hz, 1H), 3.59-3.48 (m, 2H), 3.41-3.39 (m, 2H), 2.85 (t, J=7.6 Hz, 2H), 2.73 (t, J=7.6 Hz, 2H), 2.42 (s, 3H), 2.29 (s, 3H), 2.04-1.96 (m, 2H)

Example 14. Preparation of (2S,3R,4R,5S,6R)-2-(7-(4-fluorobenzyl)-4-methyl-2,3-dihydro-1H-indene-5-yl)-6-(hydroxymethyl)tetrahydro-2H-pyran-3,4,5-triol

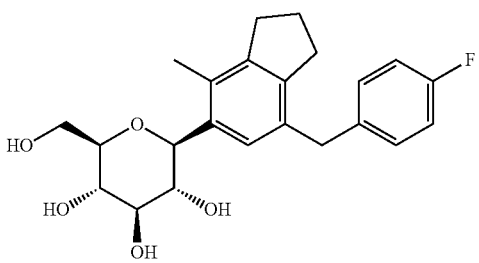 [SMILES: Cc1c([C@@H]2O[C@H](CO)[C@@H](O)[C@H](O)[C@H]2O)cc(Cc2ccc(F)cc2)c2c1CCC2]

¹H NMR (400 MHz, CD₃OD); δ 7.24-7.21 (m, 3H), 7.05-7.00 (m, 2H), 4.54 (d, J=9.2 Hz, 1H), 3.99 (s, 2H), 3.96 (d, J=12.0 Hz, 1H), 3.79-3.73 (m, 1H), 3.65-3.59 (m, 2H), 3.49-3.48 (m, 2H), 2.94 (t, J=7.6 Hz, 2H), 2.81 (t, J=7.6 Hz, 2H), 2.38 (s, 3H), 2.11-2.07 (m, 2H)

Example 15. Preparation of (2S,3R,4R,5S,6R)-2-(7-(4-fluoro-3-methylbenzyl)-4-methyl-2,3-dihydro-1H-indene-5-yl)-6-(hydroxymethyl)tetrahydro-2H-pyran-3,4,5-triol

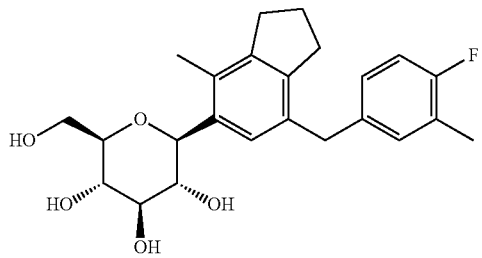 [SMILES: Cc1cc(Cc2cc([C@@H]3O[C@H](CO)[C@@H](O)[C@H](O)[C@H]3O)c(C)c3c2CCC3)ccc1F]

¹H NMR (400 MHz, CD₃OD); δ 7.12 (s, 1H), 6.99 (d, J=7.2 Hz, 1H), 6.96-6.93 (m, 1H), 6.88-6.84 (m, 1H), 4.47 (d, J=9.2 Hz, 1H), 3.90-3.86 (m, 3H), 3.68-3.64 (m, 1H), 3.61-3.49 (m, 2H), 3.42-3.40 (m, 2H), 2.86 (t, J=7.2 Hz, 2H), 2.73 (t, J=7.2 Hz, 2H), 2.30 (s, 3H), 2.19 (s, 3H), 2.03-1.99 (m, 2H)

Example 16. Preparation of (2S,3R,4R,5S,6R)-2-(7-(4-chlorobenzyl)-4-methyl-2,3-dihydro-1H-indene-5-yl)-6-(hydroxymethyl)tetrahydro-2H-pyran-3,4,5-triol

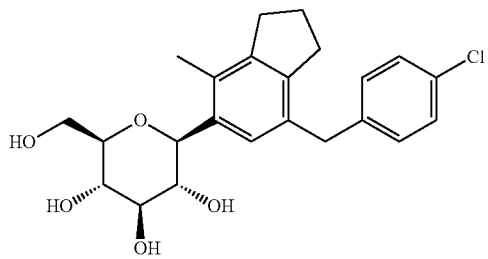 [SMILES: Cc1c([C@@H]2O[C@H](CO)[C@@H](O)[C@H](O)[C@H]2O)cc(Cc2ccc(Cl)cc2)c2c1CCC2]

¹H NMR (400 MHz, CD₃OD); δ 7.21 (d, J=8.4 Hz, 2H), 7.12 (d, J=8.4 Hz, 2H), 7.11 (s, 1H), 4.46 (d, J=8.8 Hz, 1H), 3.90-3.86 (m, 3H), 3.67 (dd, J=11.6, 5.2 Hz, 1H), 3.58-3.48 (m, 2H), 3.39-3.43 (m, 2H), 2.85 (t, J=7.6 Hz, 2H), 2.72 (t, J=7.6 Hz, 2H), 2.29 (s, 3H), 2.04-1.97 (m, 2H)

Example 17. Preparation of (2S,3R,4R,5S,6R)-2-(8-(4-ethoxybenzyl)-2,3-dihydrobenzo[b][1,4]dioxin-6-yl)-6-(hydroxymethyl)tetrahydro-2H-pyran-3,4,5-triol Step 1. Synthesis of 5-bromo-2,3-dihydro benzoic acid (17-1)

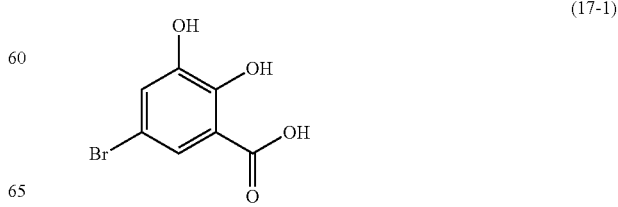

(17-1)

Br$_2$ (3.32 mL, 64.9 mmol) was added dropwise into 2,3-dihydrobenzoic acid (10.0 g, 64.9 mmol, Aldrich reagent) in AcOH (120 mL), after which a resulting mixture was stirred at room temperature for 12 hours. A reaction was completed with a saturated Na$_2$S$_2$O$_3$ aqueous solution, after which a resulting mixture was dried under reduced pressure, so as to remove a volatile substance. A resulting residue was distributed between EtOAc and water. A water layer was extracted with EtOAc, after which a combined organic layer was dried over anhydrous MgSO$_4$, filtered and concentrated under vacuum. The title compound (17-1) (14.1 g, 60.3 mmol, 93%) was used in a following step without an additional purification.

$^1$H NMR (400 MHz, CDCl$_3$); δ 7.47 (s, 1H), 7.37 (s, 1H)

Step 2. Synthesis of methyl 5-bromo-2,3-dihydro benzoate (17-2)

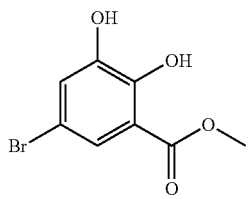

(17-2)

SOCl$_2$ (13.1 mL, 180.9 mmol) was added dropwise into a solution of the compound (17-1) (14.1 g, 60.3 mmol) in MeOH (200 mL) at 0° C. in a nitrogen atmosphere. A resulting mixture was stirred at reflux overnight. After a reaction was completed, a volatile solvent was evaporated under reduced pressure. A resulting residue was purified by means of a silica gel column chromatography, so as to obtain the title compound (17-2) (12.5 g, 50.6 mmol, 84%).

$^1$H NMR (400 MHz, CDCl$_3$); δ 10.85 (s, 1H), 7.51 (s, 1H), 7.23 (s, 1H), 5.69 (s, 1H), 3.96 (s, 3H)

Step 3. Synthesis of methyl 7-bromo-2,3-dihydrobenzo[b][1,4]dioxin-5-carboxylate (17-3)

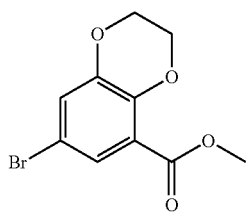

(17-3)

1,2-dibromoethane (8.2 mL, 94.9 mmol) was added dropwise into a mixture of the compound (17-2) (15.6 g, 63.3 mmol) in DMF (200 mL) as well as K$_2$CO$_3$ (26.2 g, 95.0 mmol). A reaction mixture was heated at 100° C. overnight, after which a reaction thereof was completed with water. A water layer was extracted with EtOAc, after which a combined organic layer was washed with brine, such that the resulting product was dried over anhydrous MgSO$_4$, filtered and concentrated under vacuum. A resulting residue was purified by means of a silica gel column chromatography, so as to obtain the title compound (17-3) (11.0 g, 40.4 mmol, 64%).

$^1$H NMR (400 MHz, CDCl$_3$); δ 7.52 (d, J=2.4 Hz, 1H), 7.16 (d, J=2.8 Hz, 1H), 4.37-4.28 (m, 4H), 3.88 (s, 3H).

Step 4. Synthesis of 7-bromo-2,3-dihydrobenzo[b][1,4]dioxin-5-carboxylic acid (17-4)

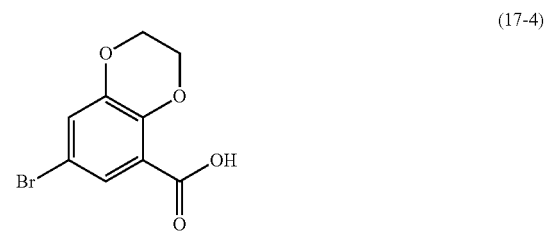 [SMILES: O=C(O)c1cc(Br)cc2c1OCCO2]

(17-4)

A 1N—NaOH aqueous solution (30.7 mL) was added into the compound (17-3) (5.0 g, 15.4 mmol) in THF/MeOH (20 mL/40 mL) at room temperature. A reaction mixture was stirred overnight at room temperature. After a reaction was completed, a volatile substance was removed under reduced pressure. A 1N—HCl aqueous solution was added into a residue to carry out acidification, during which a resulting mixture was stirred to precipitate a crude product. The crude product was filtered, washed with water and dried under high vacuum, so as to obtain the title compound (17-4) (3.4 g, 13.0 mmol, 85%).

$^1$H NMR (400 MHz, CDCl$_3$); δ 8.00 (s, 1H), 7.83 (s, 1H), 4.52-4.50 (m, 4H)

Step 5. Synthesis of 7-bromo-5-(4-ethoxybenzyl)-2,3-dihydrobenzo[b][1,4]dioxin (17-5)

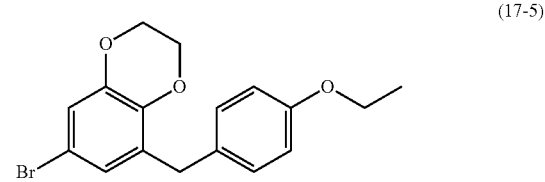 [SMILES: CCOc1ccc(Cc2cc(Br)cc3c2OCCO3)cc1]

(17-5)

The title compound (17-5) was obtained with the compound (17-4) by means of a method as shown from Steps 4 to 5 of Example 1.

$^1$H NMR (400 MHz, CDCl$_3$); δ 7.09 (d, J=8.8 Hz, 2H), 6.88 (d, J=2.4 Hz, 1H), 6.81 (d, J=8.8 Hz, 2H), 6.73 (d, J=2.4 Hz, 1H), 4.26-4.22 (m, 4H), 4.01 (q, J=7.2 Hz, 2H), 3.81 (s, 2H), 1.40 (t, J=6.8 Hz, 3H)

Step 6. Synthesis of a Target Compound

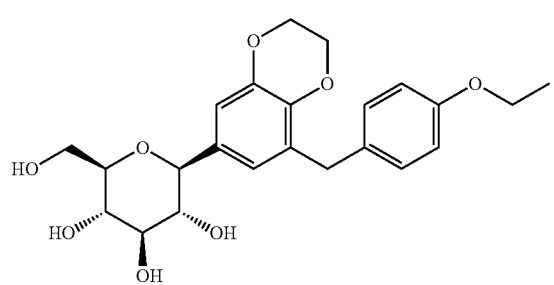

The target compound was obtained with the compound (17-5) by means of a method as shown from Steps 6 to 7 of Example 1.

¹H NMR (400 MHz, CD₃OD); δ 7.10 (d, J=8.4 Hz, 2H), 6.78-6.74 (m, 4H), 4.21 (dd, J=10.0, 4.8 Hz, 4H), 4.00-3.95 (m, 3H), 3.87-3.78 (m, 3H), 3.66 (dd, J=12.0, 5.6 Hz, 1H), 3.44-3.29 (m, 4H), 1.35 (t, J=6.8 Hz, 3H)

Example 18. Preparation of (2S,3R,4R,5S,6R)-2-(8-(4-ethylbenzyl)-2,3-dihydrobenzo[b][1,4]dioxin-6-yl)-6-(hydroxymethyl)tetrahydro-2H-pyran-3,4,5-triol Step 1. Synthesis of 7-bromo-5-(4-ethylbenzyl)-2,3-dihydrobenzo[b][1,4]dioxin (18-1)

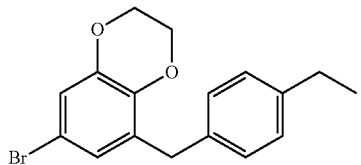

(18-1)

The title compound (18-1) was obtained with the compound (17-4) obtained in Step 4 of Example 17 by means of a method as shown from Steps 1 to 3 of Example 4.

¹H NMR (400 MHz, CDCl₃); δ 7.13-7.10 (m, 4H), 6.88 (d, J=2.0 Hz, 1H), 6.75 (d, J=2.0 Hz, 1H), 4.28-4.22 (m, 4H), 3.85 (s, 2H), 2.62 (q, J=7.6 Hz, 2H), 1.22 (t, J=7.6 Hz, 3H)

Step 2. Synthesis of a Target Compound

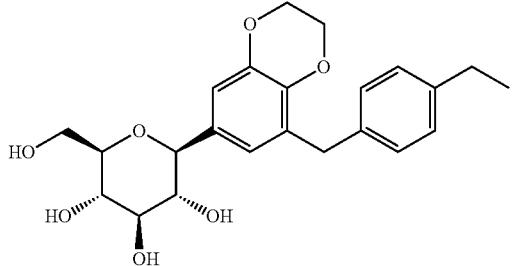 [SMILES: CCc1ccc(Cc2cc([C@@H]3O[C@H](CO)[C@@H](O)[C@H](O)[C@H]3O)cc3c2OCCO3)cc1]

The target compound was obtained with the compound (18-1) by means of a method as shown in Step 4 of Example 4.

¹H NMR (400 MHz, CD₃OD); δ 7.10 (d, J=7.6 Hz, 2H), 7.05 (d, J=8.0 Hz, 2H), 6.78 (d, J=2.0 Hz, 1H), 6.75 (d, J=2.0 Hz, 1H), 4.24-4.20 (m, 4H), 3.96 (d, J=9.2 Hz, 1H), 3.91-3.81 (m, 4H), 3.66 (dd, J=12.0, 5.6 Hz, 1H), 3.42-3.32 (m, 3H), 2.58 (q, J=7.6 Hz, 2H), 1.19 (t, J=7.6 Hz, 3H)

Example 19. Preparation of (2R,3S,4R,5R,6S)-2-(hydroxymethyl)-6-(7-(4-methoxybenzyl)benzo[d][1,3]dioxol-5-yl)tetrahydro-2H-pyran-3,4,5-triol Step 1. Synthesis of methyl 6-bromobenzo[d][1,3]dioxol-4-carboxylate (19-1)

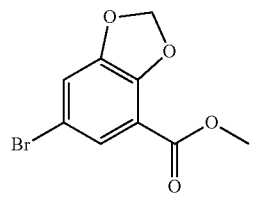

(19-1)

Dibromomethane (3.2 mL, 45.3 mmol) was added dropwise into a mixture of the compound (17-2) (7.5 g, 30.2 mmol) obtained in Step 2 of Example 17 in DMF (100 mL) as well as K₂CO₃ (12.5 g, 95.0 mmol). A reaction mixture was heated at 100° C. overnight, after which a reaction thereof was completed with water. A water layer was extracted with EtOAc, after which a combined organic layer was washed with brine, such that the resulting product was dried over anhydrous MgSO₄, filtered and concentrated under vacuum. A resulting residue was purified by means of a silica gel column chromatography, so as to obtain the title compound (19-1) (7.6 g, 29.3 mmol, 97%).

¹H NMR (400 MHz, CDCl₃); δ 7.55 (d, J=2.0 Hz, 1H), 7.08 (d, J=1.6 Hz, 1H), 6.12 (s, 2H), 3.92 (s, 3H)

Step 2. Synthesis of 6-bromobenzo[d][1,3]dioxol-4-carboxylic acid (19-2)

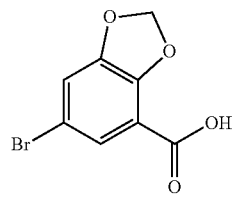

(19-2)

A 1N—NaOH aqueous solution (58.7 mL) was added into the compound (19-1) (7.6 g, 29.3 mmol) in THF/MeOH (40 mL/80 mL) at room temperature. A reaction mixture was stirred at room temperature for 4 hours. After a reaction was completed, a volatile substance was removed under reduced pressure. A 1N—HCl aqueous solution was added into a residue to carry out acidification, during which a resulting mixture was stirred to precipitate a crude product. The crude product was filtered, washed with water and dried under high vacuum, so as to obtain the title compound (19-2) (7.2 g, 29.3 mmol, 99%).

¹H NMR (400 MHz, CDCl₃); δ 7.59 (d, J=2.0 Hz, 1H), 7.13 (d, J=2.0 Hz, 1H), 6.16 (s, 2H).

Step 3. Synthesis of 6-bromo-4-(4-methoxybenzyl)benzo[d][1,3]dioxol (19-3)

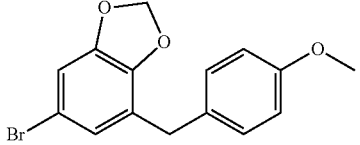
(19-3)

The title compound (19-3) was obtained with the compound (19-2) by means of a method as shown from Steps 4 to 5 of Example 1.

$^1$H NMR (400 MHz, CDCl$_3$); δ 7.13 (d, J=8.8 Hz, 2H), 6.85-6.81 (m, 3H), 6.75 (s, 1H), 5.96 (s, 2H), 3.81 (s, 2H), 3.79 (s, 3H)

Step 4. Synthesis of a Target Compound

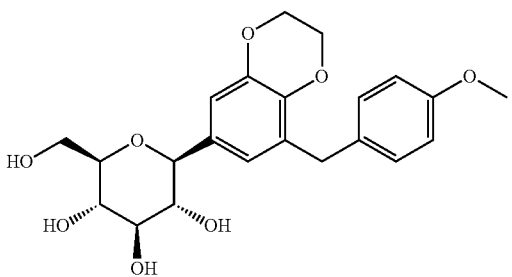 [SMILES: COc1ccc(Cc2cc([C@@H]3O[C@H](CO)[C@@H](O)[C@H](O)[C@H]3O)cc3c2OCCO3)cc1]

The target compound was obtained with the compound (19-3) by means of a method as shown in Step 4 of Example 4.

$^1$H NMR (400 MHz, CD$_3$OD); δ 7.14 (d, J=8.4 Hz, 2H), 6.81-6.79 (m, 3H), 6.73 (s, 1H), 5.92 (s, 2H), 4.00 (d, J=9.2 Hz, 1H), 3.87-3.82 (m, 4H), 3.75 (s, 3H), 3.69-3.64 (m, 1H), 3.42-3.32 (m, 3H)

Example 20. Preparation of (2R,3S,4R,5R,6S)-2-(hydroxymethyl)-6-(7-(4-(methylthio)benzyl)benzo[d][1,3]dioxol-5-yl)tetrahydro-2H-pyran-3,4,5-triol

Step 1. Synthesis of 6-bromo-4-(4-methylthio)benzyl)benzo[d][1,3]dioxol (20-1)

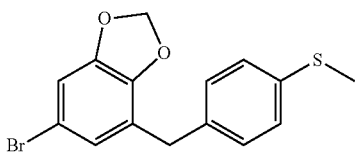
(20-1)

The title compound (20-1) was obtained with the compound (19-2) obtained in Step 2 of Example 18 by means of a method as shown from Steps 1 to 3 of Example 4.

$^1$H NMR (400 MHz, CDCl$_3$); δ 7.20 (d, J=8.0 Hz, 2H), 7.14 (d, J=8.4 Hz, 2H), 6.83 (s, 1H), 6.76 (s, 1H), 5.97 (s, 2H), 3.83 (s, 2H), 2.47 (s, 3H)

Step 2. Synthesis of a Target Compound

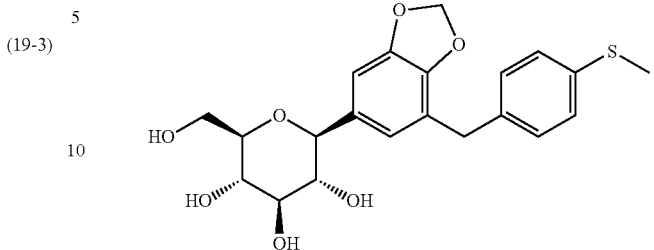

The target compound was obtained with the compound (20-1) by means of a method as shown in Step 4 of Example 4.

$^1$H NMR (400 MHz, CD$_3$OD); δ 7.16 (s, 4H), 6.80 (s, 1H), 6.75 (s, 1H), 5.93 (s, 2H), 4.00 (d, J=9.2 Hz, 1H), 3.86-3.84 (m, 3H), 3.69-3.64 (m, 1H), 3.43-3.28 (m, 4H), 2.43 (s, 3H)

Example 21. Preparation of (2S,3R,4R,5S,6R)-2-(7-(4-ethylbenzyl)benzo[d][1,3]dioxol-5-yl)-6-(hydroxymethyl)tetrahydro-2H-pyran-3,4,5-triol

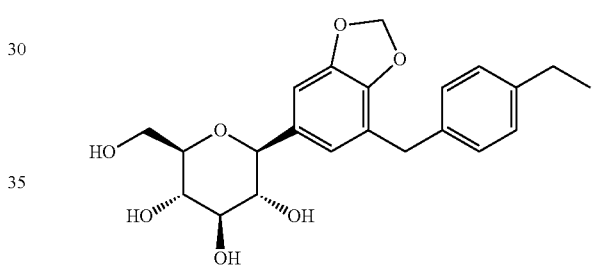

The target compound was obtained by means of a method as shown in Example 20.

$^1$H NMR (400 MHz, CD$_3$OD); δ 7.13 (d, J=8.0 Hz, 2H), 7.07 (d, J=7.6 Hz, 2H), 6.79 (s, 1H), 6.75 (s, 1H), 5.92 (s, 2H), 4.00 (d, J=9.2 Hz, 1H), 3.90-3.81 (m, 3H), 3.67 (dd, J=12.0, 5.6 Hz, 1H), 3.45-3.29 (m, 4H), 2.58 (q, J=7.6 Hz, 2H), 1.19 (t, J=7.6 Hz, 3H)

Example 22. Preparation of (2S,3R,4R,5S,6R)-2-(4-(4-ethoxybenzyl)-5,6,7,8-tetrahydronaphthalene-2-yl)-6-(hydroxymethyl)tetrahydro-2H-pyran-3,4,5-triol

Step 1. Synthesis of methyl 5,6,7,8-tetrahydronaphthalene-1-carboxylate (22-1)

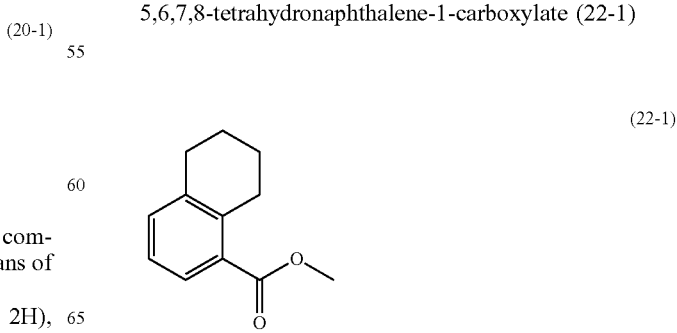
(22-1)

SOCl$_2$ (4.1 mL, 56.7 mmol) was added dropwise into a solution of 5,6,7,8-tetrahydronaphthalene-1-carboxylic acid (2.0 g, 11.3 mmol, TCI reagent) in MeOH (30 mL) at 0° C. in a nitrogen atmosphere. A resulting mixture was stirred at reflux overnight. After a reaction was completed, a volatile solvent was evaporated under reduced pressure. A resulting residue was purified by means of a silica gel column chromatography, so as to obtain the title compound (22-1) (1.98 g, 10.4 mmol, 92%).

$^1$H NMR (400 MHz, CDCl$_3$); δ 7.64 (d, J=7.6 Hz, 1H), 7.21 (d, J=7.2 Hz, 1H), 7.13 (t, J=7.6 Hz, 1H), 3.87 (s, 3H), 3.06-3.03 (m, 2H), 2.83-2.79 (m, 2H), 1.80-1.77 (m, 4H)

Step 2. Synthesis of methyl 3-bromo-5,6,7,8-tetra-hydronaphthalene-1-carboxylate (22-2)

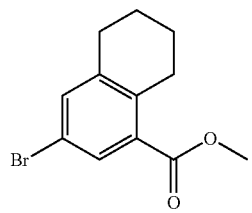

(22-2)

A concentrated HNO$_3$ (0.4 mL, 8.91 mmole) and Br$_2$ (3.32 mL, 64.9 mmol) were added dropwise into a solution mixed with the compound (22-1) (1.13 g, 5.94 mmol) in AcOH (10 mL) as well as AgNO$_3$ (1.51 g, 8.91 mmol) in water (5 mL), after which a resulting mixture was stirred at room temperature for 12 hours. A reaction was completed with a saturated Na$_2$S$_2$O$_3$ aqueous solution, after which a resulting mixture was dried under reduced pressure to remove a volatile substance. A resulting residue was distributed between EtOAc and water. A water layer was extracted with EtOAc, after which a combined organic layer was dried over anhydrous MgSO$_4$, filtered and concentrated under vacuum. A resulting residue was purified by means of a silica gel column chromatography, so as to obtain the title compound (22-2) (1.41 g, 5.24 mmol, 88%).

$^1$H NMR (400 MHz, CDCl$_3$); δ 7.78 (d, J=1.6 Hz, 1H), 7.36 (s, 1H), 3.87 (s, 3H), 2.99-2.96 (m, 2H), 2.81-2.77 (m, 2H), 1.81-1.74 (m, 4H)

Step 3. Synthesis of 3-bromo-5,6,7,8-tetrahydronaphthalene-1-carboxylic acid (22-3)

LiOH.H$_2$O (0.67 g, 15.7 mmol) was added into the compound (22-2) (1.41 g, 5.24 mmol) in THF/MeOH/water (15 mL/5 mL/5 mL) at room temperature. A reaction mixture was stirred overnight at room temperature. After a reaction was completed, a volatile substance was removed under reduced pressure. A 1N—HCl aqueous solution was added into a residue to carry out acidification, during which a resulting mixture was stirred to precipitate a crude product. The crude product was filtered, washed with water and dried under high vacuum, so as to obtain the title compound (22-3) (1.31 g, 5.14 mmol, 98%).

$^1$H NMR (400 MHz, CD$_3$OD); δ 7.72 (s, 1H), 7.39 (s, 1H), 3.06-3.01 (m, 2H), 2.86-2.80 (m, 2H), 1.83-1.74 (m, 4H)

Step 4. Synthesis of 7-bromo-5-(4-ethoxybenzyl)-1,2,3,4-tetrahydronaphthalene (22-4)

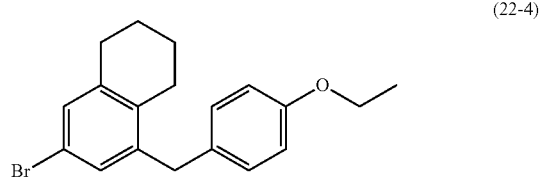 [SMILES: CCOc1ccc(Cc2cc(Br)cc3c2CCCC3)cc1]

(22-4)

The title compound (22-4) was obtained with the compound (22-3) by means of a method as shown from Steps 4 to 5 of Example 1.

$^1$H NMR (400 MHz, CDCl$_3$); δ 7.12 (s, 1H), 7.03-6.98 (m, 3H), 6.81 (d, J=8.8 Hz, 2H), 4.01 (q, J=7.2 Hz, 2H), 3.82 (t, J=5.6 Hz, 2H), 2.74 (t, J=5.6 Hz, 2H), 2.53 (t, J=6.0 Hz, 2H), 1.73-1.70 (m, 4H), 1.40 (t, J=7.2 Hz, 3H)

Step 5. Synthesis of a Target Compound

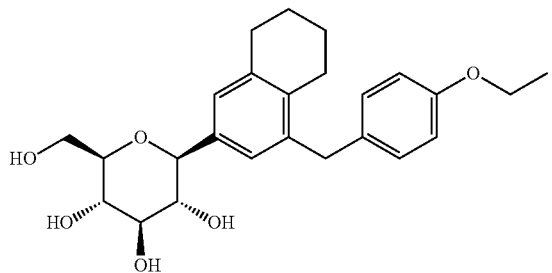 [SMILES: CCOc1ccc(Cc2cc([C@@H]3O[C@H](CO)[C@@H](O)[C@H](O)[C@H]3O)cc3c2CCCC3)cc1]

The target compound was obtained with the compound (22-4) by means of a method as shown from Steps 6 to 7 of Example 1.

$^1$H NMR (400 MHz, CD$_3$OD); δ 7.02-6.99 (m, 4H), 6.77 (d, J=8.4 Hz, 2H), 4.04 (d, J=9.6 Hz, 1H), 3.97 (q, J=6.8 Hz, 2H), 3.89-3.87 (m, 3H), 3.69 (dd, J=12.0, 5.2 Hz, 1H), 3.46-3.36 (m, 4H), 2.78-2.76 (m, 2H), 2.56-2.54 (m, 2H), 1.73-1.34 (m, 4H), 1.35 (t, J=6.8 Hz, 3H)

Example 23. Preparation of (2S,3R,4R,5S,6R)-2-(4-(4-ethylbenzyl)-5,6,7,8-tetrahydronaphthalene-2-yl)-6-(hydroxymethyl)tetrahydro-2H-pyran-3,4,5-triol Step 1. Synthesis of 7-bromo-5-(4-ethylbenzyl)-1,2,3,4-tetrahydronaphthalene (23-1)

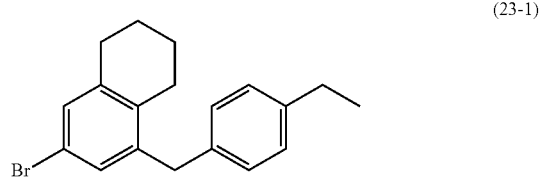 [SMILES: CCc1ccc(Cc2cc(Br)cc3c2CCCC3)cc1]

(23-1)

The title compound (23-1) was obtained with the compound (22-3) obtained in Step 3 of Example 22 by means of a method as shown from Steps 1 to 3 of Example 4.

¹H NMR (400 MHz, CDCl₃); δ 7.12-7.10 (m, 3H), 7.05 (s, 1H), 7.01 (d, J=8.4 Hz, 2H), 3.85 (s, 2H), 2.73 (t, J=6.4 Hz, 2H), 2.62 (q, J=7.6 Hz, 2H), 2.53 (t, J=6.0 Hz, 2H), 1.78-1.70 (m, 4H), 1.22 (t, J=7.6 Hz, 3H)

Step 2. Synthesis of a Target Compound

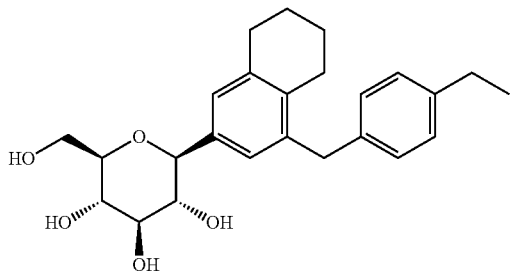 [SMILES: CCc1ccc(Cc2cc([C@@H]3O[C@H](CO)[C@@H](O)[C@H](O)[C@H]3O)cc3c2CCCC3)cc1]

The target compound was obtained with the compound (23-1) by means of a method as shown in Step 4 of Example 4.

¹H NMR (400 MHz, CD₃OD); δ 7.06-6.99 (m, 6H), 4.03 (d, J=9.2 Hz, 1H), 3.89-3.85 (m, 3H), 3.69-3.67 (m, 1H), 3.45-3.34 (m, 4H), 2.76 (s, 2H), 2.60-2.55 (m, 4H), 1.71 (s, 4H), 1.18 (t, J=7.6 Hz, 3H)

Example 24. Preparation of (2R,3S,4R,5R,6S)-2-(hydroxymethyl)-6-(4-(4-methoxybenzyl)-1-methyl-5,6,7,8-tetrahydronaphthalen-2-yl)tetrahydro-2H-pyran-3,4,5-triol Step 1. Synthesis of ethyl 4-methyl-5,6,7,8-tetrahydronaphthalene-1-carboxylate (24-1)

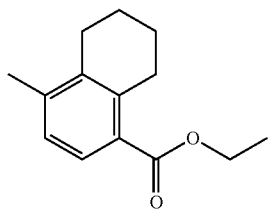

(24-1)

A mixture of ethyl sorbate (49.5 mL, 0.33 mol, TCI reagent) in xylene (330 mL) as well as 1-pyrrolidino-1-cyclohexene (50.24 g, 0.33 mol, TCI agent) was stirred at reflux overnight. After a reaction was completed, a volatile solvent was evaporated under reduced pressure. EtOAc was added into the resulting mixture. An organic layer was washed with brine, after which the resulting product was dried over anhydrous MgSO₄, filtered and concentrated under vacuum. A crude compound was used in a following step without an additional purification. S₈ (10.7 g, 0.33 mol) was added into the crude compound. A reaction mixture was stirred at 250° C. for 2 hours. After a reaction was completed, the resulting mixture was distilled under reduced pressure, so as to obtain the title compound (24-1) (24.7 g, 0.11 mol, 34%).

¹H NMR (400 MHz, CDCl₃); δ 7.58 (d, J=7.6 Hz, 1H), 7.02 (d, J=8.0 Hz, 1H), 4.32 (q, J=7.2 Hz, 2H), 3.06 (t, J=6.4 Hz, 2H), 2.64 (t, J=6.4 Hz, 2H), 2.24 (s, 3H), 1.85-1.73 (m, 4H), 1.37 (t, J=7.2 Hz, 3H)

Step 2. Synthesis of ethyl 3-bromo-4-methyl-5,6,7,8-tetrahydronaphthalene-1-carboxylate (24-2)

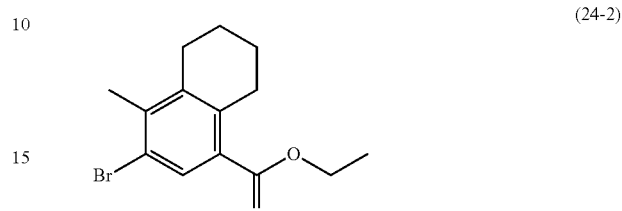

(24-2)

Br₂ (3.5 mL, 68.6 mmol) and AgNO₃ (11.64 g, 68.6 mmol) in water (60 mL) were added dropwise into a mixture of the compound (24-1) (11.5 g, 68.6 mmol) in AcOH (450 mL) as well as a concentrated HNO₃ (5.2 mL) at room temperature. A resulting mixture was stirred overnight at room temperature. A reaction was completed with saturated Na₂S₂O₃ solution, so as to perform an extraction with EtOAc. An organic layer was dried over anhydrous MgSO₄, filtered and concentrated under vacuum. A crude compound (24-2) was used in a following step without an additional purification.

¹H NMR (400 MHz, CDCl₃); δ 7.87 (s, 1H), 4.32 (q, J=7.2 Hz, 2H), 3.00 (t, J=6.4 Hz, 2H), 2.70 (t, J=6.4 Hz, 2H), 2.36 (s, 3H), 1.82-1.71 (m, 4H), 1.38 (t, J=7.2 Hz, 3H).

Step 3. Synthesis of 3-bromo-4-methyl-5,6,7,8-tetrahydronaphthalene-1-carboxylic acid (24-3)

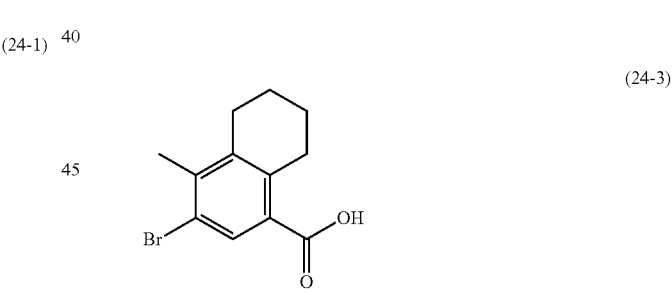

(24-3)

LiOH.H₂O (3.6 g, 86.2 mmol) was added into a solution of the compound (24-2) (12.8 g, 43.1 mmol) in THF/MeOH/water (150 mL/50 mL/50 mL) at room temperature. A reaction mixture was stirred overnight at room temperature. After a reaction was completed, a volatile substance was removed under reduced pressure. A 1N—HCl aqueous solution was added into a residue to carry out acidification, during which a resulting mixture was stirred to precipitate a crude product. The crude product was filtered, washed with water and dried under high vacuum, so as to obtain the title compound (24-3) (9.3 g, 34.4 mmol, 80%).

¹H NMR (400 MHz, CDCl₃); δ 8.07 (s, 1H), 3.07 (t, J=6.4 Hz, 2H), 2.71 (t, J=6.4 Hz, 2H), 2.39 (s, 3H), 1.83-1.72 (m, 4H).

Step 4. Synthesis of 6-bromo-8-(4-methoxybenzyl)-5-methyl-1,2,3,4-tetrahydronaphthalene (24-4)

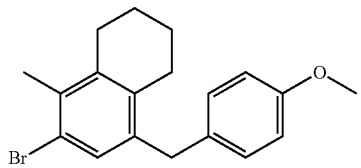
(24-4)

The title compound (24-4) was obtained with the compound (24-3) by means of a method as shown from Steps 4 to 5 of Example 1.

¹H NMR (400 MHz, CDCl₃); δ 7.16 (s, 1H), 7.02 (d, J=8.8 Hz, 2H), 6.82 (d, J=8.0 Hz, 2H), 3.82 (s, 2H), 3.79 (s, 3H), 2.67 (t, J=6.4 Hz, 2H), 2.54 (t, J=6.4 Hz, 2H), 2.31 (s, 3H), 1.77-1.68 (m, 4H).

Step 5. Synthesis of a Target Compound

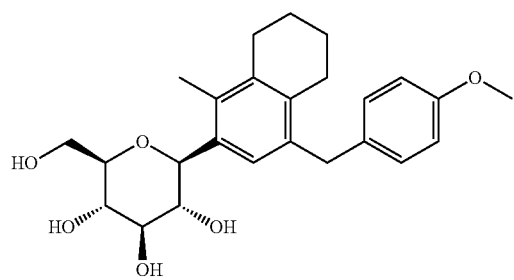 [SMILES: COc1ccc(Cc2cc([C@@H]3O[C@H](CO)[C@@H](O)[C@H](O)[C@H]3O)c(C)c3c2CCCC3)cc1]

The target compound was obtained with the compound (24-4) by means of a method as shown from Steps 6 to 7 of Example 1.

¹H NMR (400 MHz, CD₃OD); δ 7.13 (s, 1H), 7.00 (d, J=9.2 Hz, 2H), 6.77 (d, J=8.4 Hz, 1H), 4.51 (d, J=9.6 Hz, 1H), 3.89-3.85 (m, 3H), 3.73 (s, 3H), 3.67 (dd, J=11.6, 5.6 Hz, 1H), 3.60 (t, J=8.8 Hz, 1H), 3.51 (t, J=8.8 Hz, 1H), 3.41-3.39 (m, 2H), 2.65 (t, J=6.4 Hz, 2H), 2.54 (t, J=6.0 Hz, 2H), 2.24 (s, 3H), 1.75-1.64 (m, 4H)

Example 25. Preparation of (2R,3S,4R,5R,6S)-2-(hydroxymethyl)-6-(1-methyl-4-(4-methylbenzyl)-5,6,7,8-tetrahydronaphthalene-2-yl)tetrahydro-2H-pyran-3,4,5-triol Step 1. Synthesis of 6-bromo-5-methyl-8-(4-methylbenzyl)-1,2,3,4-tetrahydronaphthalene (25-1)

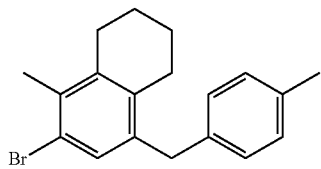
(25-1)

The title compound (25-1) was obtained with the compound (24-3) obtained in Step 3 of Example 24 by means of a method as shown from Steps 1 to 3 of Example 4.

¹H NMR (400 MHz, CDCl₃); δ 7.17 (s, 1H), 7.08 (d, J=7.6 Hz, 2H), 6.99 (d, J=8.0 Hz, 2H), 3.84 (s, 2H), 2.67 (t, J=6.4 Hz, 2H), 2.54 (t, J=6.4 Hz, 2H), 2.31 (s, 6H), 1.76-1.68 (m, 4H)

Step 2. Synthesis of a Target Compound

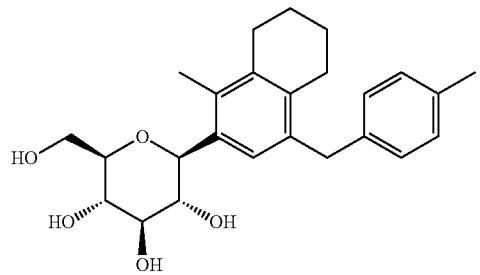 [SMILES: Cc1ccc(Cc2cc([C@@H]3O[C@H](CO)[C@@H](O)[C@H](O)[C@H]3O)c(C)c3c2CCCC3)cc1]

The target compound was obtained with the compound (25-1) by means of a method as shown in Step 4 of Example 4.

¹H NMR (400 MHz, CD₃OD); δ 7.13 (s, 1H), 7.02 (d, J=7.6 Hz, 2H), 6.97 (d, J=8.4 Hz, 2H), 4.51 (d, J=9.6 Hz, 1H), 3.86-3.89 (m, 3H), 3.67 (dd, J=11.6, 6.0 Hz, 1H), 3.60 (t, J=9.2 Hz, 1H), 3.51 (t, J=8.8 Hz, 1H), 3.42-3.40 (m, 2H), 2.65 (t, J=6.4 Hz, 2H), 2.54 (t, J=6.4 Hz, 2H), 2.26 (s, 3H), 2.24 (s, 3H), 1.75-1.64 (m, 4H)

Examples 26 to 29

Target compounds of Examples 26 to 29 were obtained by means of a method as shown in Example 25.

Example 26. Preparation of (2R,3S,4R,5R,6S)-2-(hydroxymethyl)-6-(1-methyl-4-(4-trifluoromethyl)benzyl)-5,6,7,8-tetrahydronaphthalene-2-yl)tetrahydro-2H-pyran-3,4,5-triol

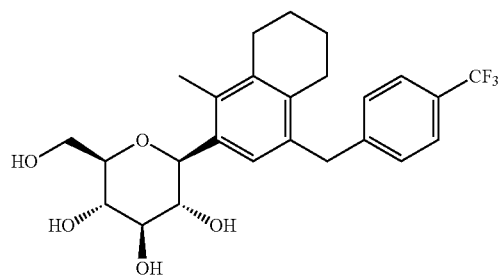 [SMILES: Cc1c([C@@H]2O[C@H](CO)[C@@H](O)[C@H](O)[C@H]2O)cc(Cc2ccc(C(F)(F)F)cc2)c2c1CCCC2]

¹H NMR (400 MHz, CD₃OD); δ 7.51 (d, J=7.6 Hz, 2H), 7.29 (d, J=8.0 Hz, 2H), 7.18 (s, 1H), 4.52 (d, J=9.2 Hz, 1H), 4.03 (s, 2H), 3.87 (dd, J=11.6, 5.6 Hz, 1H), 3.69-3.65 (m, 1H), 3.59 (t, J=8.8 Hz, 1H), 3.52 (t, J=8.8 Hz, 1H), 3.42-3.40 (m, 2H), 2.66 (t, J=6.0 Hz, 2H), 2.51 (t, J=5.6 Hz, 2H), 2.25 (s, 3H), 1.76-1.65 (m, 4H)

Example 27. Preparation of (2R,3S,4R,5R,6S)-2-(hydroxymethyl)-6-(1-methyl-4-(4-trifluoromethoxy)benzyl)-5,6,7,8-tetrahydronaphthalene-2-yl)tetrahydro-2H-pyran-3,4,5-triol

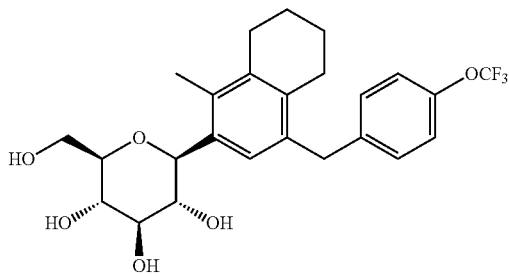 [SMILES: Cc1c([C@@H]2O[C@H](CO)[C@@H](O)[C@H](O)[C@H]2O)cc(Cc2ccc(OC(F)(F)F)cc2)c2c1CCCC2]

¹H NMR (400 MHz, CD₃OD); δ 7.19 (d, J=8.4 Hz, 2H), 7.16 (s, 1H), 7.12 (d, J=8.4 Hz, 2H), 4.52 (d, J=9.6 Hz, 1H), 3.97 (s, 2H), 3.87 (dd, J=11.6, 2.0 Hz, 1H), 3.67 (dd, J=11.6, 5.6 Hz, 1H), 3.58 (t, J=9.2 Hz, 1H), 3.51 (t, J=7.6 Hz, 1H), 3.42-3.40 (m, 2H), 2.66 (t, J=6.0 Hz, 2H), 2.53 (t, J=6.0 Hz, 2H), 2.25 (s, 3H), 1.76-1.66 (m, 4H)

Example 28. Preparation of (2R,3S,4R,5R,6S)-2-(hydroxymethyl)-6-(1-methyl-4-(4-(methylthio)benzyl)-5,6,7,8-tetrahydronaphthalene-2-yl)tetrahydro-2H-pyran-3,4,5-triol

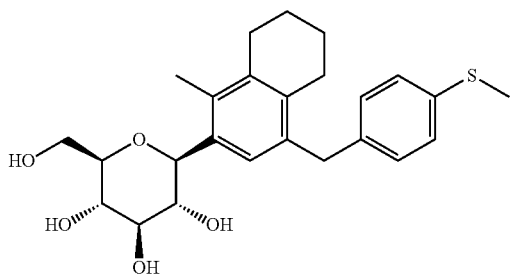

¹H NMR (400 MHz, CD₃OD); δ 7.14 (d, J=8.0 Hz, 2H), 7.14 (s, 1H), 7.04 (d, J=8.4 Hz, 2H), 4.51 (d, J=9.6 Hz, 1H), 3.86-3.90 (m, 3H), 3.67 (dd, J=11.6, 5.6 Hz, 1H), 3.59 (t, J=9.2 Hz, 1H), 3.51 (t, J=8.8 Hz, 1H), 3.39-3.41 (m, 2H), 2.66 (t, J=6.0 Hz, 2H), 2.54 (t, J=5.6 Hz, 2H), 2.42 (s, 3H), 2.25 (s, 3H), 1.75-1.65 (m, 4H)

Example 29. Preparation of (2S,3R,4R,5S,6R)-2-(4-(4-chlorobenzyl)-1-methyl-5,6,7,8-tetrahydronaphthalene-2-yl)-6-(hydroxymethyl)tetrahydro-2H-pyran-3,4,5-triol

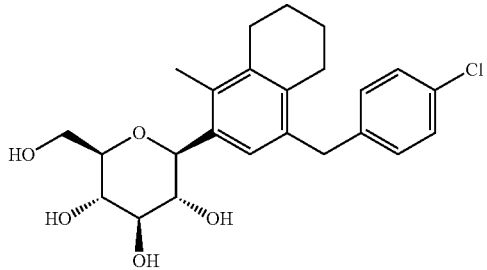 [SMILES: Cc1c([C@@H]2O[C@H](CO)[C@@H](O)[C@H](O)[C@H]2O)cc(Cc2ccc(Cl)cc2)c2c1CCCC2]

¹H NMR (400 MHz, CD₃OD); δ 7.20 (d, J=8.4 Hz, 2H), 7.14 (s, 1H), 7.08 (d, J=8.8 Hz, 2H), 4.51 (d, J=9.6 Hz, 1H), 3.92 (s, 2H), 3.87 (dd, J=11.6, 2.0 Hz, 1H), 3.67 (dd, J=11.6, 5.6 Hz, 1H), 3.59 (t, J=9.2 Hz, 1H), 3.52 (t, J=8.8 Hz, 1H), 3.42-3.40 (m, 2H), 2.66 (t, J=6.0 Hz, 2H), 2.52 (t, J=6.0 Hz, 2H), 2.25 (s, 3H), 1.76-1.65 (m, 4H)

Example 30. Preparation of (2R,3S,4R,5R,6S)-2-(hydroxymethyl)-6-(7-(4-methoxybenzyl)-4-methyl-2,3-dihydrobenzofuran-5-yl)tetrahydro-2H-pyran-3,4,5-triol Step 1. Synthesis of methyl 2-hydroxy-4-methylbenzoate (30-1)

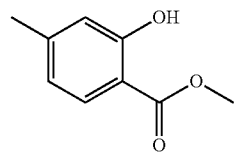

(30-1)

SOCl₂ (10.9 mL, 150 mmol) was added dropwise into a solution of 4-methylsalicylic acid (5.0 g, 32.9 mmol, TCI reagent) in MeOH (80 mL) at 0° C. in a nitrogen atmosphere. A resulting mixture was stirred at reflux overnight. After a reaction was completed, a volatile solvent was evaporated under reduced pressure. A resulting residue was purified by means of a silica gel column chromatography, so as to obtain the title compound (30-1) (5.18 g, 31.2 mmol, 95%).
¹H NMR (400 MHz, CDCl₃); δ 10.70 (s, 1H), 7.71 (d, J=8.0 Hz, 1H), 6.79 (s, 1H), 6.69 (d, J=8.4 Hz, 1H), 3.93 (s, 3H), 2.34 (s, 3H)

Step 2. Synthesis of methyl 2-(allyloxy)-4-methylbenzoate (30-2)

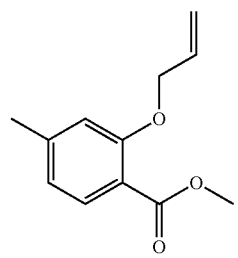

(30-2)

Allyl bromide (3.2 mL, 37.4 mmol) was added dropwise into a mixture of the compound (30-1) (5.18 g, 31.2 mmol) in DMF (40 mL) as well as K₂CO₃ (5.17 g, 37.4 mmol). A reaction mixture was stirred overnight at room temperature, after which a reaction thereof was completed with water. A water layer was extracted with EtOAc, after which a combined organic layer was washed with brine, such that the resulting product was dried over anhydrous MgSO₄, filtered and concentrated under vacuum. A resulting residue was purified by means of a silica gel column chromatography, so as to obtain the title compound (30-2) (6.35 g, 30.8 mmol, 99%).

¹H NMR (400 MHz, CDCl₃); δ 7.73 (d, J=8.0 Hz, 1H), 6.79 (d, J=8.4 Hz, 1H), 6.76 (s, 1H), 6.15-6.02 (m, 1H), 5.53 (dd, J=17.2, 1.6 Hz, 1H), 5.30 (dd, J=10.4, 1.6 Hz, 1H), 4.61 (dd, J=3.2, 1.6 Hz, 2H), 3.88 (s, 3H), 2.36 (s, 3H)

Step 3. Synthesis of methyl 3-allyl-2-hydroxy-4-methylbenzoate (30-3)

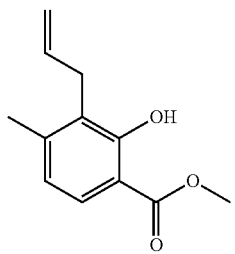

(30-3)

The compound (30-2) (6.65 g, 32.2 mmol) was stirred in a microwave reactor at 250° C. for 1 hour. A crude compound (30-3) was used in a following step without an additional purification.

¹H NMR (400 MHz, CDCl₃); δ 11.07 (s, 1H), 7.63 (d, J=8.4 Hz, 1H), 6.71 (d, J=8.4 Hz, 1H), 5.99-5.88 (m, 1H), 4.99 (dd, J=10.0, 1.6 Hz, 1H), 4.93 (dd, J=17.2, 2.0 Hz, 1H), 3.93 (s, 3H), 3.46 (dt, J=5.6, 1.6 Hz, 2H), 2.32 (s, 3H)

Step 4. Synthesis of methyl 2-hydroxy-4-methyl-3-(2-oxoethyl)benzoate (30-4)

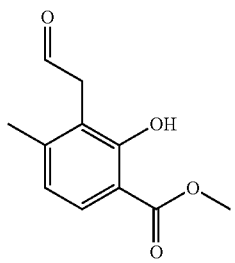

(30-4)

N-methylmorpholine N-oxide (3.51 g, 30.0 mmol) and OsO₄ (1.3 mL, 0.200 mmol, 4 wt % in H₂O) were added into a solution of the compound (30-3) (2.06 g, 10.0 mmol) in THF/water (24 mL/8 mL) in a nitrogen atmosphere. After stirring a resulting reaction mixture at room temperature for 8 hours, a reaction with a reactant was completed with a saturated Na₂S₂O₃ aqueous solution, so as to perform an extraction of the resulting mixture with EtOAc. An organic layer was dried over anhydrous MgSO₄, filtered and concentrated under vacuum, so as to obtain a crude intermediate, which was used without an additional purification. NaIO₄ (10.7 g, 50.0 mmol) was added into a crude intermediate solution in THF/water (48 mL/16 mL) at room temperature in a nitrogen atmosphere. After stirring a resulting reaction mixture at room temperature for 5 hours, a reaction with a reactant was completed with a saturated Na₂S₂O₃ aqueous solution, so as to perform an extraction of the resulting mixture with EtOAc. An organic layer was dried over anhydrous MgSO₄, filtered and concentrated under vacuum, after which a resulting concentrate was purified by means of a silica gel column chromatography, so as to obtain the title compound (30-4) (2.00 g, 9.61 mmol, 96%).

¹H NMR (400 MHz, CDCl₃); δ 11.16 (s, 1H), 9.70 (t, J=1.6 Hz, 1H), 7.71 (d, J=8.0 Hz, 1H), 6.77 (d, J=8.0 Hz, 1H), 3.95 (s, 3H), 3.81 (s, 2H), 2.29 (s, 3H)

Step 5. Synthesis of methyl 2-hydroxy-3-(2-hydroxyethyl)-4-methylbenzoate (30-5)

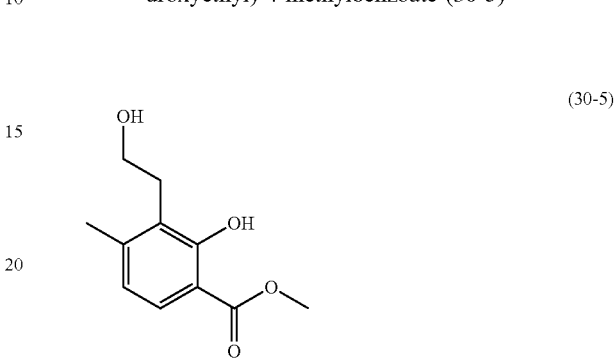

(30-5)

NaBH₄ (436 mg, 11.5 mmol) was added into a solution of the compound (30-4) (2.00 g, 9.61 mmol) in EtOH (30 mL) at 0° C. in a nitrogen atmosphere. After stirring a resulting reaction mixture at 0° C. for 1 hour, a reaction with a reactant was completed with a saturated NH₄Cl aqueous solution, so as to perform an extraction of the resulting mixture with EtOAc. An organic layer was dried over anhydrous MgSO₄, filtered and concentrated under vacuum. A resulting residue was purified by means of a silica gel column chromatography, so as to obtain the title compound (30-5) (1.82 g, 9.04 mmol, 94%).

¹H NMR (400 MHz, CDCl₃); δ 11.19 (s, 1H), 7.63 (d, J=8.4 Hz, 1H), 6.73 (d, J=8.4 Hz, 1H), 3.94 (s, 3H), 3.84 (dd, J=12.0, 6.4 Hz, 2H), 3.01 (t, J=6.4 Hz, 2H), 2.37 (s, 3H)

Step 6. Synthesis of methyl 4-methyl-2,3-dihydrobenzofuran-7-carboxylate (30-6)

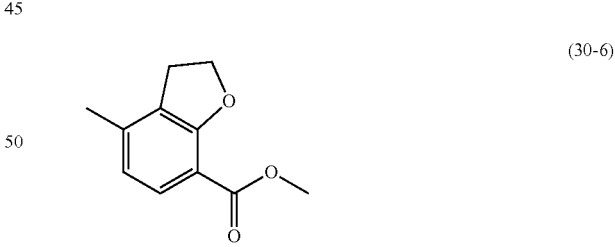

(30-6)

DIAD (1.7 mL, 8.66 mmol) was slowly added dropwise into a mixture of the compound (30-5) (910 mg, 4.33 mmol) in THF (30 mL) as well as PPh₃ (2.27 g, 8.66 mmol) at 0° C. in a nitrogen atmosphere. A reaction mixture was stirred overnight at room temperature. After a reaction was completed, a volatile solvent was evaporated under reduced pressure. A resulting residue was purified by means of a silica gel column chromatography, so as to obtain the title compound (30-6) (813 mg, 4.23 mmol, 98%).

¹H NMR (400 MHz, CDCl₃); δ 7.65 (d, J=8.0 Hz, 1H), 6.70 (d, J=8.0 Hz, 1H), 4.74 (t, J=8.8 Hz, 2H), 3.89 (s, 3H), 3.13 (t, J=8.8 Hz, 2H), 2.28 (s, 3H)

Step 7. Synthesis of methyl 5-bromo-4-methyl-2,3-dihydrobenzofuran-7-carboxylate (30-7)

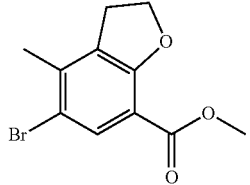

(30-7)

Br$_2$ (0.66 mL, 12.8 mmol) was added dropwise into a solution of the compound (30-6) (1.23 g, 6.40 mmol) in AcOH (20 mL) at room temperature. A resulting mixture was stirred overnight at room temperature, after which a reaction with a reactant was completed with a saturated Na$_2$S$_2$O$_3$ solution, so as to perform an extraction with EtOAc. An organic layer was dried over anhydrous MgSO$_4$, filtered and concentrated under vacuum. A resulting residue was purified by means of a silica gel column chromatography, so as to obtain the title compound (30-7) (1.58 g, 5.83 mmol, 91%).

$^1$H NMR (400 MHz, CDCl$_3$); δ 7.92 (s, 1H), 4.76 (t, J=8.8 Hz, 2H), 3.89 (s, 3H), 3.19 (t, J=8.8 Hz, 2H), 2.33 (s, 3H)

Step 8. Synthesis of 5-bromo-4-methyl-2,3-dihydrobenzofuran-7-carboxylic acid (30-8)

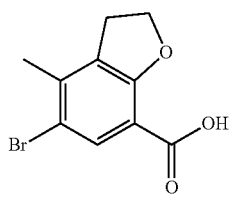

(30-8)

LiOH.H$_2$O (489 mg, 11.7 mmol) was added into a solution of the compound (30-7) (1.58 g, 5.83 mmol) in THF/MeOH/water (12 mL/4 mL/4 mL) at room temperature.

A reaction mixture was stirred at room temperature for 4 hours. After a reaction was completed, a volatile substance was removed under reduced pressure. A 1N—HCl aqueous solution was added into a residue to carry out acidification, during which a resulting mixture was stirred to precipitate a crude product. The crude product was filtered, washed with water and dried under high vacuum, so as to obtain the title compound (30-8) (1.02 g, 3.97 mmol, 68%).

$^1$H NMR (400 MHz, CD$_3$OD); δ 7.81 (s, 1H), 4.70 (t, J=8.8 Hz, 2H), 3.23 (t, J=8.8 Hz, 2H), 2.34 (s, 3H)

Step 9. Synthesis of 5-bromo-7-(4-methoxybenzyl)-4-methyl-2,3-dihydrobenzofuran (30-9)

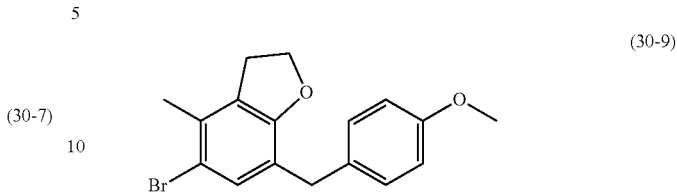

(30-9)

The title compound (30-9) was obtained with the compound (30-8) by means of a method as shown from Steps 4 to 5 of Example 1.

$^1$H NMR (400 MHz, CDCl$_3$); δ 7.13 (d, J=8.4 Hz, 2H), 7.04 (s, 1H), 6.82 (d, J=8.4 Hz, 2H), 4.59 (t, J=8.4 Hz, 2H), 3.78 (s, 5H), 3.16 (t, J=8.8 Hz, 2H), 2.25 (s, 3H)

Step 10. Synthesis of a Target Compound

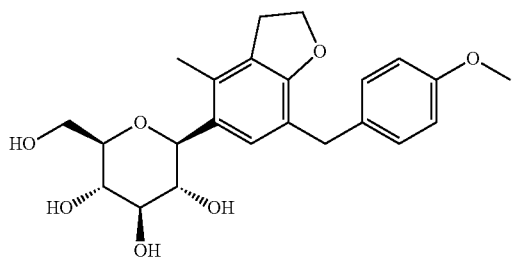 [SMILES: COc1ccc(Cc2cc([C@@H]3O[C@H](CO)[C@@H](O)[C@H](O)[C@H]3O)c(C)c3c2OCC3)cc1]

The target compound was obtained with the compound (30-9) by means of a method as shown from Steps 6 to 7 of Example 1.

$^1$H NMR (400 MHz, CD$_3$OD); δ 7.11 (d, J=8.4 Hz, 2H), 7.02 (s, 1H), 6.76 (d, J=8.8 Hz, 2H), 4.54 (t, J=8.8 Hz, 2H), 4.36 (d, J=9.2 Hz, 1H), 3.86-3.83 (m, 1H), 3.77 (s, 2H), 3.73 (s, 3H), 3.66-3.62 (m, 1H), 3.51-3.44 (m, 2H), 3.37-3.35 (m, 2H), 3.14 (t, J=8.8 Hz, 2H), 2.27 (s, 3H)

Example 31. Preparation of (2S,3R,4R,5S,6R)-2-(7-(4-ethoxybenzyl)-4-methyl-2,3-dihydrobenzofuran-5-yl)-6-(hydroxymethyl)tetrahydro-2H-pyran-3,4,5-triol

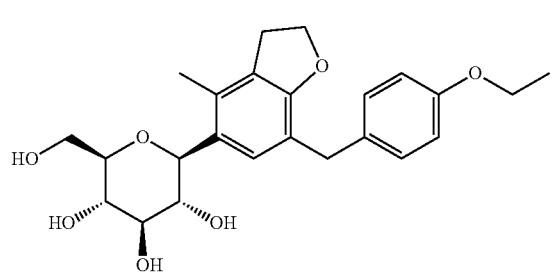 [SMILES: CCOc1ccc(Cc2cc([C@@H]3O[C@H](CO)[C@@H](O)[C@H](O)[C@H]3O)c(C)c3c2OCC3)cc1]

The target compound was obtained by means of a method as shown in Example 30.

$^1$H NMR (400 MHz, CD$_3$OD); δ 7.10 (d, J=8.4 Hz, 2H), 7.03 (s, 1H), 6.75 (d, J=8.8 Hz, 2H), 4.53 (t, J=8.8 Hz, 2H), 4.36 (d, J=9.2 Hz, 1H), 3.96 (q, J=7.2 Hz, 2H), 3.85 (d,

J=11.6 Hz, 1H), 3.76 (s, 2H), 3.66-3.62 (m, 1H), 3.54-3.45 (m, 2H), 3.37-3.35 (m, 2H), 3.13 (t, J=8.6 Hz, 2H), 2.26 (s, 3H), 1.34 (t, J=6.8 Hz, 3H)

Example 32. Preparation of (2R,3S,4R,5R,6S)-2-(hydroxymethyl)-6-(4-methyl-7-(4-(methylthio)benzyl)-2,3-dihydrobenzofuran-5-yl)tetrahydro-2H-pyran-3,4,5-triol Step 1. Synthesis of 5-bromo-4-methyl-7-(4-(methylthio)benzyl)-2,3-dihydrobenzofuran (32-1)

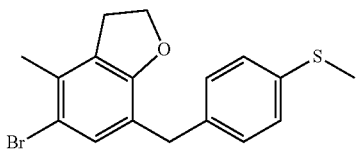
(32-1)

The title compound (32-1) was obtained with the compound (30-8) obtained in Step 8 of Example 30 by means of a method as shown from Steps 1 to 3 of Example 4.

$^1$H NMR (400 MHz, CDCl$_3$); δ 7.18 (d, J=8.8 Hz, 2H), 7.14 (d, J=8.4 Hz, 2H), 7.04 (s, 1H), 4.59 (t, J=8.8 Hz, 2H), 3.79 (s, 2H), 3.17 (t, J=8.8 Hz, 2H), 2.46 (s, 3H), 2.25 (s, 3H)

Step 2. Synthesis of a Target Compound

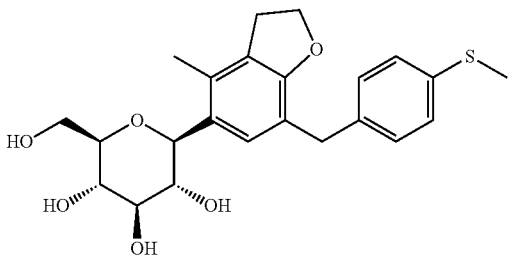 [SMILES: CSc1ccc(Cc2cc([C@@H]3O[C@H](CO)[C@@H](O)[C@H](O)[C@H]3O)c(C)c3c2OCC3)cc1]

The target compound was obtained with the compound (32-1) by means of a method as shown in Step 4 of Example 4.

$^1$H NMR (400 MHz, CD$_3$OD); δ 7.16-7.11 (m, 4H), 7.04 (s, 1H), 4.54 (t, J=8.4 Hz, 2H), 4.36 (d, J=8.8 Hz, 1H), 3.85 (d, J=12.0 Hz, 1H), 3.80 (s, 2H), 3.64 (dd, J=12.0, 5.2 Hz, 1H), 3.54-3.45 (m, 2H), 3.38-3.36 (m, 2H), 3.14 (t, J=8.4 Hz, 2H), 2.42 (s, 3H), 2.27 (s, 3H)

Examples 33 and 34

Target compounds of Examples 33 and 34 were obtained by means of a method as shown in Example 32.

Example 33. Preparation of (2S,3R,4R,5S,6R)-2-(7-(4-ethylbenzyl)-4-methyl-2,3-dihydrobenzofuran-5-yl)-6-(hydroxymethyl)tetrahydro-2H-pyran-3,4,5-triol

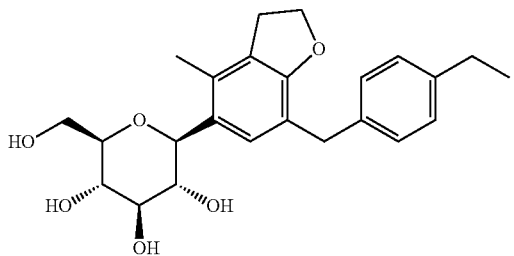 [SMILES: CCc1ccc(Cc2cc([C@@H]3O[C@H](CO)[C@@H](O)[C@H](O)[C@H]3O)c(C)c3c2OCC3)cc1]

$^1$H NMR (400 MHz, CD$_3$OD); δ 7.11 (d, J=7.2 Hz, 2H), 7.05 (s, 3H), 4.54 (t, J=8.4 Hz, 2H), 4.36 (d, J=9.2 Hz, 1H), 3.86-3.80 (m, 3H), 3.68-3.61 (m, 1H), 3.46-3.54 (m, 2H), 3.38 (s, 2H), 3.14 (t, J=8.4 Hz, 2H), 2.58 (q, J=7.6 Hz, 2H), 2.27 (s, 3H), 1.18 (t, J=7.2 Hz, 3H)

Example 34. Preparation of (2R,3S,4R,5R,6S)-2-(hydroxymethyl)-6-(4-methyl-7-(4-vinylbenzyl)-2,3-dihydrobenzofuran-5-yl)tetrahydro-2H-pyran-3,4,5-triol

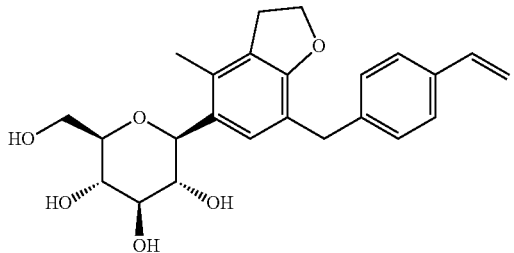 [SMILES: C=Cc1ccc(Cc2cc([C@@H]3O[C@H](CO)[C@@H](O)[C@H](O)[C@H]3O)c(C)c3c2OCC3)cc1]

$^1$H NMR (400 MHz, CD$_3$OD); (7.27 (d, J=7.6 Hz, 2H), 7.16 (d, J=8.0 Hz, 2H), 7.04 (s, 1H), 6.66 (dd, J=17.6, 11.2 Hz, 1H), 5.68 (dd, J=17.6, 1.2 Hz, 1H), 5.13 (dd, J=10.8, 0.8 Hz, 1H), 4.54 (t, J=8.8 Hz, 2H), 4.36 (d, J=9.2 Hz, 1H), 3.86-3.83 (m, 3H), 3.66-3.53 (m, 1H), 3.51-3.44 (m, 2H), 3.39-3.34 (m, 2H), 3.14 (t, J=8.8 Hz, 2H), 2.27 (s, 3H)

Example 35. Preparation of (2S,3R,4R,5S,6R)-2-(4-chloro-7-(4-ethoxybenzyl)-2,3-dihydrobenzofuran-5-yl)-6-(hydroxymethyl)tetrahydro-2H-pyran-3,4,5-triol Step 1. Synthesis of methyl 4-chloro-2-hydroxybenzoate (35-1)

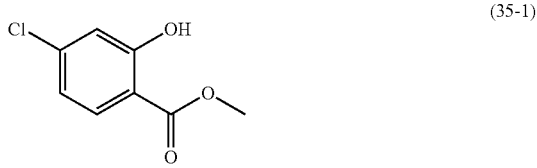
(35-1)

SOCl$_2$ (12.6 mL, 174 mmol) was added dropwise into a solution of 4-chlorosalicylic acid (10.0 g, 58.0 mmol, TCI reagent) in MeOH (200 mL) at 0° C. in a nitrogen atmosphere. A resulting mixture was stirred at reflux for 4 hours. After a reaction was completed, a volatile solvent was evaporated under reduced pressure. A saturated NaHCO$_3$ aqueous solution was slowly added into a resulting residue, after which a water layer was extracted with EtOAc. An organic layer was washed with brine, after which the resulting product was dried over anhydrous MgSO$_4$, filtered and concentrated under vacuum. A resulting residue was purified by means of a silica gel column chromatography, so as to obtain the title compound (35-1) (7.6 g, 40.7 mmol, 70%).

$^1$H NMR (400 MHz, CDCl$_3$); δ 7.76 (d, J=8.8 Hz, 1H), 7.01 (d, J=2.0 Hz, 1H), 6.87 (dd, J=8.4, 2.0 Hz, 1H), 3.95 (s, 3H)

Step 2. Synthesis of methyl 2-(allyloxy)-4-chlorobenzoate (35-2)

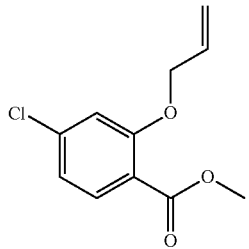

(35-2)

Allyl bromide (5.3 mL, 61.0 mmol) was added dropwise into a mixture of the compound (35-1) (7.59 g, 40.7 mmol) in DMF (114 mL) as well as K$_2$CO$_3$ (8.43 g, 61.0 mmol) at room temperature in a nitrogen atmosphere. A reaction mixture was stirred overnight at room temperature, after which a reaction thereof was completed with water. A water layer was extracted with EtOAc, after which an organic layer was washed with brine, such that the resulting product was dried over anhydrous MgSO$_4$, filtered and concentrated under vacuum. A resulting residue was purified by means of a silica gel column chromatography, so as to obtain the title compound (35-2) (8.50 g, 37.5 mmol, 92%).

$^1$H NMR (400 MHz, CDCl$_3$); δ 7.78 (d, J=8.0 Hz, 1H), 7.26-6.95 (m, 2H), 6.07-6.02 (m, 1H), 5.53 (dd, J=17.2, 1.6 Hz, 1H), 5.34 (dd, J=10.4, 1.2 Hz, 1H), 4.63-4.61 (m, 2H), 3.89 (s, 3H)

Step 3. Synthesis of methyl 3-allyl-4-chloro-2-hydroxybenzoate (35-3)

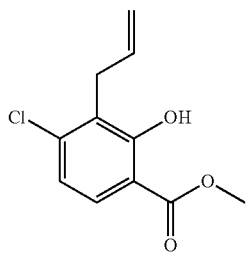

(35-3)

The compound (35-2) (2.10 g, 9.27 mmol) was stirred in a microwave reactor at 250° C. for 1 hour. A crude compound (35-3) (2.01 g, 8.87 mmol, 96%) was used in a following step without an additional purification.

$^1$H NMR (400 MHz, CDCl$_3$); δ 11.26 (s, 1H), 7.66 (d, J=8.8 Hz, 1H), 6.92 (d, J=8.8 Hz, 1H), 5.98-5.91 (m, 1H), 5.07-5.02 (m, 2H), 3.95 (s, 3H), 3.59 (d, J=6.0 Hz, 2H)

Step 4. Synthesis of methyl 4-chloro-2-hydroxy-3-(2-oxoethyl)benzoate (35-4)

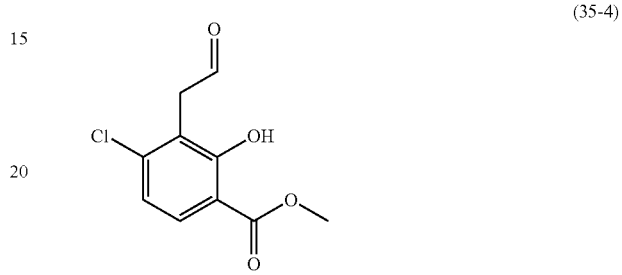

(35-4)

N-methylmorpholine N-oxide (1.55 g, 13.2 mmol) and OsO$_4$ (22.4 mL, 0.09 mmol) were added into a solution of the compound (35-3) (2.00 g, 8.82 mmol) in acetone/water (30 mL/3 mL) in a nitrogen atmosphere. After stirring a resulting reaction mixture at room temperature for 8 hours, a reaction with a reactant was completed with a saturated Na$_2$S$_2$O$_3$ aqueous solution, so as to perform an extraction of a resulting mixture with EtOAc. An organic layer was dried over anhydrous MgSO$_4$, filtered and concentrated under vacuum, so as to obtain a crude intermediate, which was used without an additional purification. NaIO$_4$ (5.61 g, 26.3 mmol) was added into a crude intermediate solution in THF/water (50 mL/30 mL) at room temperature in a nitrogen atmosphere. After stirring a resulting reaction mixture at room temperature for 5 hours, a reaction with a reactant was completed with a saturated Na$_2$S$_2$O$_3$ aqueous solution, so as to perform an extraction of a resulting mixture with EtOAc.

An organic layer was dried over anhydrous MgSO$_4$, filtered and concentrated under vacuum, so as to obtain a crude compound (35-4) (1.90 g, 8.31 mmol, 95%), which was used without an additional purification.

$^1$H NMR (400 MHz, CDCl$_3$); δ 11.32 (s, 1H), 9.73 (s, 1H), 7.75 (d, J=8.4 Hz, 1H), 6.98 (d, J=8.4 Hz, 1H), 3.97 (s, 5H)

Step 5. Synthesis of methyl 4-chloro-2-hydroxy-3-(2-hydroxyethyl)benzoate (35-5)

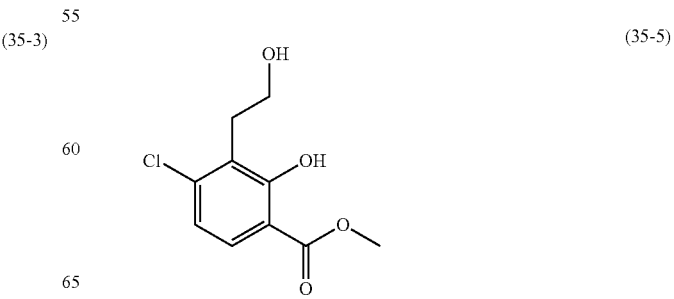

(35-5)

NaBH₄ (628 mg, 16.6 mmol) was added into a solution of the compound (35-4) (1.90 g, 8.31 mmol) in MeOH (30 mL) at 0° C. in a nitrogen atmosphere. After stirring a resulting reaction mixture at 0° C. for 1 hour, a reaction with a reactant was completed with a saturated NH₄Cl aqueous solution, so as to perform an extraction of a resulting mixture with EtOAc. An organic layer was dried over anhydrous MgSO₄, filtered and concentrated under vacuum. A resulting residue was purified by means of a silica gel column chromatography, so as to obtain the title compound (35-5) (1.45 g, 6.29 mmol, 76%).

¹H NMR (400 MHz, CDCl₃); δ 11.37 (s, 1H), 7.67 (d, J=8.8 Hz, 1H), 6.94 (d, J=8.8 Hz, 1H), 3.96 (s, 3H), 3.87 (dd, J=12.8, 6.0 Hz, 2H), 3.16 (t, J=6.4 Hz, 2H)

Step 6. Synthesis of methyl 4-chloro-2,3-dihydrobenzofuran-7-carboxylate (35-6)

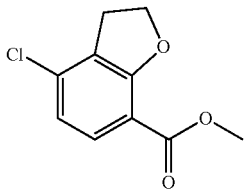

(35-6)

DIAD (2.47 mL, 12.6 mmol) was slowly added dropwise into a mixture of the compound (35-5) (1.45 g, 6.29 mmol) in THF (30 mL) as well as PPh₃ (3.30 g, 12.6 mmol) at 0° C. in a nitrogen atmosphere. A reaction mixture was stirred overnight at room temperature. After a reaction was completed, a volatile solvent was evaporated under reduced pressure. A resulting residue was purified by means of a silica gel column chromatography, so as to obtain the title compound (35-6) (1.31 g, 6.16 mmol, 98%).

¹H NMR (400 MHz, CDCl₃); δ 7.69 (d, J=8.4 Hz, 1H), 6.88 (d, J=8.4 Hz, 1H), 4.79 (t, J=8.8 Hz, 2H), 3.90 (s, 3H), 3.27 (t, J=8.8 Hz, 2H)

Step 7. Synthesis of methyl 5-bromo-4-chloro-2,3-dihydrobenzofuran-7-carboxylate (35-7)

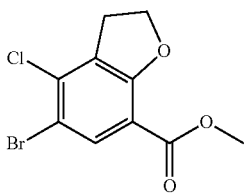

(35-7)

Br₂ (0.4 mL, 8.01 mmol) was added dropwise into a solution of the compound (35-6) (1.31 g, 6.16 mmol) in AcOH (20 mL) at room temperature. A resulting mixture was stirred overnight at room temperature, after which a reaction with a reactant was completed with a saturated Na₂S₂O₃ solution, so as to perform an extraction with EtOAc. An organic layer was dried over anhydrous MgSO₄, filtered and concentrated under vacuum. A crude compound (35-7) (1.70 g, 5.83 mmol, 95%) was used in a following step without an additional purification.

¹H NMR (400 MHz, CDCl₃); δ 8.00 (s, 1H), 4.81 (t, J=8.8 Hz, 2H), 3.91 (s, 3H), 3.31 (t, J=8.8 Hz, 2H)

Step 8. Synthesis of 5-bromo-4-chloro-2,3-dihydrobenzofuran-7-carboxylic acid (35-8)

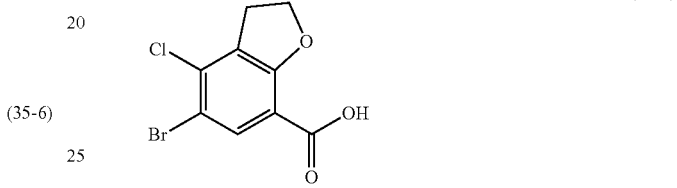

(35-8)

LiOH.H₂O (490 mg, 11.2 mmol) was added into a solution of the compound (35-7) (1.70 g, 5.83 mmol) in THF/MeOH/water (15 mL/5 mL/5 mL) at room temperature. A reaction mixture was stirred at room temperature for 4 hours. After a reaction was completed, a volatile substance was removed under reduced pressure. A 1N—HCl aqueous solution was added into a residue to carry out acidification, during which a resulting mixture was stirred to precipitate a crude product. The crude product was filtered, washed with water and dried under high vacuum, so as to obtain the title compound (35-8) (1.54 g, 5.54 mmol, 95%).

¹H NMR (400 MHz, CD₃OD); δ 7.93 (s, 1H), 4.76 (t, J=8.8 Hz, 2H), 3.35-3.30 (m, 2H)

Step 9. Synthesis of a Target Compound

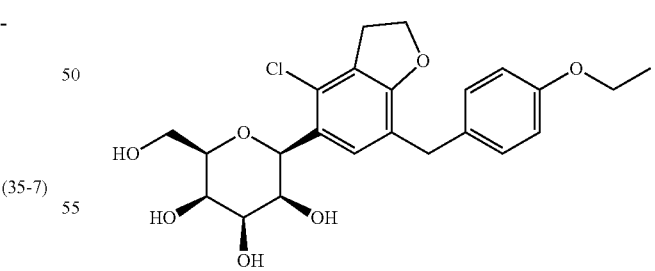

The target compound was obtained with the compound (35-8) by means of a method as shown from Steps 4 to 7 of Example 1.

¹H NMR (400 MHz, CD₃OD); δ 7.14-7.10 (m, 3H), 6.77 (d, J=8.4 Hz, 2H), 4.63-4.59 (m, 3H), 3.97 (q, J=6.8 Hz, 2H), 3.86-3.78 (m, 3H), 3.68-3.64 (m, 1H), 3.49-3.47 (m, 2H), 3.39-3.37 (m, 2H), 3.25 (t, J=8.8 Hz, 2H), 1.35 (t, J=6.8 Hz, 3H)

Example 36. Preparation of (2R,3S,4R,5R,6S)-2-(hydroxymethyl)-6-(4-(4-methoxybenzyl)-7-methyl-2,3-dihydrobenzofuran-6-yl)tetrahydro-2H-pyran-3,4,5-triol

Step 1. Synthesis of 6-bromo-7-methyl-2,3-dihydrobenzofuran-4-carboxylic acid (36-1)

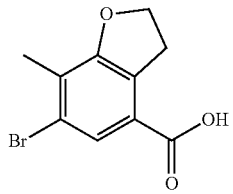

(36-1)

The title compound (36-1) was obtained with 3-hydroxy-4-methylbenzoic acid (TCI reagent) by means of a method as shown from Steps 1 to 8 of Example 30.

$^1$H NMR (400 MHz, CDCl$_3$); δ 7.15 (s, 1H), 4.52 (t, J=8.8 Hz, 2H), 3.36 (t, J=8.8 Hz, 2H), 2.20 (s, 3H)

Step 2. Synthesis of 6-bromo-4-(4-methoxybenzyl)-7-methyl-2,3-dihydrobenzofuran (36-2)

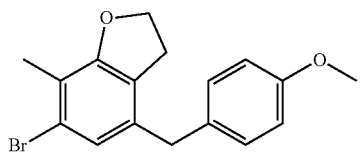

(36-2)

The title compound according to an inventive title (36-2) was obtained with the compound (36-1) by means of a method as shown from Steps 4 to 5 of Example 1.

$^1$H NMR (400 MHz, CDCl$_3$); δ 7.18 (s, 1H), 7.05 (d, J=8.8 Hz, 2H), 6.80 (d, J=8.8 Hz, 2H), 4.52 (t, J=8.8 Hz, 2H), 4.00 (s, 2H), 3.77 (s, 3H), 3.04 (t, J=8.8 Hz, 2H), 2.16 (s, 3H)

Step 3. Synthesis of a Target Compound

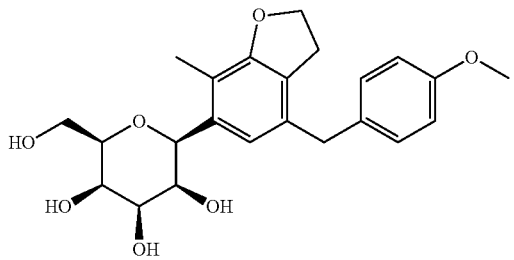 [SMILES: COc1ccc(Cc2cc([C@@H]3O[C@H](CO)[C@H](O)[C@H](O)[C@@H]3O)c(C)c3c2CCO3)cc1]

The target compound was obtained with the compound (36-2) by means of a method as shown from Steps 6 to 7 of Example 1.

$^1$H NMR (400 MHz, CD$_3$OD); δ 7.11 (s, 1H), 7.04 (d, J=9.2 Hz, 2H), 6.78 (d, J=8.8 Hz, 2H), 4.47 (t, J=9.2 Hz, 2H), 4.35 (d, J=9.6 Hz, 1H), 4.13 (d, J=12.0 Hz, 1H), 3.89 (d, J=16.0 Hz, 1H), 3.73 (dd, J=12.0, 2.4 Hz, 1H), 3.73 (s, 3H), 3.62-3.56 (m, 2H), 3.44-3.35 (m, 2H), 3.19-3.15 (m, 1H), 3.04-2.92 (m, 2H), 2.16 (s, 3H)

Example 37. Preparation of (2R,3S,4R,5R,6S)-2-(hydroxymethyl)-6-(7-methyl-4-(4-vinylbenzyl)-2,3-dihydrobenzofuran-6-yl)tetrahydro-2H-pyran-3,4,5-triol

Step 1. Synthesis of 6-bromo-7-methyl-4-(4-vinylbenzyl)-2,3-dihydrobenzofuran (37-1)

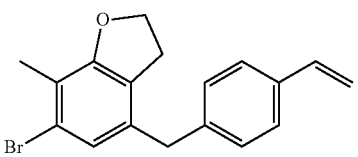

(37-1)

The title compound (37-1) was obtained with the compound (36-1) obtained in Step 1 of Example 36 by means of a method as shown from Steps 1 to 3 of Example 4.

$^1$H NMR (400 MHz, CDCl$_3$); δ 7.31 (d, J=7.2 Hz, 2H), 7.18 (s, 1H), 7.09 (d, J=7.2 Hz, 2H), 6.68 (dd, J=17.6, 10.8 Hz, 1H), 5.69 (d, J=17.6 Hz, 1H), 5.41 (d, J=10.8 Hz, 1H), 4.53 (t, J=8.8 Hz, 2H), 4.06 (s, 2H), 3.09 (t, J=8.8 Hz, 2H), 2.17 (s, 3H)

Step 2. Synthesis of a Target Compound

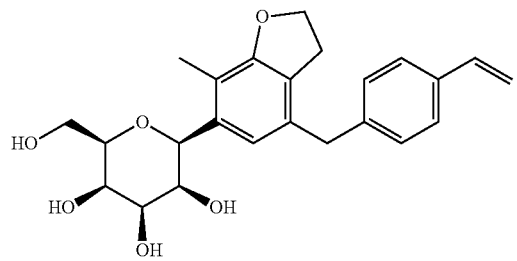 [SMILES: C=Cc1ccc(Cc2cc([C@@H]3O[C@H](CO)[C@H](O)[C@H](O)[C@@H]3O)c(C)c3c2CCO3)cc1]

The target compound was obtained with the compound (37-1) by means of a method as shown in Step 4 of Example 4.

$^1$H NMR (400 MHz, CD$_3$OD); δ 7.29 (d, J=8.4 Hz, 2H), 7.11 (s, 1H), 7.09 (d, J=7.6 Hz, 2H), 6.67 (dd, J=17.6, 10.8 Hz, 1H), 5.69 (d, J=17.6 Hz, 1H), 5.14 (d, J=10.8 Hz, 1H), 4.48 (t, J=8.8 Hz, 2H), 4.33 (d, J=9.6 Hz, 1H), 4.19 (d, J=16.0 Hz, 1H), 3.95 (d, J=16.4 Hz, 1H), 3.71 (dd, J=12.0, 2.4 Hz, 1H), 3.61-3.52 (m, 2H), 3.43-3.35 (m, 2H), 3.17-3.14 (m, 1H), 3.07-2.92 (m, 2H), 2.16 (s, 3H)

Example 38. Preparation of (2R,3S,4R,5R,6S)-2-(hydroxymethyl)-6-(8-methoxy-5-(4-methoxybenzyl)chroman-7-yl)tetrahydro-2H-pyran-3,4,5-triol Step 1. Synthesis of methyl 3-(allyloxy)-4-methoxybenzoate (38-1)

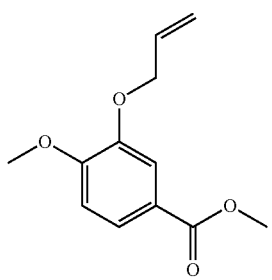

(38-1)

Allyl bromide (2.8 mL, 32.9 mmol) was added dropwise into a mixture of methyl isocyanilate (5.00 g, 27.4 mmol, TCI reagent) in DMF (30 mL) as well as K$_2$CO$_3$ (4.55 g, 32.9 mmol) at room temperature in a nitrogen atmosphere. A reaction mixture was stirred overnight at room temperature, after which a reaction thereof was completed with water. A water layer was extracted with EtOAc, after which an organic layer was washed with brine, such that the resulting product was dried over anhydrous MgSO$_4$, filtered and concentrated under vacuum. A resulting residue was purified by means of a silica gel column chromatography, so as to obtain the title compound (38-1) (5.80 g, 26.1 mmol, 95%).

$^1$H NMR (400 MHz, CDCl$_3$); δ 7.68 (dd, J=8.0, 2.0 Hz, 1H), 7.56 (s, 1H), 6.90 (d, J=8.8 Hz, 1H), 6.17-6.04 (m, 1H), 5.44 (dd, J=17.6, 1.2 Hz, 1H), 5.31 (dd, J=10.4, 1.2 Hz, 1H), 4.66 (d, J=5.6 Hz, 2H), 3.93 (s, 3H), 3.89 (s, 3H)

Step 2. Synthesis of methyl 2-allyl-3-hydroxy-4-methoxybenzoate (38-2)

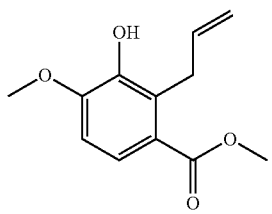

(38-2)

The compound (38-1) (1.00 g, 4.50 mmol) was stirred in a microwave reactor at 250° C. for 1 hour. A crude compound (38-2) (0.99 g, 4.45 mmol, 99%) was used in a following step without an additional purification.

$^1$H NMR (400 MHz, CDCl$_3$); δ 7.52 (d, J=8.4 Hz, 1H), 6.76 (d, J=8.8 Hz, 1H), 6.08-5.98 (m, 1H), 5.77 (s, 1H), 5.04-4.97 (m, 2H), 3.94 (s, 3H), 3.85 (s, 3H), 3.82 (d, J=6.0 Hz, 2H)

Step 3. Synthesis of methyl 3-hydroxy-2-(3-hydroxpropyl)-4-methoxybenzoate

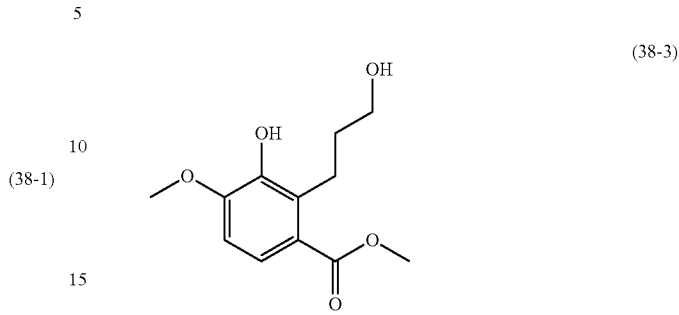

(38-3)

A BH$_3$.SMe$_2$ complex (1.0 mL, 10.0 mmol, 10.0 M in methylsulfide) was slowly added into a solution of the compound (38-2) (1.91 g, 8.59 mmol) in THF (40 mL) at −10° C. in a nitrogen atmosphere, after which a reaction mixture was stirred at room temperature for 1 hour. An H$_2$O$_2$ (1.2 mL) solution in a saturated NaHCO$_3$ solution (20 mL) solution was slowly added thereinto. A resulting reaction mixture was cooled at 0° C. and stirred for 30 minutes. EtOAc was added into the resulting mixture. An organic layer was washed with brine, after which the resulting product was dried over anhydrous MgSO$_4$, filtered and concentrated under vacuum. A crude compound (38-3) (2.06 g, 8.57 mmol, 99%) was used in a following step without an additional purification.

$^1$H NMR (400 MHz, CD$_3$OD); δ 7.44 (d, J=8.4 Hz, 1H), 6.85 (d, J=8.8 Hz, 1H), 3.91 (s, 3H), 3.84 (s, 3H), 3.57 (t, J=6.8 Hz, 2H), 3.03 (t, J=7.6 Hz, 2H), 1.85-1.77 (m, 2H)

Step 4. Synthesis of methyl 8-methoxychroman-5-carboxylate (38-4)

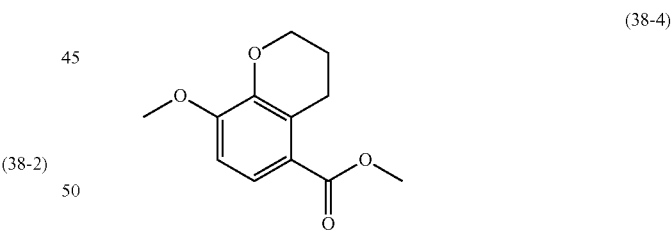

(38-4)

DIAD (3.40 mL, 17.15 mmol) was slowly added into a mixture of the compound (38-3) (2.06 g, 8.57 mmol) in THF (20 mL) as well as PPh$_3$ (4.5 g, 17.2 mmol) at 0° C. in a nitrogen atmosphere. A reaction mixture was stirred overnight at room temperature. After a reaction was completed, a volatile solvent was evaporated under reduced pressure. A resulting residue was purified by means of a silica gel column chromatography, so as to obtain the title compound (38-4) (1.87 g, 8.41 mmol, 98%).

$^1$H NMR (400 MHz, CDCl$_3$); δ 7.58 (d, J=8.4 Hz, 1H), 6.74 (d, J=8.4 Hz, 1H), 4.27 (t, J=5.2 Hz, 2H), 3.92 (s, 3H), 3.85 (s, 3H), 3.14 (t, J=6.4 Hz, 2H), 2.05-1.99 (m, 2H)

Step 5. Synthesis of 8-methoxychroman-5-carboxylic acid (38-5)

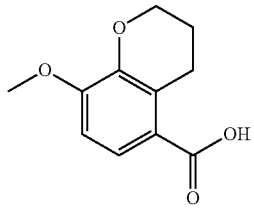

(38-5)

A mixture of the compound (38-4) (1.87 g, 8.41 mmol) in THF (5 mL) as well as 1N—NaOH aqueous solution (13 mL) was stirred at reflux for 2 hours. A resulting reaction mixture was cooled at room temperature, after which the resulting mixture was acidified by means of a 1N—HCl solution, so as to perform an extraction with EtOAc. A combined organic layer was dried over anhydrous MgSO$_4$, filtered and concentrated under vacuum. A resulting residue was purified by means of a silica gel column chromatography, so as to obtain the title compound (38-5) (1.72 g, 8.26 mmol, 96%).

$^1$H NMR (400 MHz, CDCl$_3$); δ 7.59 (d, J=8.8 Hz, 1H), 6.84 (d, J=8.8 Hz, 1H), 4.19 (t, J=5.2 Hz, 2H), 3.86 (s, 3H), 3.12 (t, J=6.4 Hz, 2H), 2.01-1.95 (m, 2H)

Step 6. Synthesis of 7-bromo-8-methoxychroman-5-carboxylic acid (38-6)

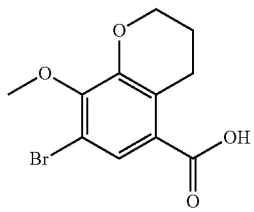

(38-6)

Br$_2$ (0.28 mL, 10.7 mmol) was added dropwise into a solution of the compound (38-5) (1.72 g, 8.26 mmol) in AcOH (20 mL) at room temperature. A resulting mixture was stirred overnight at room temperature, after which a reaction with a reactant was completed with a saturated Na$_2$S$_2$O$_3$ solution, so as to perform an extraction with EtOAc. An organic layer was dried over anhydrous MgSO$_4$, filtered and concentrated under vacuum. A crude compound (38-6) (1.86 g, 6.18 mmol, 75%) was used in a following step without an additional purification.

$^1$H NMR (400 MHz, CD$_3$OD); δ 6.99 (s, 1H), 4.19 (t, J=5.2 Hz, 2H), 3.82 (s, 3H), 2.77 (t, J=6.4 Hz, 2H), 2.02-1.96 (m, 2H)

Step 7. Synthesis of 7-bromo-8-methoxy-5-(4-methoxybenzyl)chroman (38-7)

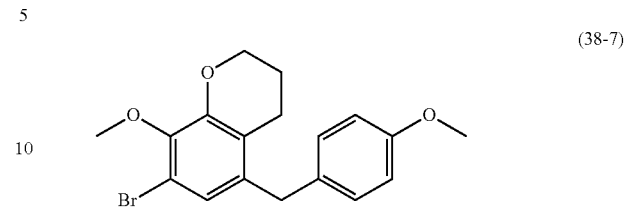

(38-7)

The title compound (38-7) was obtained with the compound (38-6) by means of a method as shown from Steps 4 to 5 of Example 1.

$^1$H NMR (400 MHz, CDCl$_3$); δ 6.99-6.97 (m, 3H), 6.80 (d, J=8.8 Hz, 2H), 4.17 (t, J=4.8 Hz, 2H), 4.06 (s, 2H), 3.87 (s, 3H), 3.77 (s, 3H), 2.60 (t, J=6.4 Hz, 2H), 1.96-1.91 (m, 2H)

Step 8. Synthesis of a Target Compound

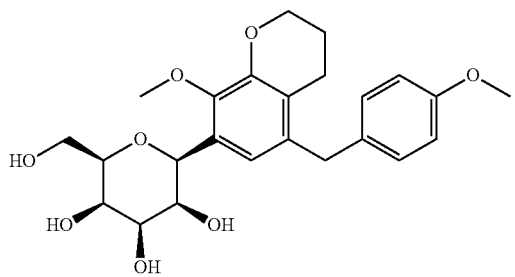 [SMILES: COc1ccc(Cc2cc([C@@H]3O[C@H](CO)[C@H](O)[C@H](O)[C@@H]3O)c(OC)c3c2CCCO3)cc1]

The target compound was obtained with the compound (38-7) by means of a method as shown from Steps 6 to 7 of Example 1.

$^1$H NMR (400 MHz, CD$_3$OD); δ 7.01-6.99 (m, 3H), 6.78 (d, J=8.4 Hz, 2H), 4.38 (d, J=9.6 Hz, 1H), 4.16-4.06 (m, 3H), 3.91-3.87 (m, 1H), 3.85 (s, 3H), 3.78-3.74 (m, 1H), 3.73 (s, 3H), 3.65-3.57 (m, 2H), 3.43-3.40 (m, 2H), 3.21-3.17 (m, 1H), 2.68-2.62 (m, 1H), 2.53-2.47 (m, 1H), 1.92-1.88 (m, 2H)

Example 39. Preparation of (2R,3S,4R,5R,6S)-2-(hydroxymethyl)-6-(8-methoxy-5-(4-methylbenzyl)chroman-7-yl)tetrahydro-2H-pyran-3,4,5-triol

Step 1. Synthesis of 7-bromo-8-methoxy-5-(4-methylbenzyl)chroman (39-1)

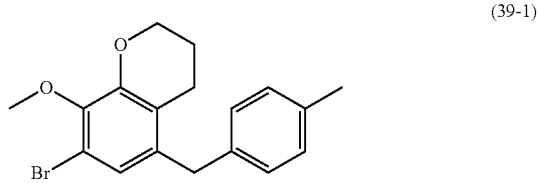

(39-1)

The title compound (39-1) was obtained with the compound (38-6) obtained in Step 6 of Example 38 by means of a method as shown from Steps 1 to 3 of Example 4.

¹H NMR (400 MHz, CDCl₃); δ 7.07 (d, J=7.6 Hz, 2H), 6.99 (s, 1H), 6.95 (d, J=8.0 Hz, 2H), 4.17 (t, J=5.2 Hz, 2H), 4.09 (s, 2H), 3.87 (s, 3H), 2.59 (t, J=6.4 Hz, 2H), 2.30 (s, 3H), 1.96-1.92 (m, 2H)

Step 2. Synthesis of a Target Compound

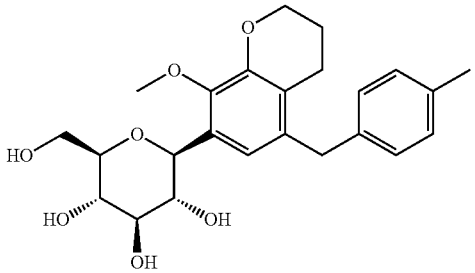 [SMILES: COc1c([C@@H]2O[C@H](CO)[C@@H](O)[C@H](O)[C@H]2O)cc(Cc2ccc(C)cc2)c2c1OCCC2]

The target compound was obtained with the compound (39-1) by means of a method as shown in Step 4 of Example 4.

¹H NMR (400 MHz, CD₃OD); δ 7.03 (d, J=8.0 Hz, 2H), 6.99 (s, 1H), 6.96 (d, J=8.0 Hz, 2H), 4.38 (d, J=9.6 Hz, 1H), 4.17 (d, J=16.8 Hz, 1H), 4.12-4.03 (m, 2H), 3.88 (d, J=10.0 Hz, 1H), 3.85 (s, 3H), 3.75 (dd, J=12.0, 2.4 Hz, 1H), 3.65-3.57 (m, 2H), 3.44-3.39 (m, 2H), 3.20-3.16 (m, 1H), 2.67-2.61 (m, 1H), 2.52-2.44 (m, 1H), 2.26 (s, 3H), 1.91-1.87 (m, 2H)

Example 40. Preparation of (2S,3R,4R,5S,6R)-2-(5-(4-ethoxybenzyl)-8-methylchroman-7-yl)-6-(hydroxymethyl)tetrahydro-2H-pyran-3,4,5-triol Step 1. Synthesis of 7-bromo-5-(4-ethoxybenzyl)-8-methylchroman (40-1)

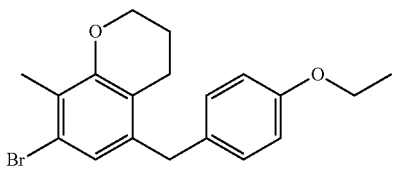

The title compound (40-1) was obtained with 3-hydroxy-4-methylbenzoic acid (TCI reagent) by means of a method as shown from Steps 1 to 7 of Example 38.

¹H NMR (400 MHz, CDCl₃); δ 7.24 (s, 1H), 6.97 (d, J=8.8 Hz, 2H), 6.78 (d, J=8.8 Hz, 2H), 4.10 (t, J=8.8 Hz, 2H), 4.08 (s, 2H), 3.96 (q, J=6.8 Hz, 2H), 2.60 (t, J=8.8 Hz, 2H), 2.15 (s, 3H), 1.94-1.87 (m, 2H), 1.39 (t, J=6.8 Hz, 3H)

Step 2. Synthesis of a Target Compound

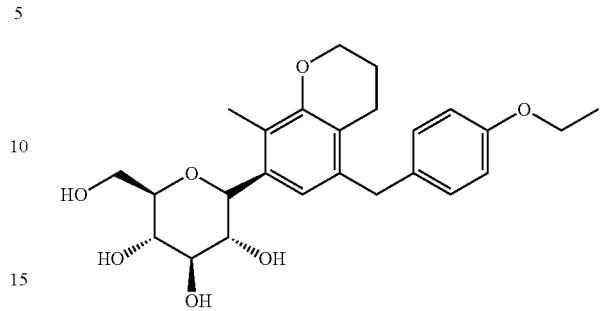

The target compound was obtained with the compound (40-1) by means of a method as shown from Steps 6 to 7 of Example 1.

¹H NMR (400 MHz, CD₃OD); δ 7.14 (s, 1H), 6.98 (d, J=8.8 Hz, 2H), 6.76 (d, J=8.8 Hz, 2H), 4.33 (d, J=9.2 Hz, 1H), 4.15-4.06 (m, 3H), 3.99-3.90 (m, 3H), 3.74 (dd, J=12.0, 2.0 Hz, 1H), 3.62-3.57 (m, 2H), 3.40-3.35 (m, 2H), 3.17-3.15 (m, 1H), 2.93 (s, 3H), 2.68-2.47 (m, 2H), 1.90-1.87 (m, 2H), 1.34 (t, J=6.8 Hz, 3H)

Example 41. Preparation of (2S,3R,4R,5S,6R)-2-(4-ethyl-7-(4-methylbenzyl)-2,3-dihydro-1H-indene-5-yl)-6-(hydroxymethyl)tetrahydro-2H-pyran-3,4,5-triol Step 1. Synthesis of (E)-pent-2-enal (41-1)

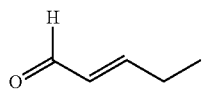

(41-1)

DCM (104 mL) was cooled at −78° C., after which (COCl)₂ (24 mL, 278.64 mmol) and DMSO (2.06 mL, 464.44 mmol) were added dropwise into a resulting product, such that a resulting mixture was stirred for 30 minutes. Trans-2-penten-1-ol (16.00 g, 185.76 mmol) was diluted in DCM (40 mL), after which a resulting solution was slowly added into a reaction flask for 15 minutes, such that a resulting mixture was stirred at the same temperature for 30 minutes, and then further stirred for 1 hour with a temperature rising to 0° C. Water was poured onto a resulting mixture to complete a reaction, and perform an extraction with diethyl ether. An organic layer was washed with brine, after which a resulting product was dried over anhydrous MgSO₄, filtered and concentrated, so as to obtain the title compound (41-1). A resulting compound was used immediately in a following reaction without an additional purification.

¹H NMR (400 MHz, CDCl₃); δ 9.52 (d, J=7.6 Hz, 1H), 6.86 (dt, J=15.6, 6.2 Hz, 1H), 6.16-6.09 (m, 1H), 2.41-2.34 (m, 2H), 1.13 (t, J=7.2 Hz, 3H)

Step 2. Synthesis of 5(2E,4E)-ethylhepta-2,4-dienoate (41-2)

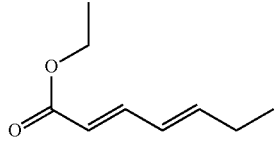
(41-2)

Sodium hydride (13.00 g, 325.08 mmol) was inserted into THF (200 mL), after which a resulting solution was cooled at −78° C. Triethyl phosphonoacetate (65 mL, 325.08 mmol) was slowly added into the resulting product for 5 minutes, after which a resulting mixture was stirred at the same temperature for 30 minutes. The compound (41-1) in THF (60 mL) was slowly added dropwise into the resulting mixture, after which the resulting mixture was stirred for 30 minutes, and then further stirred for 1 hour with a temperature rising to −40° C. A resulting product was diluted with diethyl ether, after which a saturated solution of ammonium chloride was slowly added into the resulting solution, such that a resulting mixture was stirred at room temperature for 10 minutes. An organic layer was washed twice with brine, after which a resulting product layer was dried over anhydrous MgSO$_4$, filtered and concentrated. A resulting residue was purified by means of a silica gel column chromatography, so as to obtain the title compound (41-2) (21.86 g, 141.75 mmol, 76%).

$^1$H NMR (400 MHz, CDCl$_3$); δ 7.29-7.23 (m, 1H), 6.18-6.10 (m, 2H), 5.79 (d, J=12.8 Hz, 1H), 4.19 (q, J=6.8 Hz, 2H), 2.24-2.18 (m, 2H), 1.29 (t, J=7.2 Hz, 3H), 1.05 (t, J=7.2 Hz, 3H)

Step 3. Synthesis of ethyl 7-ethyl-2,3-dihydro-1H-indene-4-carboxylate (41-3)

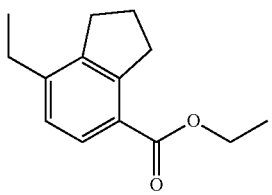
(41-3)

The compound (41-2) (21.80 g, 141.36 mmol) and 1-pyrrolidino-1-cyclopentene (22.67 mL, 155.50 mL) were dissolved in xylene (64 mL), after which a resulting solution was stirred at reflux for 24 hours. After cooling at room temperature, 1N HCl was added dropwise into the resulting solution to perform an extraction with EtOAc, after which a resulting extract was dried over anhydrous MgSO$_4$, filtered and concentrated. A resulting residue was purified by means of a silica gel column chromatography, so as to obtain the title compound (41-3) (12.20 g, 55.89 mmol, 59%).

$^1$H NMR (400 MHz, CDCl$_3$); δ 7.80 (d, J=8.0 Hz, 1H), 7.06 (d, J=8.0 Hz, 1H), 4.34 (q, J=7.2 Hz, 2H), 3.30 (t, J=7.6 Hz, 2H), 2.88 (t, J=7.6 Hz, 2H), 2.08 (q, J=7.6 Hz, 2H), 2.12-2.04 (m, 2H), 1.38 (t, J=7.2 Hz, 3H), 0.88 (t, J=7.2 Hz, 3H)

Step 4. Synthesis of 7-ethyl-2,3-dihydro-1H-indene-4-carboxylic acid (41-4)

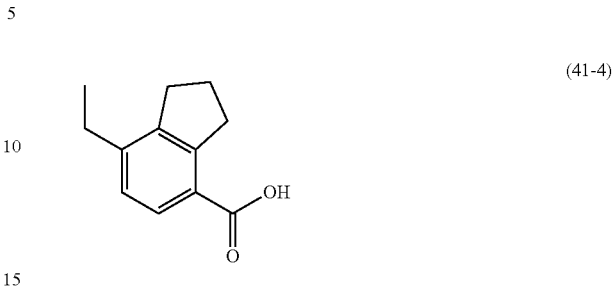
(41-4)

The compound (41-3) (11.50 g, 52.68 mmol) was dissolved in methanol (230 mL), after which a 2N sodium hydroxide aqueous solution (115 mL) was added dropwise into a resulting solution, such that a resulting mixture was stirred at reflux for 5 hours. Methanol was concentrated under reduced pressure, after which a resulting concentrate was cooled at 0° C., such that 1N HCl was slowly added dropwise thereinto until a mixed solution reached pH 6. A resulting solid was filtered and dried in a nitrogen atmosphere, so as to obtain the title compound (41-4) (7.60 g, 39.95 mmol, 76%).

$^1$H NMR (400 MHz, CD$_3$OD); δ 7.69 (d, J=8.0 Hz, 1H), 7.01 (d, J=8.0 Hz, 1H), 3.21 (t, J=7.6 Hz, 2H), 2.85 (t, J=7.6 Hz, 2H), 2.61 (q, J=7.6 Hz, 2H), 2.07-2.02 (m, 2H), 1.17 (t, J=7.6 Hz, 3H)

Step 5. Synthesis of 6-bromo-7-ethyl-2,3-dihydro-1H-indene-4-carboxylic acid (41-5)

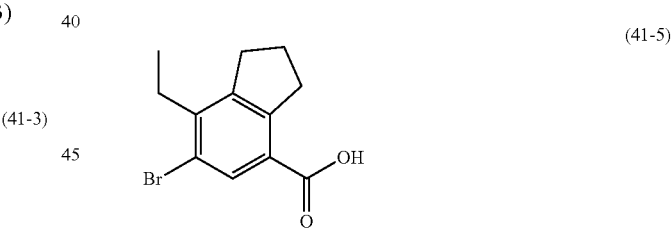
(41-5)

The compound (41-4) (7.60 g, 39.95 mmol) was dissolved in acetic acid (140 mL), after which nitric acid (4.56 mL, 59.92 mmol) and bromine (3.07 mL, 59.92 mmol) were added dropwise in order into a resulting mixed solution. Silver nitrate (10.18 g, 59.92 mmol) was dissolved in water (50 mL), after which a resulting solution was slowly added dropwise into a reaction mixture, after which a resulting mixture was stirred at room temperature for 12 hours. A reaction mixture was cooled at 0° C., after which a saturated solution of sodium thiosulfate was slowly added dropwise into a resulting mixture, so as to complete a reaction. A resulting mixture was extracted twice with EtOAc, after which an organic layer was dried over anhydrous MgSO$_4$, filtered and concentrated under reduced pressure. A concentrated solution was dried under vacuum to obtain the title compound (41-5), which was used in a following step without an additional purification.

Step 6. Synthesis of 5-bromo-4-ethyl-7-(4-methyl-benzyl)-2,3-dihydro-1H-indene (41-6)

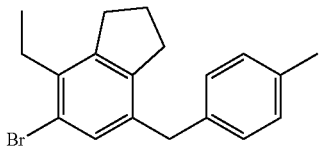

(41-6)

The title compound (41-6) was obtained with the compound (41-5) by means of a method as shown from Steps 1 to 3 of Example 4.

$^1$H NMR (400 MHz, CDCl$_3$); δ 7.13 (s, 1H), 7.10-7.02 (m, 4H), 3.82 (s, 2H), 2.90 (t, J=7.6 Hz, 2H), 2.75 (t, J=7.6 Hz, 2H), 2.71 (q, J=7.6 Hz, 2H), 2.31 (s, 3H), 2.08-2.01 (m, 2H), 1.25 (t, J=7.6 Hz, 3H)

Step 7. Synthesis of a Target Compound

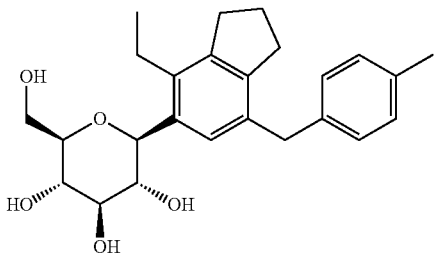 [SMILES: CCc1c([C@@H]2O[C@H](CO)[C@@H](O)[C@H](O)[C@H]2O)cc(Cc2ccc(C)cc2)c2c1CCC2]

The target compound was obtained with a compound (41-6) by means of a method as shown from Steps 6 to 7 of Example 1.

$^1$H NMR (400 MHz, CD$_3$OD); δ 7.08 (s, 1H), 6.98 (s, 4H), 4.39 (d, J=9.2 Hz, 1H), 3.82-3.79 (m, 3H), 3.63-3.59 (m, 1H), 3.55 (t, J=9.2 Hz, 1H), 3.47-3.43 (m, 1H), 3.35 (d, J=6.0 Hz, 2H), 2.84 (t, J=7.6 Hz, 2H), 2.78-2.71 (m, 1H), 2.67 (t, J=7.6 Hz, 2H), 2.63-2.58 (m, 1H), 2.22 (s, 3H), 1.99-1.91 (m, 2H), 1.10 (t, J=7.6 Hz, 3H)

Examples 42 to 60

Target compounds of Examples 42 to 60 were obtained by means of a method as shown in Example 41.

Example 42. Preparation of (2S,3R,4R,5S,6R)-2-(4-ethyl-7-(4-methoxybenzyl)-2,3-dihydro-1H-indene-5-yl)-6-(hydroxymethyl)tetrahydro-2H-pyran-3,4,5-triol

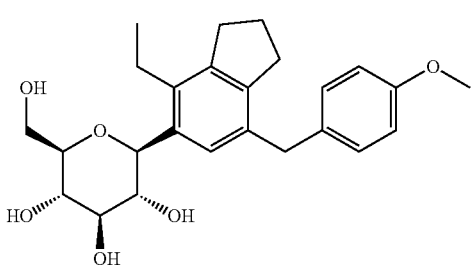 [SMILES: CCc1c([C@@H]2O[C@H](CO)[C@@H](O)[C@H](O)[C@H]2O)cc(Cc2ccc(OC)cc2)c2c1CCC2]

$^1$H NMR (400 MHz, CD$_3$OD); δ 7.07 (s, 1H), 7.02 (d, J=8.8 Hz, 2H), 6.75 (d, J=8.8 Hz, 2H), 4.41 (d, J=9.6 Hz, 1H), 3.83-3.80 (m, 3H), 3.70 (s, 3H), 3.61 (dd, J=11.2, 3.7 Hz, 1H), 3.55 (t, J=9.2 Hz, 1H), 3.47-3.43 (m, 1H), 3.35 (d, J=5.2 Hz, 2H), 2.84 (t, J=7.6 Hz, 2H), 2.78-2.73 (m, 1H), 2.68 (t, J=7.6 Hz, 2H), 2.64-2.58 (m, 1H), 1.99-1.92 (m, 2H), 1.11 (t, J=7.2 Hz, 3H)

Example 43. Preparation of (2S,3R,4R,5S,6R)-2-(7-(4-ethoxybenzyl)-4-ethyl-2,3-dihydro-1H-indene-5-yl)-6-(hydroxymethyl)tetrahydro-2H-pyran-3,4,5-triol

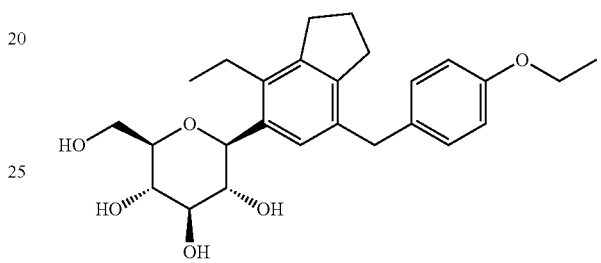

$^1$H NMR (400 MHz, CD$_3$OD); δ 7.12 (s, 1H), 7.06 (d, J=8.4 Hz, 2H), 6.78 (d, J=8.4 Hz, 2H), 4.45 (d, J=9.6 Hz, 1H), 4.00 (dd, J=7.2, 6.8 Hz, 2H), 3.67-3.54 (m, 2H), 3.51-3.48 (m, 1H), 3.43-41 (n, 2H), 2.88 (t, J=7.6 Hz, 2H), 2.83-2.61 (m, 5H), 2.04-1.96 (m, 3H), 1.35 (t, J=6.8 Hz, 4H), 1.15 (t, J=7.6 Hz, 3H)

Example 44. Preparation of (2S3R,4R,5S,6R)-2-(4-ethyl-7-(4-ethylbenzyl)-2,3-dihydro-1H-indene-5-yl)-6-(hydroxymethyl)tetrahydro-2H-pyran-3,4,5-triol

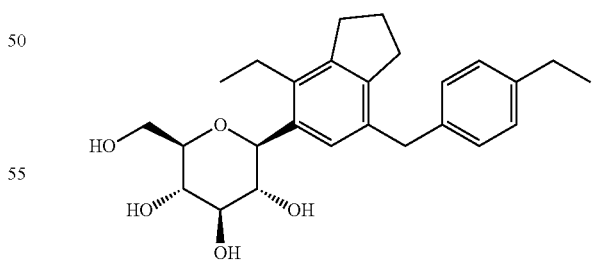

$^1$H NMR (400 MHz, CD$_3$OD); δ 7.13 (s, 1H), 7.05 (s, 4H), 4.43 (d, J=9.6 Hz, 1H), 3.84 (d, J=4.8 Hz, 3H), 3.76-3.57 (m, 3H), 3.52-3.48 (m, 3H), 2.89 (t, J=7.2 Hz, 2H), 2.83-2.78 (m, 1H), 2.73 (t, J=6.8 Hz, 2H), 2.68-2.61 (m, 1H), 2.59 (dd, J=8.0, 7.6 Hz, 3H), 2.04-1.96 (m, 3H), 1.21-1.07 (m, 5H)

Example 45. Preparation of (2S,3R,4R,5S,6R)-2-(4-ethyl-7-(4-fluorobenzyl)-2,3-dihydro-1H-indene-5-yl)-6-(hydroxymethyl)tetrahydro-2H-pyran-3,4,5-triol

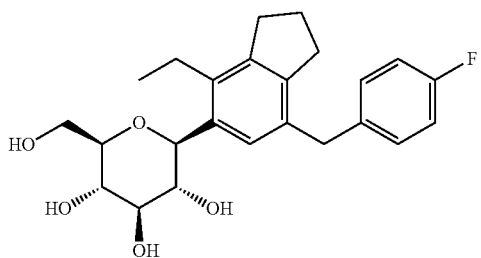 [SMILES: CCc1c([C@@H]2O[C@H](CO)[C@@H](O)[C@H](O)[C@H]2O)cc(Cc2ccc(F)cc2)c2c1CCC2]

¹H NMR (400 MHz, CD₃OD); δ 7.17-7.13 (m, 3H), 6.97-6.92 (m, 2H), 4.45 (d, J=9.2 Hz, 1H), 3.90-3.84 (m, 3H), 3.68-3.64 (m, 1H), 3.64-3.57 (m, 1H), 3.52-3.48 (m, 1H), 3.43-3.40 (m, 2H), 2.89 (t, J=7.4 Hz, 2H), 2.83-2.76 (m, 1H), 2.73-2.63 (m, 3H), 2.04-1.97 (m, 2H), 1.15 (t, J=7.6 Hz, 3H)

Example 46. Preparation of (2S,3R,4R,5S,6R)-2-(7-(4-chlorobenzyl)-4-ethyl-2,3-dihydro-1H-indene-5-yl)-6-(hydroxymethyl)tetrahydro-2H-pyran-3,4,5-triol

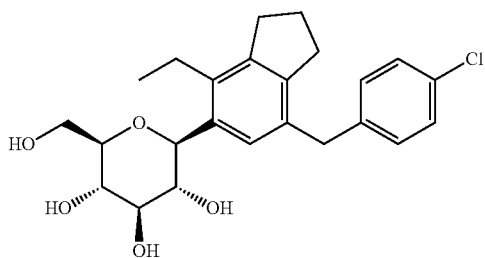 [SMILES: CCc1c([C@@H]2O[C@H](CO)[C@@H](O)[C@H](O)[C@H]2O)cc(Cc2ccc(Cl)cc2)c2c1CCC2]

¹H NMR (400 MHz, CD₃OD); δ 7.22 (d, J=8.0 Hz, 2H), 7.14 (d, J=8.0 Hz, 2H), 7.13 (s, 1H), 4.45 (d, J=9.2 Hz, 1H), 3.91 (s, 2H), 3.86 (d, J=11.6 Hz, 1H), 3.63 (dd, J=11.6, 4.0 Hz, 1H), 3.56 (t, J=9.2 Hz, 1H), 3.52-3.48 (m, 1H), 3.40 (d, J=5.2 Hz, 2H), 2.89 (t, J=7.6 Hz, 2H), 2.84-2.78 (m, 1H), 2.71 (t, J=7.6 Hz, 2H), 2.68-2.65 (m, 1H), 2.05-1.97 (m, 2H), 1.15 (t, J=7.6 Hz, 3H)

Example 47. Preparation of (2S,3R,4R,5S,6R)-2-(4-ethyl-7-(4-trifluoromethoxy)benzyl)-2,3-dihydro-1H-indene-5-yl)-6-(hydroxymethyl)tetrahydro-2H-pyran-3,4,5-triol

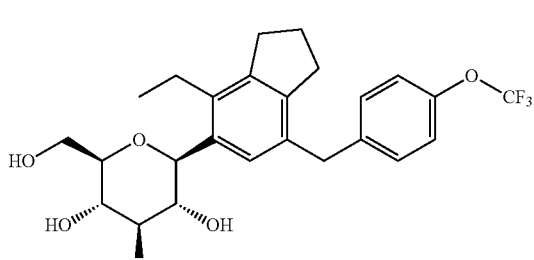

¹H NMR (400 MHz, CD₃OD); δ 7.24 (d, J=8.4 Hz, 2H), 7.16 (s, 1H), 7.13 (d, J=8.8 Hz, 2H), 4.45 (d, J=9.2 Hz, 1H), 3.95 (s, 2H) 3.86 (d, J=12.0 Hz, 1H), 3.66 (dd, J=12.0, 4.0 Hz, 1H), 3.59 (t, J=9.2 Hz, 1H), 3.56-3.48 (m, 1H), 3.41 (d, J=5.6 Hz, 2H), 2.89 (t, J=7.2 Hz, 2H), 2.84-2.79 (m, 1H), 2.72 (t, J=7.6 Hz, 2H), 2.69-2.63 (m, 1H), 2.05-1.98 (m, 2H), 1.16 (t, J=7.6 Hz, 3H)

Example 48. Preparation of (2S,3R,4R,5S,6R)-2-(4-ethyl-7-(4-trifluoromethyl)benzyl)-2,3-dihydro-1H-indene-5-yl)-6-(hydroxymethyl)tetrahydro-2H-pyran-3,4,5-triol

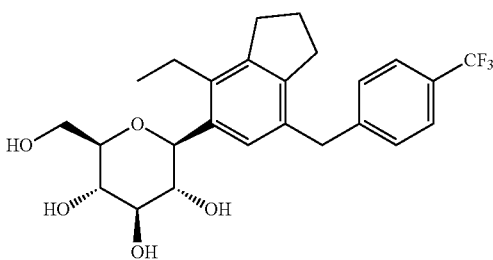

¹H NMR (400 MHz, CD₃OD); δ 7.53 (d, J=7.6 Hz, 2H), 7.35 (d, J=7.6 Hz, 2H), 7.17 (s, 1H), 4.46 (d, J=9.2 Hz, 1H), 4.01 (s, 2H), 3.86 (d, J=11.6 Hz, 1H), 3.69-3.65 (m, 1H), 3.62-3.57 (m, 1H), 3.53-3.48 (m, 1H), 3.41-3.40 (m, 2H), 2.92-2.88 (m, 2H), 2.84-2.77 (m, 1H), 2.77-2.64 (m, 3H), 2.05-1.98 (m, 2H), 1.16 (t, J=7.6 Hz, 3H)

Example 49. Preparation of (2S,3R,4R,5S,6R)-2-(7-(4-isopropoxybenzyl)-4-ethyl-2,3-dihydro-1H-indene-5-yl)-6-(hydroxymethyl)tetrahydro-2H-pyran-3,4,5-triol

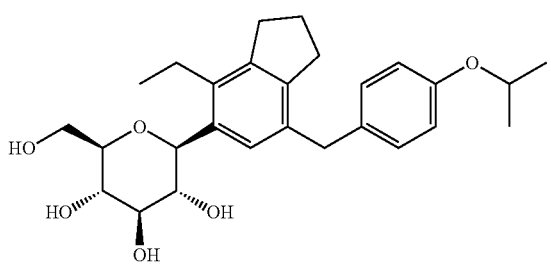 [SMILES: CCc1c([C@@H]2O[C@H](CO)[C@@H](O)[C@H](O)[C@H]2O)cc(Cc2ccc(OC(C)C)cc2)c2c1CCC2]

¹H NMR (400 MHz, CD₃OD); δ 7.12 (s, 1H), 7.05 (d, J=8.8 Hz, 2H), 6.76 (d, J=8.8 Hz, 2H), 4.55-4.48 (m, 1H) 4.44 (d, J=9.6 Hz, 1H), 3.87 (s, 1H), 3.68-3.57 (m, 2H), 3.52-3.48 (m, 1H), 3.43-3.39 (m, 2H), 3.31-3.18 (m, 2H), 2.88 (t, J=7.2 Hz, 2H), 2.83-2.63 (m, 4H), 2.04-1.97 (m, 2H), 1.27 (d, J=6.0 Hz, 6H), 1.15 (t, J=7.2 Hz, 3H)

Example 50. Preparation of (2S,3R,4R,5S,6R)-2-(7-(4-isopropylbenzyl)-4-ethyl-2,3-dihydro-1H-indene-5-yl)-6-(hydroxymethyl)tetrahydro-2H-pyran-3,4,5-triol

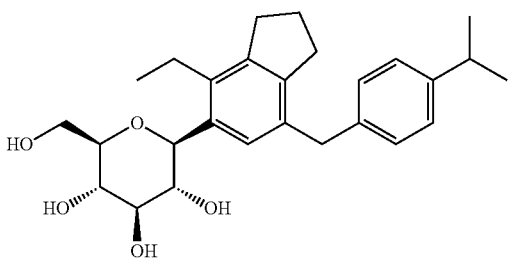 [SMILES: CCc1c([C@@H]2O[C@H](CO)[C@@H](O)[C@H](O)[C@H]2O)cc(Cc2ccc(C(C)C)cc2)c2c1CCC2]

¹H NMR (400 MHz, CD₃OD); δ 7.14 (s, 1H), 7.07 (dd, J=8.4, 4.8 Hz, 4H), 4.44 (d, J=9.2 Hz, 1H), 3.88-3.81 (m, 2H), 3.68-3.58 (m, 2H), 3.52-3.48 (m, 1H), 3.41-3.39 (m, 2H), 3.28-3.03 (m, 2H), 2.89 (t, J=7.2 Hz, 2H), 2.85-2.78 (m, 1H), 2.74 (t, J=7.6 Hz, 2H), 2.68-2.63 (m, 1H), 2.04-1.98 (m, 2H), 1.21 (d, J=6.8 Hz, 6H), 1.15 (t, J=7.2 Hz, 3H)

Example 51. Preparation of (2S,3R,4R,5S,6R)-2-(7-(biphenyl-3-ylmethyl)-4-ethyl-2,3-dihydro-1H-indene-5-yl)-6-(hydroxymethyl)tetrahydro-2H-pyran-3,4,5-triol

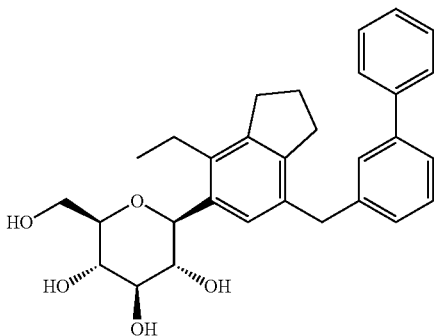 [SMILES: CCc1c([C@@H]2O[C@H](CO)[C@@H](O)[C@H](O)[C@H]2O)cc(Cc2cccc(-c3ccccc3)c2)c2c1CCC2]

¹H NMR (400 MHz, CD₃OD); δ 7.52 (d, J=7.6 Hz, 2H), 7.37 (t, J=7.6 Hz, 4H), 7.27 (d, J=7.2 Hz, 2H), 7.16 (s, 1H), 7.10 (d, J=6.8 Hz, 1H), 4.42 (d, J=9.2 Hz, 1H), 3.96 (s, 1H), 3.84-3.81 (dd, J=12.4, 11.2, 1H), 3.62-3.55 (m, 2H), 3.47 (t, J=8.4 Hz, 1H), 3.67-3.58 (m, 2H), 2.86 (t, J=6.8 Hz, 2H), 2.80-2.73 (m, 3H), 2.65-2.60 (m, 2H), 2.00-1.95 (m, 2H), 1.12 (t, J=7.2 Hz, 3H)

Example 52. Preparation of (2R,3S,4R,5R,6S)-2-(hydroxymethyl)-6-(7-(4-methoxybenzyl)-4-propyl-2,3-dihydro-1H-indene-5-yl)tetrahydro-2H-pyran-3,4,5-triol

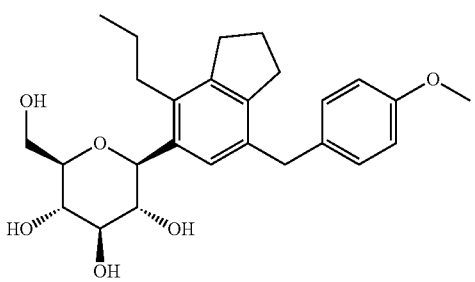 [SMILES: CCCc1c([C@@H]2O[C@H](CO)[C@@H](O)[C@H](O)[C@H]2O)cc(Cc2ccc(OC)cc2)c2c1CCC2]

¹H NMR (400 MHz, CD₃OD); δ 7.07 (s, 1H), 7.01 (d, J=8.8 Hz, 2H), 6.74 (d, J=8.8 Hz, 2H), 4.38 (d, J=9.6 Hz, 1H), 3.82-3.80 (m, 3H), 3.70 (s, 3H), 3.61 (dd, J=12.0, 5.6 Hz, 1H), 3.55 (t, J=8.8 Hz, 1H), 3.45 (t, J=8.8 Hz, 1H), 3.34 (d, J=6.8 Hz, 2H), 2.83 (t, J=6.8 Hz, 2H), 2.75-2.66 (m, 3H), 2.57-2.50 (m, 1H), 1.99-1.91 (m, 2H), 1.55-1.48 (m, 2H), 0.96 (t, J=7.6 Hz, 3H)

Example 53. Preparation of (2R,3S,4R,5R,6S)-2-(hydroxymethyl)-6-(7-(4-methylbenzyl)-4-propyl-2,3-dihydro-1H-indene-5-yl)tetrahydro-2H-pyran-3,4,5-triol

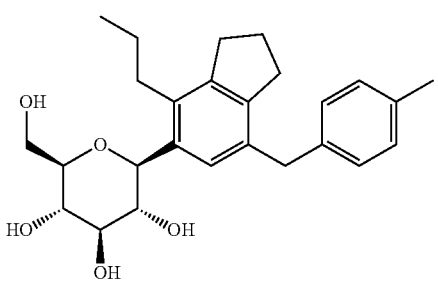 [SMILES: CCCc1c([C@@H]2O[C@H](CO)[C@@H](O)[C@H](O)[C@H]2O)cc(Cc2ccc(C)cc2)c2c1CCC2]

¹H NMR (400 MHz, CD₃OD); δ 7.08 (s, 1H), 6.99 (s, 4H), 4.38 (d, J=8.8 Hz, 1H), 3.83-3.80 (m, 3H), 3.64-3.59 (m, 1H), 3.55 (t, J=8.8 Hz, 1H), 3.45 (t, J=8.8 Hz, 1H), 3.35 (d, J=5.6 Hz, 2H), 2.83 (t, J=7.2 Hz, 2H), 2.75-2.66 (m, 3H), 2.56-2.50 (m, 1H), 2.23 (s, 3H), 1.99-1.91 (m, 2H), 1.55-1.50 (m, 2H), 0.97 (t, J=7.6 Hz, 3H)

Example 54. Preparation of (2S,3R,4R,5S,6R)-2-(7-(4-ethoxybenzyl)-4-propyl-2,3-dihydro-1H-indene-5-yl)-6-(hydroxymethyl)tetrahydro-2H-pyran-3,4,5-triol

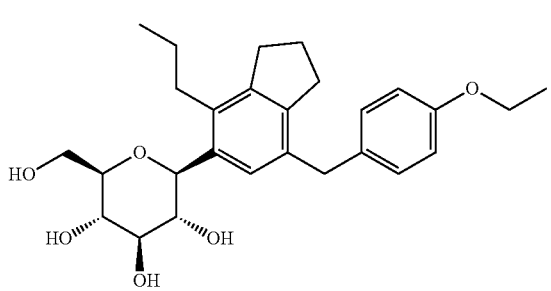 [SMILES: CCCc1c([C@@H]2O[C@H](CO)[C@@H](O)[C@H](O)[C@H]2O)cc(Cc2ccc(OCC)cc2)c2c1CCC2]

¹H NMR (400 MHz, CD₃OD); δ 7.08 (s, 1H), 7.01 (d, J=8.8 Hz, 2H), 6.74 (d, J=8.8 Hz, 2H), 4.40 (d, J=9.2 Hz, 1H), 3.96 (dd, J=7.2, 6.8 Hz, 2H), 3.83-3.82 (m, 1H), 3.62 (dd, J=6.4, 5.2 Hz, 1H), 3.55 (t, J=8.4 Hz, 1H), 3.45 (t, J=8.4 Hz, 1H) 3.38-3.36 (m, 2H), 3.27 (s, 2H), 2.83 (t, J=7.2 Hz, 2H), 2.74-2.67 (m, 3H), 2.58-2.52 (m, 1H), 1.99-1.93 (m, 2H), 1.56-1.50 (m, 2H). 1.31 (t, J=7.2 Hz, 3H), 0.97 (t, J=7.2 Hz, 3H)

Example 55. Preparation of (2S,3R,4R,5S,6R)-2-(7-(4-ethylbenzyl)-4-propyl-2,3-dihydro-1H-indene-5-yl)-6-(hydroxymethyl)tetrahydro-2H-pyran-3,4,5-triol

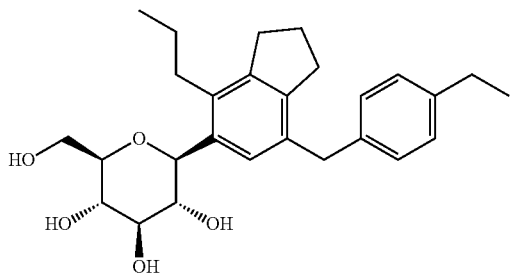 [SMILES: CCCc1c([C@@H]2O[C@H](CO)[C@@H](O)[C@H](O)[C@H]2O)cc(Cc2ccc(CC)cc2)c2c1CCC2]

$^1$H NMR (400 MHz, CD$_3$OD); δ 7.13 (s, 1H), 7.05 (s, 4H), 4.44 (d, J=8.4 Hz, 1H), 3.88 (s, 2H), 3.67-3.63 (m, 1H), 3.59 (t, J=4.8 Hz, 1H), 3.49 (t, J=7.6 Hz, 1H), 2.88 (t, J=7.6 Hz, 2H), 2.79-2.71 (m, 3H), 2.61-2.55 (m, 4H), 2.03-1.95 (m, 3H), 1.59-1.54 (m, 3H), 1.19 (t, J=7.6 Hz, 3H), 1.01 (t, J=7.2 Hz, 3H)

Example 56. Preparation of (2S,3R,4R,5S,6R)-2-(7-(4-fluorobenzyl)-4-propyl-2,3-dihydro-1H-indene-5-yl)-6-(hydroxymethyl)tetrahydro-2H-pyran-3,4,5-triol

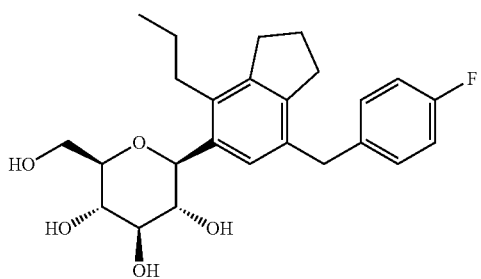 [SMILES: CCCc1c([C@@H]2O[C@H](CO)[C@@H](O)[C@H](O)[C@H]2O)cc(Cc2ccc(F)cc2)c2c1CCC2]

$^1$H NMR (400 MHz, CD$_3$OD); δ 7.17-7.13 (m, 3H), 6.97-6.92 (m, 2H), 4.43 (d, J=9.6 Hz, 1H), 3.90-3.84 (m, 3H), 3.68-3.63 (m, 1H), 3.60-3.56 (m, 1H), 3.51-3.47 (m, 1H), 3.43-3.39 (m, 2H), 2.88 (t, J=7.4 Hz, 2H), 2.80-2.70 (m, 3H), 2.62-2.54 (m, 1H), 2.03-1.96 (m, 2H), 1.59-1.52 (m, 2H), 1.01 (t, J=7.2 Hz, 3H)

Example 57. Preparation of (2S,3R,4R,5S,6R)-2-(4-butyl-7-(4-methoxybenzyl)-2,3-dihydro-1H-indene-5-yl)-6-(hydroxymethyl)tetrahydro-2H-pyran-3,4,5-triol

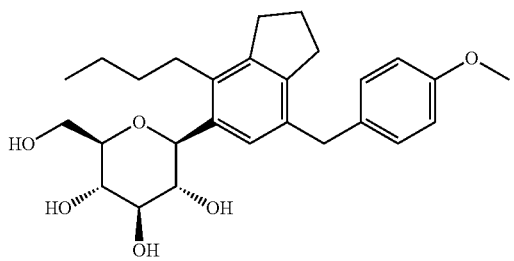

$^1$H NMR (400 MHz, CDCl$_3$); δ 7.03-7.01 (m, 3H), 6.76 (d, J=8.4 Hz, 2H), 4.45 (d, J=8.4 Hz, 1H), 4.19 (br s, 1H), 4.05 (br s, 1H), 3.81 (s, 2H), 3.75-3.66 (m, 6H), 3.46-3.40 (m, 1H), 2.85 (t, J=7.2 Hz, 2H), 2.72 (t, J=7.2 Hz, 2H), 2.70-2.63 (m, 1H), 2.60-2.51 (m, 1H), 2.03-1.97 (m, 2H), 1.46-1.35 (m, 4H), 0.92 (t, J=6.8 Hz, 3H)

Example 58. Preparation of (2S,3R,4R,5S,6R)-2-(4-butyl-7-(4-methylbenzyl)-2,3-dihydro-1H-indene-5-yl)-6-(hydroxymethyl)tetrahydro-2H-pyran-3,4,5-triol

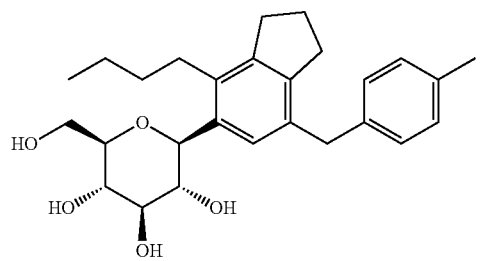 [SMILES: CCCCc1c([C@@H]2O[C@H](CO)[C@@H](O)[C@H](O)[C@H]2O)cc(Cc2ccc(C)cc2)c2c1CCC2]

$^1$H NMR (400 MHz, CDCl$_3$); δ 7.05-6.98 (m, 5H), 4.45 (d, J=8.4 Hz, 1H), 4.30 (br s, 1H), 4.15 (br s, 1H), 3.84 (s, 2H), 3.80-3.69 (m, 3H), 3.43 (m, 1H), 2.85 (t, J=7.2 Hz, 2H), 2.72 (t, J=7.2 Hz, 2H), 2.68-2.62 (m, 1H), 2.60-2.51 (m, 1H), 2.26 (s, 3H), 2.03-1.95 (m, 2H), 1.50-1.38 (m, 4H), 0.92 (t, J=6.8 Hz, 3H)

Example 59. Preparation of (2S,3R,4R,5S,6R)-2-(4-butyl-7-(4-ethoxybenzyl)-2,3-dihydro-1H-indene-5-yl)-6-(hydroxymethyl)tetrahydro-2H-pyran-3,4,5-triol

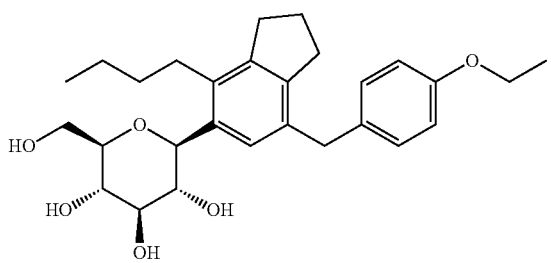 [SMILES: CCCCc1c([C@@H]2O[C@H](CO)[C@@H](O)[C@H](O)[C@H]2O)cc(Cc2ccc(OCC)cc2)c2c1CCC2]

$^1$H NMR (400 MHz, CD$_3$OD); δ 7.07 (s, 1H), 7.01 (d, J=8.4 Hz, 2H), 6.72 (d, J=8.4 Hz, 2H), 4.38 (d, J=9.2 Hz, 1H), 3.94 (q, J=7.2 Hz, 2H), 3.83-3.79 (m, 3H), 3.63-3.59 (m, 1H), 3.58-3.53 (m, 1H), 3.46-3.42 (m, 1H), 3.35-3.34 (m, 2H), 2.83 (t, J=7.6 Hz, 2H), 2.78-2.51 (m, 1H), 2.67 (t, J=7.6 Hz, 2H), 2.59-2.52 (m, 1H), 1.99-1.93 (m, 2H), 1.52-1.44 (m, 2H), 1.44-1.37 (m, 2H), 1.31 (t, J=6.8 Hz, 3H), 0.93 (t, J=6.8 Hz, 3H)

Example 60. Preparation of (2S,3R,4R,5S,6R)-2-(4-butyl-7-(4-ethylbenzyl)-2,3-dihydro-1H-indene-5-yl)-6-(hydroxymethyl)tetrahydro-2H-pyran-3,4,5-triol

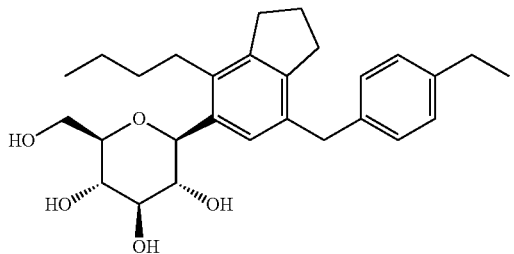 [SMILES: CCCCc1c([C@@H]2O[C@H](CO)[C@@H](O)[C@H](O)[C@H]2O)cc(Cc2ccc(CC)cc2)c2c1CCC2]

$^1$H NMR (400 MHz, CD$_3$OD); δ 7.08 (s, 1H), 7.01 (s, 4H), 4.38 (d, J=9.2 Hz, 1H), 3.83-3.79 (m, 3H), 3.63-3.59 (m, 1H), 3.58-3.53 (m, 1H), 3.46-3.42 (m, 1H), 3.35-3.34 (m, 2H), 2.83 (t, J=7.6 Hz, 2H), 2.78-2.67 (m, 3H), 2.59-2.50 (m, 3H), 1.98-1.91 (m, 2H), 1.54-1.44 (m, 2H), 1.44-1.34 (m, 2H), 1.14 (t, J=7.2 Hz, 3H), 0.93 (t, J=7.2 Hz, 3H)

Example 61. Preparation of (2R,3S,4R,5R,6S)-2-(hydroxymethyl)-6-(4-isopropyl-7-(4-methoxybenzyl)-2,3-dihydro-1H-indene-5-yl)tetrahydro-2H-pyran-3,4,5-triol

Step 1. Synthesis of (E)-ethyl 4-methylpent-2-enoate (61-1)

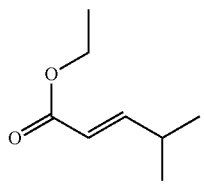

(Carbethoxymethylene)triphenylphosphorane (24.10 g, 69.34 mmol) was dissolved in DCM (101 mL), after which a resulting solution was cooled at 0° C., such that isobutyraldehyde (5.0 g, 69.34 mmol, aldrich) was slowly added dropwise into a resulting product, and then a resulting mixture was stirred at room temperature for 24 hours. A solvent of a reaction mixture was concentrated under reduced pressure, after which ether was added dropwise into a resulting concentrate, such that a resulting solid was filtered and removed. A resulting filtrate was collected and concentrated under reduced pressure, after which a resulting residue was purified by means of a silica gel column chromatography, so as to obtain the title compound (61-1) (8.48 g, 59.63 mmol, 86%).

$^1$H NMR (400 MHz, CDCl$_3$); δ 6.95 (dd, J=15.6, 6.8 Hz, 1H), 5.77 (dd, J=15.6, 1.2 Hz, 1H), 4.19 (q, J=7.2 Hz, 2H), 2.50-2.42 (m, 1H), 1.29 (t, J=7.2 Hz, 3H), 1.06 (d, J=6.8 Hz, 6H)

Step 2. Synthesis of (E)-4-methylpent-2-en-1-ol (61-2)

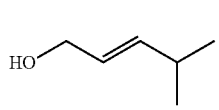

Lithium aluminum hydride (6.79 g, 178.9 mmol) and aluminum chloride (7.95 g, 59.63 mmol) were diluted in diethyl ether (500 mL), after which a resulting solution was cooled at −78° C. A compound according to an inventive title (61-1) (8.48 g, 59.63 mmol) in diethyl ether (50 mL) was slowly added dropwise into a reaction mixture, after which a resulting mixture was stirred at the same temperature for 2 hours. Water was slowly added dropwise into the resulting mixture, after which a reaction was completed, such that a resulting solid was filtered and removed. An organic layer was washed with brine, after which the resulting product was dried over anhydrous MgSO$_4$, filtered and concentrated under reduced pressure. A concentrated solution was dried under vacuum to obtain the title compound (61-2), which was used in a following step without an additional purification.

$^1$H NMR (400 MHz, CDCl$_3$); 5.65 (d, J=6.4 Hz, 1H), 5.60 (t, J=6.0 Hz, 1H), 4.09 (d, J=5.2 Hz, 2H), 2.35-2.27 (m, 1H), 1.00 (d, J=6.8 Hz, 6H)

Step 3. Synthesis of a Target Compound

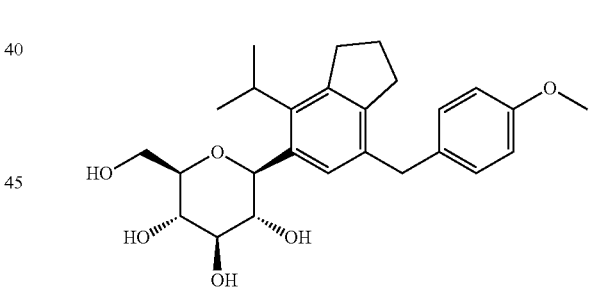

The target compound was obtained with the compound (61-2) by means of a method as shown from Steps 1 to 7 of Example 41.

$^1$H NMR (400 MHz, CD$_3$OD); δ 7.13 (s, 1H), 7.05 (d, J=8.4 Hz, 2H), 6.78 (d, J=8.4 Hz, 2H), 4.55 (br s, 1H), 3.87-3.85 (m, 3H), 3.74 (s, 3H), 3.68-3.64 (m, 1H), 3.62-3.56 (m, 1H), 3.51-3.47 (m, 2H), 3.40-3.38 (m, 2H), 3.02 (t, J=7.2 Hz, 2H), 2.67-2.61 (m, 2H), 1.99-1.92 (m, 2H), 1.32-1.30 (m, 6H)

Examples 62 and 63

Target compounds of Examples 62 and 63 were obtained by means of a method as shown in Example 61.

Example 62. Preparation of (2R,3S,4R,5R,6S)-2-(hydroxymethyl)-6-(4-isopropyl-7-(4-methoxybenzyl)-2,3-dihydro-1H-indene-5-yl)tetrahydro-2H-pyran-3,4,5-triol

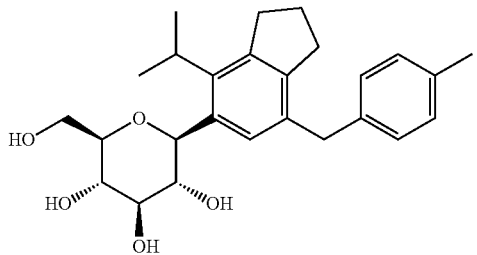 [SMILES: Cc1ccc(Cc2cc([C@@H]3O[C@H](CO)[C@@H](O)[C@H](O)[C@H]3O)c(C(C)C)c3c2CCC3)cc1]

¹H NMR (400 MHz, CD₃OD); δ 7.14 (s, 1H), 7.02 (s, 4H), 4.55 (br s, 1H), 3.86-3.84 (m, 3H), 3.67-3.64 (m, 1H), 3.62-3.57 (m, 1H), 3.52-3.48 (m, 2H), 3.40-3.38 (m, 2H), 3.00 (t, J=7.2 Hz, 2H), 2.67-2.63 (m, 2H), 2.27 (s, 3H), 1.98-1.91 (m, 2H), 1.32-1.30 (m, 6H)

Example 63. Preparation of (2S,3R,4R,5S,6R)-2-(4-cyclopentyl-7-(4-methylbenzyl)-2,3-dihydro-1H-indene-5-yl)-6-(hydroxymethyl)tetrahydro-2H-pyran-3,4,5-triol

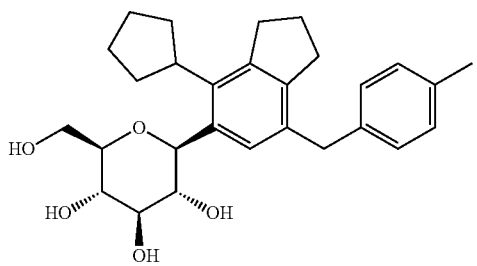 [SMILES: Cc1ccc(Cc2cc([C@@H]3O[C@H](CO)[C@@H](O)[C@H](O)[C@H]3O)c(C3CCCC3)c3c2CCC3)cc1]

¹H NMR (400 MHz, CD₃OD); δ 7.10 (br s, 1H), 7.98 (s, 4H), 4.50 (br s, 1H), 3.82-3.79 (m, 3H), 3.63-3.59 (m, 1H), 3.58-3.48 (m, 1H), 3.46-3.42 (m, 1H), 3.35-3.33 (m, 2H), 2.89 (t, J=7.2 Hz, 2H), 2.61 (t, J=7.2 Hz, 2H), 2.23 (s, 3H), 1.97-1.78 (m, 9H), 1.74-1.64 (m, 2H)

Example 64. Preparation of (2R,3S,4R,5R,6S)-2-(hydroxymethyl)-6-(4-isobutyl-7-(4-methylbenzyl)-2,3-dihydro-1H-indene-5-yl)tetrahydro-2H-pyran-3,4,5-triol Step 1. Synthesis of (2E,4E)-ethyl 7-methylocta-2,4-dienoate (64-1)

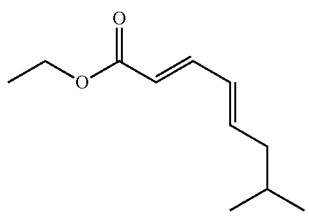

(64-1)

n-BuLi (14.5 mL, 36.29 mmol, 2.5 M in n-hexane) was added into a solution of isopentyltriphenylphosphonium bromide (15.0 g, 36.29 mmol) in THF (50 mL) at −78° C. in a nitrogen atmosphere, after which a resulting mixture was stirred at the same temperature for 1 hour. Ethyl 4-oxobut-2-enoate (1.55 g, 12.09 mmol) was slowly added dropwise into the resulting mixture, after which the resulting mixture was stirred for 30 minutes with a temperature rising to room temperature. A reaction mixture was cooled at 0° C., after which a saturated solution of ammonium chloride was added dropwise into a resulting product, so as to complete a reaction and perform an extraction with diethyl ether. An organic layer was dried over anhydrous MgSO₄, filtered and concentrated under reduced pressure. A resulting concentrate was purified by means of a silica gel column chromatography, so as to obtain the title compound (64-1) (1.89 g, 10.37 mmol, 86%).

¹H NMR (400 MHz, CDCl₃); 5.60 (dd, J=15.2, 11.2 Hz, 1H), 6.17 (t, J=11.2 Hz, 1H), 5.91-5.84 (m, 2H), 4.21 (q, J=7.2 Hz, 2H), 2.20 (t, J=7.2 Hz, 2H), 1.72-1.65 (m, 1H), 1.29 (t, J=7.2 Hz, 3H), 0.93 (d, J=6.8 Hz, 6H)

Step 2. Synthesis of a Target Compound

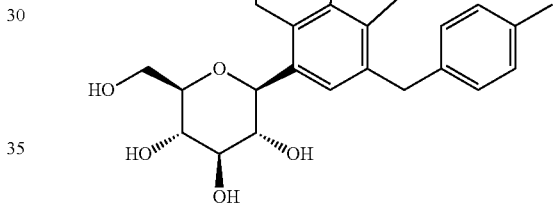

The target compound was obtained with the compound (64-1) by means of a method as shown from Steps 3 to 7 of Example 41.

¹H NMR (400 MHz, CDCl₃); δ 7.07-7.01 (m, 5H), 4.49 (d, J=8.4 Hz, 1H), 3.88-3.85 (m, 3H), 3.78-3.74 (m, 1H), 3.72-3.65 (m, 3H), 3.49-3.44 (m, 1H), 2.88 (t, J=7.2 Hz, 2H), 2.80-2.75 (m, 2H), 2.66-2.61 (m, 1H), 2.49-2.44 (m, 1H), 2.30 (s, 3H), 2.03-1.98 (m, 2H), 1.86-1.79 (m, 1H), 0.94 (d, J=6.4 Hz, 6H)

Example 65. Preparation of (2S,3R,4R,5S,6R)-2-(7-(4-ethylbenzyl)-4-isobutyl-2,3-dihydro-1H-indene-5-yl)-6-(hydroxymethyl)tetrahydro-2H-pyran-3,4,5-triol

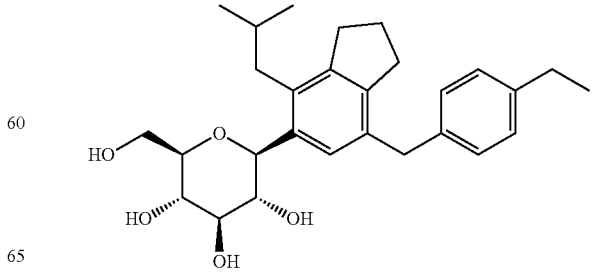

The target compound was obtained with a compound (64-1) by means of a method as shown in Step 2 of Example 64.

$^1$H NMR (400 MHz, CDCl$_3$); δ 7.11-7.05 (m, 5H), 4.50 (d, J=8.4 Hz, 1H), 3.89-3.87 (m, 3H), 3.81-3.74 (m, 1H), 3.73-3.66 (m, 3H), 3.51-3.46 (m, 1H), 2.88 (t, J=7.2 Hz, 2H), 2.82-2.76 (m, 2H), 2.66-2.58 (m, 3H), 2.49-2.44 (m, 1H), 2.03-1.97 (m, 2H), 1.86-1.79 (m, 1H), 1.21 (t, J=7.2 Hz, 3H), 0.94 (d, J=6.4 Hz, 6H)

Experimental Example 1. Human SGLT1, SGLT2 Gene Cloning and Construction of Cell Lines for Expressing Human SGLT1, SGLT2

Human SGLT1 (hSGLT1), human SGLT2 (hSGLT2) genes were amplified from a human marathon-ready cDNA library (Clontech)) by means of an PCR method, after which resulting amplified sequences were combined with a pcDNA 3.1(+) vector, which was a mammalian expression vector, so as to prepare recombinant expression vectors pcDNA3.1(+)/hSGLT1, pcDNA3.1(+)/hSGLT2. Resulting recombinant expression vectors were transformed into Chinese Hamster Ovarian cells, after which stably transformed clones were selected by means of a colony picking method by using a resistance to G418, a selective marker included in the vector. Out of selected clones, clones for expressing hSGLT1 and hSGLT2 were selected based on activity in analysis of $^{14}$C-α-methyl-D-glucopyranoside ($^{14}$C-AMG) transport.

Experimental Example 2. Inhibitory Effect on Human SGLT1, SGLT2 Activity

To analyze a sodium-dependent glucose transport, cells for expressing hSGLT1 and hSGLT2 were seeded at 1×10$^5$ cells per well into a 96-well culture plate, after which resulting cells were cultured in an RPMI 1640 medium containing 10% fetal bovine serum (FBS). In 1 day after culture, the resulting cells were cultured in a pre-treatment buffer solution (10 mM HEPES, 5 mM tris, 140 mM choline chloride, 2 mM KCl, 1 mM CaCl$_2$ and 1 mM MgCl$_2$, pH 7.4) under 37° C./5% CO$_2$ conditions for 10 minutes. Then, the resulting cells were cultured in a uptake buffer solution (10 mM HEPES, 5 mM tris, 140 mM NaCl, 2 mM KCl, 1 mM CaCl$_2$, 1 mM MgCl$_2$ and 1 mM AMGS pH 7.4) containing 14C-AMG (8 μM) and a compound of the present disclosure or a dimethyl sulfoxide (DMSO) vehicle under 37° C./5% CO$_2$ conditions for 2 hours. After culture, the cells were washed twice with a washing buffer solution (a pre-treatment buffer solution containing 10 mM AMG at room temperature), after which a radiation thereof was measured by using a liquid scintillation counter. IC$_{50}$ of each compound was measured according to a non-linear regression analysis by using SigmaPlot (Document Analytical Biochemistry 429: 70-75, Molecular and Cellular Biochemistry 280: 91-98, 2005). SGLT1/2 in-vitro assay results are shown in a following Table 1.

TABLE 1

| Compound | SGLT1 (IC$_{50}$, nM) | SGLT2 (IC$_{50}$, nM) |
| --- | --- | --- |
| Canagliflozin | 550 | 4.9 |
| Example 1 | 9.1 | 1.3 |
| Example 2 | 76 | 3.0 |
| Example 3 | 142 | — |
| Example 5 | 40 | 2.8 |
| Example 6 | 190 | — |
| Example 7 | 296 | — |
| Example 13 | 15 | 1.2 |
| Example 16 | 14.3 | — |
| Example 34 | 295 | — |
| Example 41 | 41.82 | 3.68 |
| Example 42 | 60.51 | 2.73 |
| Example 52 | 235.63 | 9.04 |
| Example 53 | 94.72 | 1.83 |
| Example 57 | 373.28 | 5.86 |
| Example 58 | 288.61 | 12.06 |
| Example 61 | 198.68 | 2.04 |
| Example 62 | 92.74 | 1.46 |
| Example 64 | 518.28 | 19.10 |
| Example 65 | 1611.05 | 37.97 |

Experimental Example 3. Experiment on Measurement of Urinary Glucose Excretion (UGE Test)

With regard to a pharmaceutical efficacy of a compound prepared in the Example, 1 mg/kg of such compound was orally administered into a normal mouse, after which an UGE test was performed. As a result, it was identified that the compound of the present disclosure increased a urine glucose (mg/24 h) and decreased a blood glucose level (mg/dl).

Accordingly, the compound of the present disclosure is expected to be valuably used in treatment or prevention of diabetes.

Experimental Example 4. Experiment on Measurement of Anti-Diabetes Activity

With regard to a pharmaceutical efficacy of a compound prepared in the Example, 2 mg/kg of such compound was orally administered into each db/db mouse and DIO mouse for 4 weeks, after which a change in blood sugar level was measured. As a result, it was identified that the blood sugar level was remarkably decreased.

Also, with regard to a pharmaceutical efficacy of the compound prepared in the Example above, such compound was administered into an OB/OB mouse for 2 weeks, after which a change in blood sugar level was measured. As a result, it was identified that the blood sugar level was remarkably decreased.

Accordingly, the compound of the present disclosure is expected to be valuably used in treatment or prevention of diabetes.

Experimental Example 5. Experiment on Measurement of Oral Glucose Resistance

To identify a pharmaceutical efficacy of a compound prepared in the Example, a post prandial glucose was measured with regard to a normal mouse. As a result, it was identified that a blood glucose AUC0-4 h: mg-h/dL in 4 hours after administration of the compound (1 mg/kg) was significantly decreased.

Such result was also found in an experiment with a db/db mouse, thus it was identified that blood glucose AUC0-4 h: mg-h/dL in 4 hours after administration of the compound (2 mg/kg) was significantly decreased.

Also, in the experiment with the db/db mouse, it was also identified that blood glucose AUC0-4 h: mg-h/dL in 4 hours after administration of the compound (10 mg/kg) was significantly decreased, too.

Accordingly, the compound of the present disclosure is expected to be valuably used in treatment or prevention of diabetes.

While specific portions of the present disclosure have been described in detail above, it is apparent to those skilled in the art that such detailed descriptions are set forth to illustrate exemplary embodiments only, but are not construed to limit the scope of the present disclosure. Thus, it should be understood that the substantial scope of the present disclosure is defined by the accompanying claims and equivalents thereto.

The invention claimed is:

1. A compound represented by Formula 1 or pharmaceutically acceptable salts thereof:

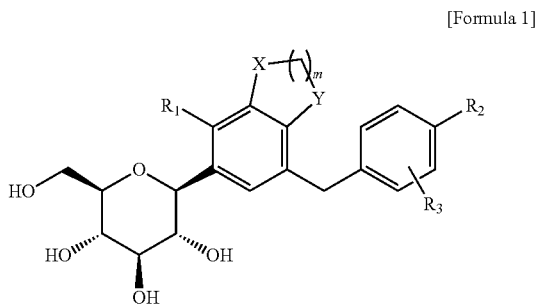

[Formula 1]

wherein,
X and Y are each independently —CH$_2$— or —O—;
m is 1 or 2;
R$_1$ is halogen, C$_1$-C$_4$ alkyl, C$_3$-C$_7$ cycloalkyl or C$_1$-C$_4$ alkoxy (wherein at least one hydrogen of the said C$_1$-C$_4$ alkyl may be each independently unsubstituted or substituted with halogen);
R$_2$ and R$_3$ are each independently hydrogen, halogen, C$_1$-C$_4$ alkyl, C$_2$-C$_4$ alkenyl, C$_3$-C$_7$ cycloalkyl, C$_1$-C$_4$ alkoxy, —OCF$_3$, —SR$_5$, phenyl, biphenyl, terphenyl, naphthyl, anthracene, fluorene or pyrenyl (wherein at least one hydrogen of the said C$_1$-C$_4$ alkyl, C$_2$-C$_4$ alkenyl and C$_3$-C$_7$ cycloalkyl may be each independently unsubstituted or substituted with halogen, and at least one hydrogen of the said phenyl, biphenyl, terphenyl, naphthyl, anthracene, fluorene or pyrenyl may be each independently unsubstituted or substituted with at least one substituent selected from the group consisting of halogen, C$_1$-C$_4$ alkyl, and C$_1$-C$_4$ alkoxy); and
R$_5$ is C$_1$-C$_4$ alkyl.

2. The compound represented by the Formula 1 or the pharmaceutically acceptable salts thereof, according to claim 1, wherein
X is —CH$_2$—;
Y is —CH$_2$— or —O—;
m is 1 or 2;
R$_1$ is halogen, C$_1$-C$_4$ alkyl, C$_3$-C$_7$ cycloalkyl or C$_1$-C$_4$ alkoxy (wherein the said C$_1$-C$_4$ alkyl is unsubstituted);
R$_2$ and R$_3$ are each independently halogen, C$_1$-C$_4$ alkyl, C$_2$-C$_4$ alkenyl, C$_1$-C$_4$ alkoxy, —OCF$_3$, —SR$_5$ or phenyl (wherein at least one hydrogen of the said C$_1$-C$_4$ alkyl may be unsubstituted or substituted with halogen, and hydrogen of the said C$_2$-C$_4$ alkenyl and phenyl are unsubstituted); and
R$_5$ is C$_1$-C$_4$ alkyl.

3. The compound represented by the Formula 1 or the pharmaceutically acceptable salts thereof, according to claim 1, wherein such compound is selected from the group consisting of the following compounds:
(2R,3S,4R,5R,6S)-2-(hydroxymethyl)-6-(7-(4-methoxybenzyl)-4-methyl-2,3-dihydro-1H-inden-5-yl)tetrahydro-2H-pyran-3,4,5-triol;
(2S,3R,4R,5S,6R)-2-(7-(4-ethoxybenzyl)-4-methyl-2,3-dihydro-1H-inden-5-yl)-6-(hydroxymethyl)tetrahydro-2H-pyran-3,4,5-triol;
(2R,3S,4R,5R,6S)-2-(hydroxymethyl)-6-(7-(4-isopropoxybenzyl)-4-methyl-2,3-dihydro-1H-inden-5-yl)tetrahydro-2H-pyran-3,4,5-triol;
(2R,3S,4R,5R,6S)-2-(hydroxymethyl)-6-(4-methyl-7-(4-methylbenzyl)-2,3-dihydro-1H-inden-5-yl)tetrahydro-2H-pyran-3,4,5-triol;
(2S,3R,4R,5S,6R)-2-(7-(4-ethylbenzyl)-4-methyl-2,3-dihydro-1H-inden-5-yl)-6-(hydroxymethyl)tetrahydro-2H-pyran-3,4,5-triol;
(2R,3S,4R,5R,6S)-2-(hydroxymethyl)-6-(4-methyl-7-(4-propylbenzyl)-2,3-dihydro-1H-inden-5-yl)tetrahydro-2H-pyran-3,4,5-triol;
(2R,3S,4R,5R,6S)-2-(hydroxymethyl)-6-(7-(4-isopropylbenzyl)-4-methyl-2,3-dihydro-1H-inden-5-yl)tetrahydro-2H-pyran-3,4,5-triol;
(2R,3S,4R,5R,6S)-2-(hydroxymethyl)-6-(4-methyl-7-(4-vinylbenzyl)-2,3-dihydro-1H-inden-5-yl)tetrahydro-2H-pyran-3,4,5-triol;
(2R,3S,4R,5R,6S)-2-(hydroxymethyl)-6-(4-methyl-7-(4-trifluoromethyl)benzyl)-2,3-dihydro-1H-inden-5-yl)tetrahydro-2H-pyran-3,4,5-triol;
(2R,3S,4R,5R,6S)-2-(hydroxymethyl)-6-(4-methyl-7-(4-trifluoromethoxy)benzyl)-2,3-dihydro-1H-inden-5-yl)tetrahydro-2H-pyran-3,4,5-triol;
(2S,3R,4R,5S,6R)-2-(7-(3,4-dimethoxybenzyl)-4-methyl-2,3-dihydro-1H-inden-5-yl)-6-(hydroxymethyl)tetrahydro-2H-pyran-3,4,5-triol;
(2S,3R,4R,5S,6R)-2-(7-(2,4-dimethoxybenzyl)-4-methyl-2,3-dihydro-1H-inden-5-yl)-6-(hydroxymethyl)tetrahydro-2H-pyran-3,4,5-triol;
(2R,3S,4R,5R,6S)-2-(hydroxymethyl)-6-(4-methyl-7-(4-methylthio)benzyl)-2,3-dihydro-1H-inden-5-yl)tetrahydro-2H-pyran-3,4,5-triol;
(2S,3R,4R,5S,6R)-2-(7-(4-fluorobenzyl)-4-methyl-2,3-dihydro-1H-inden-5-yl)-6-(hydroxymethyl)tetrahydro-2H-pyran-3,4,5-triol;
(2S,3R,4R,5S,6R)-2-(7-(4-fluoro-3-methylbenzyl)-4-methyl-2,3-dihydro-1H-inden-5-yl)-6-(hydroxymethyl)tetrahydro-2H-pyran-3,4,5-triol;
(2S,3R,4R,5S,6R)-2-(7-(4-chlorobenzyl)-4-methyl-2,3-dihydro-1H-inden-5-yl)-6-(hydroxymethyl)tetrahydro-2H-pyran-3,4,5-triol;
(2R,3S,4R,5R,6S)-2-(hydroxymethyl)-6-(4-(4-methoxybenzyl)-1-methyl-5,6,7,8-tetrahydronaphthalene-2-yl)tetrahydro-2H-pyran-3,4,5-triol;
(2R,3S,4R,5R,6S)-2-(hydroxymethyl)-6-(1-methyl-4-(4-methylbenzyl)-5,6,7,8-tetrahydronaphthalene-2-yl)tetrahydro-2H-pyran-3,4,5-triol;
(2R,3S,4R,5R,6S)-2-(hydroxymethyl)-6-(1-methyl-4-(4-trifluoromethyl)benzyl)-5,6,7,8-tetrahydronaphthalene-2-yl)tetrahydro-2H-pyran-3,4,5-triol;
(2R,3S,4R,5R,6S)-2-(hydroxymethyl)-6-(1-methyl-4-(4-trifluoromethoxy)benzyl)-5,6,7,8-tetrahydronaphthalene-2-yl)tetrahydro-2H-pyran-3,4,5-triol;
(2R,3S,4R,5R,6S)-2-(hydroxymethyl)-6-(1-methyl-4-(4-(methylthio)benzyl)-5,6,7,8-tetrahydronaphthalene-2-yl)tetrahydro-2H-pyran-3,4,5-triol;

(2S,3R,4R,5S,6R)-2-(4-(4-chlorobenzyl)-1-methyl-5,6,7,8-tetrahydronaphthalene-2-yl)-6-(hydroxymethyl)tetrahydro-2H-pyran-3,4,5-triol;

(2R,3S,4R,5R,6S)-2-(hydroxymethyl)-6-(7-(4-methoxybenzyl)-4-methyl-2,3-dihydrobenzofuran-5-yl)tetrahydro-2H-pyran-3,4,5-triol;

(2S,3R,4R,5S,6R)-2-(7-(4-ethoxybenzyl)-4-methyl-2,3-dihydrobenzofuran-5-yl)-6-(hydroxymethyl)tetrahydro-2H-pyran-3,4,5-triol;

(2R,3S,4R,5R,6S)-2-(hydroxymethyl)-6-(4-methyl-7-(4-(methylthio)benzyl)-2,3-dihydrobenzofuran-5-yl)tetrahydro-2H-pyran-3,4,5-triol;

(2S,3R,4R,5S,6R)-2-(7-(4-ethylbenzyl)-4-methyl-2,3-dihydrobenzofuran-5-yl)-6-(hydroxymethyl)tetrahydro-2H-pyran-3,4,5-triol;

(2R,3S,4R,5R,6S)-2-(hydroxymethyl)-6-(4-methyl-7-(4-vinylbenzyl)-2,3-dihydrobenzofuran-5-yl)tetrahydro-2H-pyran-3,4,5-triol;

(2S,3R,4R,5S,6R)-2-(4-chloro-7-(4-ethoxybenzyl)-2,3-dihydrobenzofuran-5-yl)-6-(hydroxymethyl)tetrahydro-2H-pyran-3,4,5-triol;

(2R,3S,4R,5R,6S)-2-(hydroxymethyl)-6-(4-(4-methoxybenzyl)-7-methyl-2,3-dihydrobenzofuran-6-yl)tetrahydro-2H-pyran-3,4,5-triol;

(2R,3S,4R,5R,6S)-2-(hydroxymethyl)-6-(7-methyl-4-(4-vinylbenzyl)-2,3-dihydrobenzofuran-6-yl)tetrahydro-2H-pyran-3,4,5-triol;

(2R,3S,4R,5R,6S)-2-(hydroxymethyl)-6-(8-methoxy-5-(4-methoxybenzyl)chroman-7-yl)tetrahydro-2H-pyran-3,4,5-triol;

(2R,3S,4R,5R,6S)-2-(hydroxymethyl)-6-(8-methoxy-5-(4-methylbenzyl)chroman-7-yl)tetrahydro-2H-pyran-3,4,5-triol;

(2S,3R,4R,5S,6R)-2-(5-(4-ethoxybenzyl)-8-methylchroman-7-yl)-6-(hydroxymethyl)tetrahydro-2H-pyran-3,4,5-triol;

(2S,3R,4R,5S,6R)-2-(4-ethyl-7-(4-methylbenzyl)-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-methoxybenzyl)-2,3-dihydro-1H-indene-5-yl)-6-(hydroxymethyl)tetrahydro-2H-pyran-3,4,5-triol;

(2S,3R,4R,5S,6R)-2-(7-(4-ethoxybenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-ethylbenzyl)-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-fluorobenzyl)-2,3-dihydro-1H-indene-5-yl)-6-(hydroxymethyl)tetrahydro-2H-pyran-3,4,5-triol;

(2S,3R,4R,5S,6R)-2-(7-(4-chlorobenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-trifluoromethoxy)benzyl)-2,3-dihydro-1H-indene-5-yl)-6-(hydroxymethyl)tetrahydro-2H-pyran-3,4,5-triol;

(2S,3R,4R,5S,6R)-2-(4-ethyl-7-(4-trifluoromethyl)benzyl)-2,3-dihydro-1H-indene-5-yl)-6-(hydroxymethyl)tetrahydro-2H-pyran-3,4,5-triol;

(2S,3R,4R,5S,6R)-2-(7-(4-isopropoxybenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(7-(4-isopropylbenzyl)-4-ethyl-2,3-dihydro-1H-indene-5-yl)-6-(hydroxymethyl)tetrahydro-2H-pyran-3,4,5-triol;

(2S,3R,4R,5S,6R)-2-(7-(biphenyl-3-ylmethyl)-4-ethyl-2,3-dihydro-1H-indene-5-yl)-6-(hydroxymethyl)tetrahydro-2H-pyran-3,4,5-triol;

(2R,3S,4R,5R,6S)-2-(hydroxymethyl)-6-(7-(4-methoxybenzyl)-4-propyl-2,3-dihydro-1H-indene-5-yl)tetrahydro-2H-pyran-3,4,5-triol;

(2R,3S,4R,5R,6S)-2-(hydroxymethyl)-6-(7-(4-methylbenzyl)-4-propyl-2,3-dihydro-1H-indene-5-yl)tetrahydro-2H-pyran-3,4,5-triol;

(2S,3R,4R,5S,6R)-2-(7-(4-ethoxybenzyl)-4-propyl-2,3-dihydro-1H-indene-5-yl)-6-(hydroxymethyl)tetrahydro-2H-pyran-3,4,5-triol;

(2S,3R,4R,5S,6R)-2-(7-(4-ethylbenzyl)-4-propyl-2,3-dihydro-1H-indene-5-yl)-6-(hydroxymethyl)tetrahydro-2H-pyran-3,4,5-triol;

(2S,3R,4R,5S,6R)-2-(7-(4-fluorobenzyl)-4-propyl-2,3-dihydro-1H-indene-5-yl)-6-(hydroxymethyl)tetrahydro-2H-pyran-3,4,5-triol;

(2S,3R,4R,5S,6R)-2-(4-butyl-7-(4-methoxybenzyl)-2,3-dihydro-1H-indene-5-yl)-6-(hydroxymethyl)tetrahydro-2H-pyran-3,4,5-triol;

(2S,3R,4R,5S,6R)-2-(4-butyl-7-(4-methylbenzyl)-2,3-dihydro-1H-indene-5-yl)-6-(hydroxymethyl)tetrahydro-2H-pyran-3,4,5-triol;

(2S,3R,4R,5S,6R)-2-(4-butyl-7-(4-ethoxybenzyl)-2,3-dihydro-1H-indene-5-yl)-6-(hydroxymethyl)tetrahydro-2H-pyran-3,4,5-triol;

(2S,3R,4R,5S,6R)-2-(4-butyl-7-(4-ethylbenzyl)-2,3-dihydro-1H-indene-5-yl)-6-(hydroxymethyl)tetrahydro-2H-pyran-3,4,5-triol;

(2R,3S,4R,5R,6S)-2-(hydroxymethyl)-6-(4-isopropyl-7-(4-methoxybenzyl)-2,3-dihydro-1H-indene-5-yl)tetrahydro-2H-pyran-3,4,5-triol;

(2R,3S,4R,5R,6S)-2-(hydroxymethyl)-6-(4-isopropyl-7-(4-methylbenzyl)-2,3-dihydro-1H-indene-5-yl)tetrahydro-2H-pyran-3,4,5-triol;

(2S,3R,4R,5S,6R)-2-(4-cyclopentyl-7-(4-methylbenzyl)-2,3-dihydro-1H-indene-5-yl)-6-(hydroxymethyl)tetrahydro-2H-pyran-3,4,5-triol;

(2R,3S,4R,5R,6S)-2-(hydroxymethyl)-6-(4-isobutyl-7-(4-methylbenzyl)-2,3-dihydro-1H-indene-5-yl)tetrahydro-2H-pyran-3,4,5-triol; and (2S,3R,4R,5S,6R)-2-(7-(4-ethylbenzyl)-4-isobutyl-2,3-dihydro-1H-indene-5-yl)-6-(hydroxymethyl)tetrahydro-2H-pyran-3,4,5-triol.

4. A method for preparing the compound represented by the Formula 1 or the pharmaceutically acceptable salts thereof, wherein the method comprises following steps:

(S1) reacting a compound of a following Formula II with a compound of a following Formula III to obtain a compound of a following Formula IV; and (S2) performing deprotection-reduction or reduction-deprotection for the compound of the Formula IV above to obtain a compound of a following Formula I:

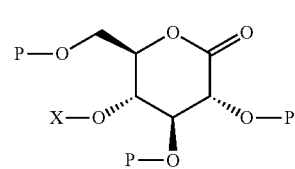

[Formula II]

-continued

[Formula III]

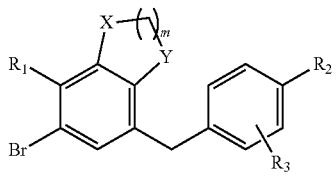

[Formula IV]

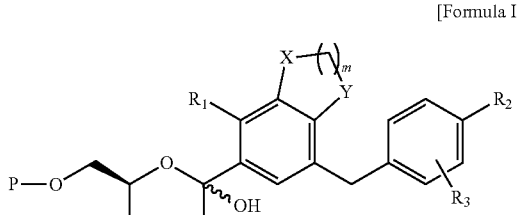

[Formula I]

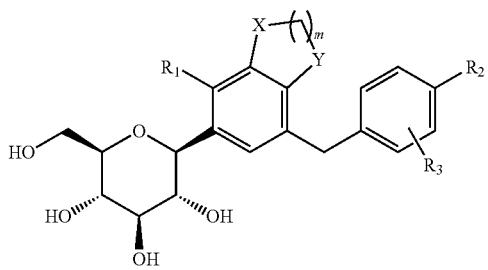

wherein,

X, Y, m, $R_1$, $R_2$ and $R_3$ are as defined claim 1, and P is trimethylsilyl or benzyl.

5. The method according to claim 4, wherein, if P is trimethylsilyl, a compound of a following Formula V is obtained by deprotecting the compound of the Formula IV, and the compound of the Formula I is obtained by reducing the compound of the Formula V:

[Formula V]

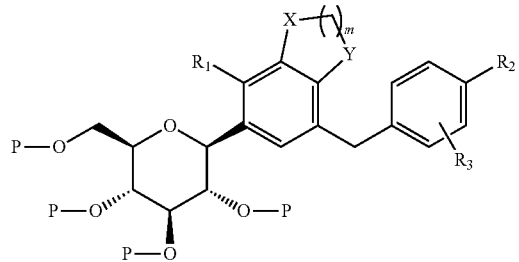

wherein,

X and Y are each independently —$CH_2$— or —O—, m is 1 or 2;

$R_1$ is halogen, $C_1$-$C_4$ alkyl, $C_3$-$C_7$ cycloalkyl or $C_1$-$C_4$ alkoxy (wherein at least one hydrogen of the said $C_1$-$C_4$ alkyl may be each independently unsubstituted or substituted with halogen);

$R_2$ and $R_3$ are each independently hydrogen, halogen, $C_1$-$C_4$ alkyl, $C_2$-$C_4$ alkenyl, $C_3$-$C_7$ cycloalkyl, $C_1$-$C_4$ alkoxy, —$OCF_3$, —$SR_5$, phenyl, biphenyl, terphenyl, naphthyl, anthracene, fluorene or pyrenyl (wherein at least one hydrogen of the said $C_1$-$C_4$ alkyl, $C_2$-$C_4$ alkenyl and $C_3$-$C_7$ cycloalkyl may be each independently unsubstituted or substituted with halogen, and at least one hydrogen of the said phenyl, biphenyl, terphenyl, naphthyl, anthracene, fluorene or pyrenyl may be each independently unsubstituted or substituted with at least one substituent selected from the group consisting of halogen, $C_1$-$C_4$ alkyl, and $C_1$-$C_4$ alkoxy); and $R_5$ is $C_1$-$C_4$ alkyl.

6. The method according to claim 4, wherein, if P is benzyl, a compound of a following Formula VI is obtained by reducing the compound of the Formula IV, and the compound of the Formula I is obtained by deprotecting the compound of the Formula VI:

[Formula VI]

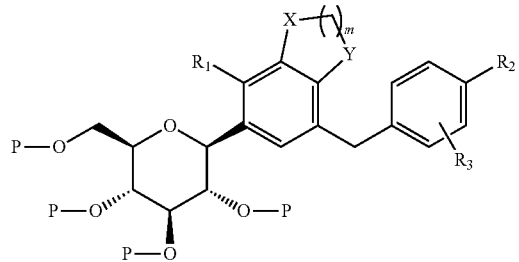

wherein,

X and Y are each independently —$CH_2$— or —O—, m is 1 or 2;

$R_1$ is halogen, $C_1$-$C_4$ alkyl, $C_3$-$C_7$ cycloalkyl or $C_1$-$C_4$ alkoxy (wherein at least one hydrogen of the said $C_1$-$C_4$ alkyl may be each independently unsubstituted or substituted with halogen);

$R_2$ and $R_3$ are each independently hydrogen, halogen, $C_1$-$C_4$ alkyl, $C_2$-$C_4$ alkenyl, $C_3$-$C_7$ cycloalkyl, $C_1$-$C_4$ alkoxy, —$OCF_3$, —$SR_5$, phenyl, biphenyl, terphenyl, naphthyl, anthracene, fluorene or pyrenyl (wherein at least one hydrogen of the said $C_1$-$C_4$ alkyl, $C_2$-$C_4$ alkenyl and $C_3$-$C_7$ cycloalkyl may be each independently unsubstituted or substituted with halogen, and at least one hydrogen of the said phenyl, biphenyl, terphenyl, naphthyl, anthracene, fluorene or pyrenyl may be each independently unsubstituted or substituted with at least one substituent selected from the group consisting of halogen, $C_1$-$C_4$ alkyl, and $C_1$-$C_4$ alkoxy); and $R_5$ is $C_1$-$C_4$ alkyl.

7. A method for treating an SGLT activity-related disease in a patient, comprising, administering to the patient the compound of the Formula 1 described in claim 1 or the pharmaceutically acceptable salts thereof as an active component.

8. The method for treating an SGLT activity-related disease, according to claim 7, wherein the compound of Formula 1 or the pharmaceutically acceptable salts thereof inhibits SGLT1, SGLT2 or both thereof.

9. The method for treating an SGLT activity-related disease, according to claim 7, wherein the SGLT activity-related disease is diabetes.

* * * * *

UNITED STATES PATENT AND TRADEMARK OFFICE
CERTIFICATE OF CORRECTION

PATENT NO. : 10,752,604 B2
APPLICATION NO. : 16/067707
DATED : August 25, 2020
INVENTOR(S) : Joon Woo Nam et al.

Page 1 of 1

It is certified that error appears in the above-identified patent and that said Letters Patent is hereby corrected as shown below:

On the Title Page

Column 1, Item (71), Line 1:
Delete "Je II" and insert -- Je Il --, therefor.

Column 1, Item (73), Line 1:
Delete "Je II" and insert -- Je Il --, therefor.

In the Claims

Column 79, Line 34:
In Claim 4: after "defined" insert -- in --.

Signed and Sealed this
Twenty-second Day of December, 2020

Andrei Iancu
*Director of the United States Patent and Trademark Office*